US012371474B2

(12) United States Patent
Guo et al.

(10) Patent No.: US 12,371,474 B2
(45) Date of Patent: Jul. 29, 2025

(54) RECOMBINANT ADENO-ASSOCIATED VIRAL VECTORS FOR TREATING BIETTI CRYSTALLINE DYSTROPHY

(71) Applicant: SHANGHAI VITALGEN BIOPHARMA CO., LTD., Shanghai (CN)

(72) Inventors: Lu Guo, Haidian (CN); Yezheng Tao, Shanghai (CN); Shin-Shay Tian, Shanghai (CN); Bin Qu, Shanghai (CN); Wei Li, Beijing (CN); Xi Zhu, Shanghai (CN); Xiaoping Zhao, Shanghai (CN)

(73) Assignee: SHANGHAI VITALGEN BIOPHARMA CO., LTD., Shanghai (CN)

( * ) Notice: Subject to any disclaimer, the term of this patent is extended or adjusted under 35 U.S.C. 154(b) by 0 days.

(21) Appl. No.: 18/410,043

(22) Filed: Jan. 11, 2024

(65) Prior Publication Data

US 2024/0309068 A1 Sep. 19, 2024

Related U.S. Application Data

(63) Continuation of application No. PCT/CN2022/106089, filed on Jul. 15, 2022.

(51) Int. Cl.
*A61K 48/00* (2006.01)
*A61K 38/41* (2006.01)
*C07K 14/80* (2006.01)
*C12N 15/00* (2006.01)
*C12N 15/63* (2006.01)
*C12N 15/86* (2006.01)
*A01K 67/00* (2006.01)

(52) U.S. Cl.
CPC ............ *C07K 14/80* (2013.01); *A61K 38/415* (2013.01); *A61K 48/0066* (2013.01); *C12N 15/86* (2013.01); *C12N 2750/14143* (2013.01); *C12N 2830/48* (2013.01); *C12N 2830/50* (2013.01)

(58) Field of Classification Search
CPC .... C07K 14/80; A61K 48/0066; C12N 15/86; C12N 2750/14143; C12N 2830/48; C12N 2830/50
See application file for complete search history.

(56) References Cited

U.S. PATENT DOCUMENTS 11,078,247 B2 * 8/2021 Fotin-Mleczek .... C07K 14/505

FOREIGN PATENT DOCUMENTS

| CN | 109136266 A | 1/2019 |
|---|---|---|
| CN | 111630170 | 9/2020 |
| CN | 111733174 | 10/2020 |
| CN | 113106124 | 7/2021 |
| CN | 118028318 A | 5/2024 |
| JP | 2021-500917 A | 1/2021 |
| WO | 2019-025984 A1 | 2/2019 |
| WO | WO2019/025984 * | 2/2019 |
| WO | WO2020/174368 * | 9/2020 |
| WO | WO 2020/174368 A1 | 9/2020 |
| WO | WO 2020/174369 A2 | 9/2020 |

OTHER PUBLICATIONS

First Chinese Office Action with Search dated Jul. 5, 2024 for Chinese corresponding Application No. 202280050016.6 (18 pages including English Translation).
International Search Report issued Oct. 25, 2022, in PCT/CN2022/106089, filed Jul. 15, 2022.
"*Homo sapiens* cytochrome P450 family 4 subfamily V member 2 (CYP4V2), mRNA" NCBI Reference Sequence: NM_207352.4, Jun. 13, 2021 (Jun. 13, 2021).
Japanese Office Action Dec. 18, 2024, in Japanese Patent Application No. 2024-502112.
Supplementary European Search Report issued Feb. 24, 2025, in European Patent Application No. 22 84 1506.
Thilo M. Buck, et al., "Recombinant Adeno-Associated Viral Vectors (rAAV)-Vector Elements in Ocular Gene Therapy Clinical Trials and Transgene Expression and Bioactivity Assays", International Journal of Molecular Sciences, vol. 21, No. 12, Jun. 12, 2020, p. 4197.
J. Fraser Wright, "Codon Modification and PAMPs in Clinical AAV Vectors: The Tortoise or the Hare?", Molecular Therapy, vol. 28, No. 3, Mar. 1, 2020, pp. 701-703.
Ying Kai Chan, et al., "Engineering adeno-associated viral vectors to evade innate immune and inflammatory responses", Science Translational Medicine, vol. 13, No. 580, Feb. 10, 2021, 17 pages.

* cited by examiner

*Primary Examiner* — Quang Nguyen
(74) *Attorney, Agent, or Firm* — Merchant & Gould P.C.; Daniel J. Pereira

(57) ABSTRACT

The present disclosure provides a recombinant adeno-associated vector comprising a codon-optimized sequence encoding CYP4V2 linked to selected gene expression regulatory sequences and its use in treating Bietti Crystalline Dystrophy (BCD).

15 Claims, 10 Drawing Sheets

Specification includes a Sequence Listing.

SEQUENCE LISTING

```
Sequence total quantity: 36
SEQ ID NO: 1           moltype = DNA  length = 1578
FEATURE                Location/Qualifiers
source                 1..1578
                       mol_type = genomic DNA
                       organism = Homo sapiens
SEQUENCE: 1
atggcgggc tctggctggg gctcgtgtgg cagaagctgc tgctgtgggg cgcggcgagt   60
gcccttccc tggccggcgc cagtctggtc ctgagcctgc tgcagagggt ggcgagctac  120
gcgcggaaat ggcagcagat gcggcccatc cccacggtgg cccgcgccta cccactggtg  180
ggccacgcgc tgctgatgaa gccggacggg cgagaatttt ttcagcagat cattgagtac  240
acagaggaat accgccacat gccgctgctg aagctctggg tcgggccagt gcccatggtg  300
gcccttata atgcagaaaa tgtggaggta attttaacta gttcaaagca aattgacaaa  360
tcctctatgt acaagttttt agaaccatgg cttggcctag gacttcttac aagtactgga  420
aacaaatggc gctccaggag aaagatgtta acacccactt tccattttac cattctgaaa  480
gatttcttag atatcatgaa tgaacaagca aatatattgg ttaagaaact tgaaaaacac  540
attaaccaag aagcatttaa ctgcttttt tacatcatcc tttgtgcctt agatatcatc  600
tgtgaaacag ctatgggaa gaatattggt gctcaaagta atgatgattc cgagtatgtc  660
cgtgcagttt atagaatgag tgagatgata tttcgaagaa taaagatgcc ctggctttgg  720
cttgatctct ggtaccttat gtttaaagaa ggatgggaac acaaaaagag ccttcagatc  780
ctacatactt ttaccaacag tgtcatcgct gaacgggcca atgaaatgaa cgccaatgaa  840
gactgtagag gtgatggcag gggctctgcc ccctccaaaa ataaacgcag ggccttttct  900
gacttgcttt taagtgtgac tgatgacgaa gggaacaggc taagtcatga agatattcga  960
gaagaagtta acaccttcat gtttgagggg cacgatacaa ctgcagctgc aataaactgg 1020
tccttatacc tgttgggttc taaccagaa gtccagaaaa aagtggatca tgaattggat 1080
gacgtgtttg ggaagtctga ccgtcccgct acagtagaag acctgaagaa acttcggtat 1140
ctggaatgtg ttattaagga gacccttcgc ctttttcctt ctgttccttt atttgcccgt 1200
agtgttagtg aagattgtga agtggcaggt tacagagttc taaaaggcac tgaagccgtc 1260
atcattccct atgcattgca cagagatccg agatacttcc ccaaccccga ggagttccag 1320
cctgagcggt tcttccccga gaatgcacaa gggcgccatc catatgccta cgtgcccttc 1380
tctgctggcc ccaggaactg tataggtcaa aagtttgctg tgatggaaga aaagaccatt 1440
ctttcgtgca tcctgaggca cttttggata gaatccaacc agaaaagaga agagcttggt 1500
ctagaaggac agttgattct tcgtccaagt aatggcatct ggatcaagtt gaagaggaga 1560
aatgcagatg aacgctga                                                1578

SEQ ID NO: 2           moltype = DNA  length = 1578
FEATURE                Location/Qualifiers
source                 1..1578
                       mol_type = other DNA
                       organism = synthetic construct
SEQUENCE: 2
atggccggac tgtggctggg gctggtgtgg cagaagctgc tgctgtgggg ggccgccagc   60
gctctgtctc tggctggagc cagcctggtg ctgagcctgc tgcagagggt ggccagctac  120
gctagaaagt ggcagcagat gaggcccatc cccactgtgg cccgggccta ccctctggtg  180
ggacacgctc tgctgatgaa acccgatggc agagaattct tccagcagat tatcgagtat  240
accgaggaat acagacacat gccctgctg aaactgtggg tgggacctgt gcccatggtg  300
gccctgtaca acgccgagaa cgtggaagtg atcctgacca gcagcaagca gatcgacaaa  360
agcagcatgt acaaattcct ggaaccctgg ctgggactgg gactgctgac cagcactgga  420
aacaagtgga gaagcagaag aaagatgctg acccccacct tccacttcac catcctggag  480
gacttcctgg acatcatgaa cgaacaggcc aacatcctgg tgaaaagct ggaaaaacac  540
atcaaccagg aagccttcaa ctgcttcttc tacatccacc tgtgcgcccct ggacatcatc  600
tgcgaaaccg ccatgggaaa gaacatcggc gcccagagca acgacgacag cgaatacgtg  660
agaccgtgt atcggatgtc cgagatgatc ttcagaagaa tcaaatgcc ctggctgtgg  720
ctggacctgt ggtatctgat gttcaaggag ggctgggagc aagaagag cctgcagatc  780
ctgcatacct tcaccaacag cgtgatcgcc gaaagagcca cgagatgaa cgccaacgag  840
gactgccggg gagacgggag aggcagcgct cctagcaaaa acaaaagaag agccttcctg  900
gacctgctgc tgagcgtgac cgacgacgaa ggaaatagac tgagccacga agacatcaga  960
gaggaagtga acacattcat gttcgaaggc cacgacacaa cagccgccgc catcaactgg 1020
tccctgtacc tgctgggcag caaccccgag gtgcagaaga aggtggacca cgagctggac 1080
gacgtgtttg ggaagagcga cagacctgcc accgtggagg atctgaaaaa gctgagatat 1140
ctggagtgcg tgattaaaga gacctgaga ctgttccaa gtgtgcccct gttcgccaga 1200
tctgtgagtg aggactgcga ggtggccggc tatagagtgc tgaaaggaac cgaggccgtg 1260
```

```
attattccct acgccctgca cagggacccc aggtacttcc ccaaccccga ggaattccag    1320
cctgagagat tctttcccga gaatgctcag ggaagacacc cctacgccta tgtgcccttc    1380
agcgccggcc ccagaaactg cattggccag aagttcgccg tgatggagga aagaccatc    1440
ctgagctgca tcctgagaca cttttggatt gagagcaacc agaagcggga ggagctggga    1500
ctggaaggcc agctgatcct gagaccaagc aacggaatct ggatcaagct gaaaagaaga    1560
aacgccgacg agagatga                                                  1578

SEQ ID NO: 3           moltype = DNA  length = 1578
FEATURE                Location/Qualifiers
source                 1..1578
                       mol_type = other DNA
                       organism = synthetic construct
SEQUENCE: 3
atggccggac tgtggctggg cctggtgtgg cagaagctgc tgctgtgggg cgccgccagc    60
gctctgtctc tggctggagc ctccctggtg ctgagcctgc tgcagagggt ggcctcctac    120
gccagaaagt ggcagcagat gagggcccatc cccacagtgg ccaggcccta ccctctggtg    180
ggccacgctc tgctgatgaa gcctgacggc agggagtttt tccagcagat catcgagtac    240
accgaggagt acaggcacat gccccctgctg aagctgtggg tgggccccgc gcctatggtg    300
gccctgtaca atgccgagaa tgtggaggtc attctgacat cctccaagca gatcgataag    360
tcctccatgt acaagtttct ggagccttgg ctgggcctcg gctgctgac aagcacaggc     420
aataagtgga ggagcaggag aaagatgctg acccctacct ttcactttac aatcctggag    480
gacttttctgg atatcatgaa cgagcaggcc aacatcctgg tgaagaagct ggagaagcac   540
atcaaccagg aggccttcaa ttgtttcttt tacatcacac tgtgcgcccct ggacatcatc    600
tgcgagaccg ccatgggcaa gaatatcggc gcccagtcca acgacgattc cgagtacgtg    660
agggccgtgt acaggatgag cgagatgatc tttaggagaa tcaagatgcc ctggctgtgg    720
ctggacctgt ggtacctgat gtttaaggag ggctgggagc aacaagaagag cctgcagatc    780
ctgcacacat tcacaaaattc cgtgatcgcc gagagagcca acgagatgaa tgccaatgag    840
gactgtagag gcgatggcag gggctccgcc cctctaaga ataagaggag gcctttctg      900
gacctgctgc tgtccgtgac agatgacgag gcaataggc tgtcccacga ggatatcagg     960
gaggaggtgg acaccttcat gttttgagggc cacgacacaa cagccgccgc catcaactgg    1020
agcctgtacc tgctgggcag caatcccgag gtgcagaaga aggtggatca cgagctggat    1080
gatgtgttcg gcaagagcga cagacccgcc acagtggagg atctgaagaa gctgagatac    1140
ctggagtgcg tgatcaagga gacactgaga ctgtttccctt ccgtgcccct gttcgccaga    1200
agctgtgtccg aggactgtga ggtggccggc tacagagtgc tgaagggcac cgaaggccgtg   1260
atcatcccct acgccctgca cagggatcct agatacttcc ctaacccga ggagttccag     1320
cccgagaggt ttttccccga gaatgccag gcaggcacc cctacgccta cgtgcccttt      1380
agcgccggcc ctaggaactg tatcggccag aagtttgccg tgatggagga aagaccatc     1440
ctgtcctgca tcctgagaca cttctggatc gagtccaacc agaagaggga ggagctgggc    1500
ctggagggcc agctgatcct gagacctagc aacggcatct ggatcaagct gaagagaaga    1560
aatgccgatg agagatga                                                  1578

SEQ ID NO: 4           moltype = DNA  length = 1578
FEATURE                Location/Qualifiers
source                 1..1578
                       mol_type = other DNA
                       organism = synthetic construct
SEQUENCE: 4
atggctggac tttggctggg actggtgtgg caaaaactgc tgctgtgggg cgctgctagc    60
gccctgagcc tggctggagc ttctcttgtg ctgagcttac tgcaaagagt ggccagctat    120
gccagaaagt ggcagcagat gagacccatc ccaccgtgg ctagagctta tcctctggtg      180
ggacatgctc tgctgatgaa gcccgacgga agagagtttt tccagcagat catcgagtac    240
accgaggagt acagacacat gcccctgctg aagctgtggg tgggcccagt tcctatggtg    300
gctctgtata atgctgaaaa cgtggaggtg atcctgacca gcagcaagca gatcgacaag    360
agcagcatgt acaagttcct ggagccctgg ctgggcctgg attactgac atctacagga     420
aataaatgga gaagcagaag aaagatgctg acccccacct tccactttac catcctggag    480
gacttcctgg acatcatgaa cgagcaggcc aacatcctga tgaagaagct ggaagagcac   540
atcaaccagg aggccttcaa ctgcttcttc tacatcaccc tgtgcgccct ggacatcatc    600
tgcgagacag ctatgggcaa gaacatcggc gctcaaagca atgacgacag cgagtatgtg    660
agaccgtgt acagaatgag cgagatgatc ttcagaagaa tcaagatgcc ctggctgtgg    720
ctggacctgt ggtatctgat gttcaaggag ggctgggagc acaagaagat cctgcagatt    780
ctgcacacct tcaccaacag cgtgatcgcc gagagagcca acgagatgaa cgccaacgag    840
gactgcagag gcgacggcag aggatctgct cctagcaaaa ataagagaag agccttcctg    900
gacctgctgc tgagcgtgac agatgacgaa ggaaacagac tgagccacga ggacatcaga    960
gaggaggtgg acaccttcat gttcgagggc cacgacacca ccgccgctgc tattaattgg    1020
agcctgtatc tgctgggaag caaccccgaa gtgcaaaaga agtggaccac cgagctggac    1080
gacgtgttcg gcaaaagcga cagacccgcc acagtggagg atctgaaaaa gctgagatac    1140
ctggagtgcg tgatcaagga cccctgaga ctgttcccca gcgtgccct tttcgctaga     1200
tctgtgagcg aagattgcga ggtggccggc tatagagtgc tgaaaggcac cgaagccgtg    1260
atcatcccct acgctctgca cagagacccc agatacttcc ccaacccga ggagttccag    1320
cccgagagat ttttcccga aacgcccaa ggcagacacc cctatgctta tgtgcccttc     1380
agcgccggcc ccagaaattg cattggacaa aagttcgccg tgatggagga aagaccatc     1440
ctgagctgca tcctgagaca cttctggatc gagagcaacc agaagagaga ggagctgggc    1500
ctggagggcc aactgattct gagacctagc aacggcatct ggatcaagct gaagagaaga    1560
aacgccgacg agagatga                                                  1578

SEQ ID NO: 5           moltype = DNA  length = 1578
FEATURE                Location/Qualifiers
source                 1..1578
                       mol_type = other DNA
```

```
                        organism = synthetic construct
SEQUENCE: 5
atggcaggac tgtggctggg actggtgtgg cagaagctgc tgctgtgggg agcagcaagc   60
gccctgtccc tggcaggcgc ctccctggtg ctgtctctgc tgcagagggt ggcaagctac  120
gcaaggaagt ggcagcagat gcggcccatc cctaccgtgg caagagcata tccactggtg  180
ggacacgcac tgctgatgaa gcctgacggc cgcgagttct ttcagcagat catcgagtac  240
acagaggagt atcggcacat gccactgctg aagctgtggg tgggaccagt gccaatggtg  300
gccctgtaca cgccgagaa tgtggaagtg atcctgacca gctccaagca gatcgataag  360
tctagcatgt ataagttcct ggagccttgg ctgggactgc tgactgctgac ctccacaggc  420
aacaagtgga ggtctcggag aaagatgctg accccaacat tccactttac aatcctggag  480
gacttcctgg atatcatgaa cgagcaggcc aatatcctgg tgaagaagct ggagaagcac  540
atcaaccagg aggcctttaa ttgcttcttt tacatcaccc tgtgcgccct ggacatcatc  600
tgtgagacag ccatgggcaa gaacatcggc gcccagagca atgacgattc cgagtacgtg  660
agggccgtgt atcgcatgtc cgagatgatc tttaggcgca tcaagatgcc ctggctggtg  720
ctggatctgt ggtatctgat gttcaaggag ggctgggagc acaagaagag cctgcagatc  780
ctgcacacct ttacaaactc cgtgatcgcc gagcgggcca atgagatgaa cgccaatgag  840
gactgtaggg gcgatggaag aggctctgcc ctagcaagaa caagcggag agccttcctg  900
gacctgctgc tgtctgtgac cgacgatgag ggcaatagac tgagccacga ggacatcggg  960
gaggaggtgg atacattcat gtttgaggga cacgacacca cagcagcagc catcaactgg 1020
tctctgtacc tgctgggcag caatccagag gtgcagaaga ggtggatca cgagctggac 1080
gacgtgttcg gcaagagcga cagacccgcc accgtggagg atctgaagaa gctgaggtac 1140
ctggagtgcg tgatcaagga gacactgaga ctgttccccc ccgtgcctct gtttgccagg 1200
tccgtgtctg aggactgtga ggtgccggc tatcgcgtgc tgaagggcac cgaggccgtg 1260
atcatccctt acgccctgca ccgggacccc agatatttcc ctaacccaga ggagtttcag 1320
ccagagcggt tcttcccaga gaatgcacag ggccggcacc cttacgccta tgtgccattc 1380
tctgccggac caaggaactg catcggacag aagtttgatg tgatggagga agagaccatc 1440
ctgtcctgta tcctgcgcca cttctgggac gagtctaatc agaagaggga ggagtctggga 1500
ctggagggac agctgatcct gagaccctcc aacggcatct ggatcaagct gaagaggcgc 1560
aatgccgatg agaggtga                                               1578

SEQ ID NO: 6             moltype = DNA  length = 1578
FEATURE                  Location/Qualifiers
source                   1..1578
                         mol_type = other DNA
                         organism = synthetic construct
SEQUENCE: 6
atggctggac tgtggctcgg actggtgtgg cagaagctgc tgctgtgggg cgctgcctct   60
gccctcagtc tggctggagc cagcctggtc ctgtctctgc tccagagagt ggcttcttat  120
gccagaaagt ggcagcaaat gaggcctatc cctactgtgg ccagagcca ccctctggtt  180
ggacacgccc tgctgatgaa gcctgacggc agggagttct ttcagcagat aatcgaaac  240
actgaagaat acagacacat gcctctcctg aaactctggg tgggaccagt tcctatggtc  300
gccctgtaca tgccgagaa tgtcgaagtg atcctgacca gctcaaagca gattgataag  360
tctagcatgt acaagttcct ggagccctgg ctgggactgc tgctgctcac ctccaccggc  420
aataagtggc gctcaagaag gaagatgctc actccaacct tcacttttac cactactgga  480
gactttctcg acatcatgaa tgagcaagcc aacattctcg ttaagaagct ggagaaacac  540
ataaaccagg aggcttcaa ctgtttcttc tacataaccc tgtgcgctct ggacatcatc  600
tgcgaaaccg ctatgggcaa gaacataggg gcccaatcca atgacgattc tgagtacgtg  660
agggctgtct accgcatgtc tgagatgatc ttcagacgga ttaagatgcc ctggctgtgg  720
ctggatctgt ggtatctgat gttcaaggaa ggatgggagc acaagaagtc tctgcaaatc  780
ctccatacat tcactaacag tgtcattgct gaaagggcta acgagatgaa tgctaatgaa  840
gattcagag gagatggacg cggttccgca ccttccaaga acaagcgag agcatttctg  900
gatctcctgc tgagtgttac cgacgacgag ggcaaccggc tgtcccatga ggacatcagg  960
gaagaggtgg ataccttttat gtttcgagggc cacgatacca ccgcagctgc tatcaactgg 1020
tccctctatc tgctgggttc caaccctgaa gtgcagaaga aggttgacca cgaactcgat 1080
gacgtgtttg gtaagagcga cagacctgcc accgtcgagg acctgaagaa gctccgctac 1140
ctggagtgtg tgatcaagga gacactcagg ctgtttccta gcgtgcctct gttcgctagg 1200
tctgtctctg aggattgcga ggttgccgga tacagagtgc tcaaaggaac tgaggccgtc 1260
ataatccctt acgccctgca ccgcgaccct agatactttc ccaatccga ggagttccaa 1320
ccagagagat tcttccctga gaatgcccaa ggcaggcatc cttatgctta tgtcccattc 1380
tctgccggac ctaggaattg tattggacag aagttcgccg ttatggaaga agagacaatc 1440
ctgtcctgta tactgcgcca cttctggatc gagagcaatc agaagaggga ggaactcggc 1500
ctggaaggac agctcattct cagaccttca aacgggattt ggatcaaact caaacggaga 1560
aacgccgacg agaggtga                                               1578

SEQ ID NO: 7             moltype = DNA  length = 1578
FEATURE                  Location/Qualifiers
source                   1..1578
                         mol_type = other DNA
                         organism = synthetic construct
SEQUENCE: 7
atggctggtc tgtggctggg cctggtgtgg cagaagctgc tgctgtgggg agctgcctct   60
gctctgtccc tggctggtgc ctccctggtg ctgagcctgc tgcagagggt ggcctcctat  120
gctaggaagt ggcagcagat gaggcccatc cccacagtgg ccagggccta ccccctggtg  180
ggccatgctc tgctgatgaa gcctgatggc agggagttct tccagcagat cattgaaatc  240
acagaagagt acaggcacat gcctctgctg aagctgtggg tgggcccctgt tcctatggtc  300
gccctgtaca tgcctgagaa tgttgaggtc attctgacct cctccaagca gattgataag  360
tccagcatgt acaagtttct ggagccttgg ctgggcctgg tctgctgac atccacaggt  420
aataagtgga agcagaag gaagatgctg acacccacct ttacttcac aatcctggag  480
gacttcctgg atatcatgaa tgagcaggcc aacatcctgg tgaagaagct ggagaagcac  540
```

```
atcaatcagg aggccttcaa ctgcttttc tacatcaccc tgtgtgccct ggatatcatc   600
tgtgaaacag ctatgggcaa gaatattggt gcccagagca atgatgactc tgaatatgtt   660
agggctgttt acagaatgtc tgaaatgatc tttagaagga tcaagatgcc ttggctgtgg   720
ctggatctgt ggtacctgat gtttaaggag ggctgggagc acaagaagtc cctgcagatc   780
ctgcacacct ttaccaactc tgttattgct gagagagaca atgaaatgaa tgccaatgag   840
gactgcaggg gagatggcag aggctctgct ccttccaaga ataagagaag agccttcctg   900
gatctgctgc tgtctgttac agatgatgaa ggcaacaggc tgagccatga agacatcagg   960
gaggaggtgg atacattcat gtttgagggc catgatacca cagctgctgc tatcaactgg  1020
tccctgtacc tgctgggcag caaccctgag gtgcagaaga aggtggacca tgaactggat  1080
gatgttttg gcaagtctga tagacctgct acagttgagg acctgaagaa gctgaggtac  1140
ctggagtgtg tgatcaagga gacactgagg ctgtttcctt ctgttccct gtttgccaga  1200
tctgtttctg aagattgtga agtggctggt tacagggtgc tgaagggcac agaggctgtt  1260
atcatcccct atgctctgca cagagacccc agatactttc ctaatcctga ggagtttcag  1320
cctgaaaggt ttttccctga gaatgctcag ggcagacacc cctatgctta tgttccctc  1380
tctgctggcc ctaggaactg cattggtcag aagtttgctg tgatggagga gaagaccatc  1440
ctgagctgca tcctgagaca cttctggatt gaaagcaacc agaagaggga ggagctgggc  1500
ctggagggcc agctgatcct gaggccctcc aatggcatct ggatcaagct gaagagaaga  1560
aatgctgatg agagatga                                                1578

SEQ ID NO: 8             moltype = DNA   length = 1578
FEATURE                  Location/Qualifiers
source                   1..1578
                         mol_type = other DNA
                         organism = synthetic construct
SEQUENCE: 8
atggctggcc tgtggctggg gctggtctgg cagaagctgc tcctgtgggg ggctgcctcc    60
gccctctccc tggctggggc tagcctggtg ctgagcctgc tgcagagagt ggctagctat   120
gctagaaagt ggcagcagat gagacccatc cccacagtgg ctagagccta ccccctggtg   180
ggccatgccc tgctgatgaa gcctgatggc agagagttct ttcagcagat cattgagtac   240
acagaggagt acagacacat gcccctgctg aagctgtgga tgggccctgt gcctatggtg   300
gcactgtaca atgctgagaa tgtggaggtg atcctgacaa gcagcaagca gattgacaag   360
agcagcatgt acaagttcct ggagccctgg ctgggcctgg gctgctgac aagcaccggc   420
aacaagtgga gaagcagaag aaagatgctg acccccacct tccacttcac catcctggag   480
gacttcctgg acatcatgaa tgagcaagcc aacatcctgg tgaagaagct ggagaagcac   540
atcaaccaag aggccttcaa ctgcttcttc tacatcaccc tgtgtgccct ggacatcatc   600
tgtgagacag ccatgggcaa gaacattggg gctcagagca atgatgacag cgagtatgtg   660
agagctgtgt acagaatgag cgagatgatc ttcagaagaa tcaagatgcc ctggctgtgg   720
ctggacctgt ggtacctgat gttcaaggag ggctgggagc acaagaagag cctgcagatc   780
ctgcacacct tcaccaacag cgtgattgct gagagagaca atgaagcaga tgccaatgag   840
gactgcagag gggatggcag aggcagcgcc cctagcaaga acaagagaag agccttcctg   900
gacctgctcc tgagcgtgac agatgatgag ggcaacagac tgagccatga ggacatcaga   960
gaaaggtgg acaccttcat gtttgagggc catgacacca cagctgctgc catcaactgg  1020
agcctgtacc tgctgggcag caaccctgag gtgcagaaga aggtggacca tgagctggat  1080
gatgtgtttg gcaagagcga cagacctgcc acagtggagg acctgaagaa gctgagatac  1140
ctggagtgtg tgatcaagga ccctgaga ctgttcccca gcgtgccct gtttgctaga  1200
agcgtgagcg aggactgtga ggtggctggc tacagagtgc tgaagggcac agaggctgtg  1260
atcatcccct atgccctgca cagagacccc agatacttc ccaacctga ggagtttcag  1320
cctgagagat tcttccctga gaatgcccaa ggcagacacc cctatgccta tgtgcccttc  1380
agcgctggcc ctagaaactg cattgggcag aagtttgctg tgatggagga gaagaccatc  1440
ctgagctgca tcctgagaca cttctggatt gagagcaatc agaagagaga ggagctgggc  1500
ctggaggggc agctgatcct gagacctagc aatggcatct ggatcaagct gaagagaaga  1560
aatgctgatg agagatga                                                1578

SEQ ID NO: 9             moltype = DNA   length = 1578
FEATURE                  Location/Qualifiers
source                   1..1578
                         mol_type = other DNA
                         organism = synthetic construct
SEQUENCE: 9
atggctggcc tgtggctggg cctggtgtgg cagaagctgc tgctgtgggg agctgccagt    60
gccctgagcc tggctggggc cagcctggtg ctgagcctgc tgcagagggt ggccagctat   120
gccaggaagt ggcagcagat gaggcccatc cccacagtgg ccagggccta ccccctggtg   180
ggccatgccc tgctgatgaa gcctgatggc agggagttct ccagcagat cattgagtac   240
acagaggagt acaggcacat gcccctgctg aagctgtgga tgggccctgt ccctatggtg   300
gccctgtaca atgctgagaa tgtggaggtg atcctgacca gcagcaagca gattgacaag   360
agcagcatgt acaagttcct ggagccctgg ctgggcctgg gctgctgac cagcacaggc   420
aacaagtgga ggagcaggag gaagatgctg acccccacct tccacttcac catcctggag   480
gacttcctgg acatcatgaa tgagcaggcc aacatcctgg tgaagaagct ggagaagcac   540
atcaaccagg aggccttcaa ctgcttcttc tacatcaccc tgtgtgccct ggacatcatc   600
tgtgagacag ccatgggcaa gaacattgga gcccagagca atgatgacag tgagtatgtg   660
agggctgtgt acaggatgag tgagatgatc ttcaggagga tcaagatgcc ctggctgtgg   720
ctggacctgt ggtacctgat gttcaaggag ggctgggagc acaagaagag cctgcagatc   780
ctgcacacct tcaccaacag tgtgattgct gagggccaa tgagatgaa tgccaatgag   840
gactgcaggg gagatggcag aggcagtgcc cccagcaaga acaagagaag agccttcctg   900
gacctgctgc tgagtgtgac agatgatgag ggcaacaggc tgagccatga ggacatcagg   960
gaggaggtgg acaccttcat gtttgagggc catgacacca cagctgcagc tatcaactgg  1020
agcctgtacc tgctgggcag caaccctgag gtgcagaaga aggtggacca tgagctggat  1080
gatgtgtttg gcaagagtga caggcctgcc acagtggagg acctgaagaa gctgaggtac  1140
ctggagtgtg tgatcaagga ccctgagg ctgttcccca gtgtgcccct gtttgccagg  1200
```

```
agtgtgtctg aggactgtga ggtggctggc tacagggtgc tgaagggcac agaggctgtg   1260
atcatcccct atgccctgca cagggacccc aggtacttcc ccaaccctga ggagttccag   1320
cctgagaggt tcttccctga gaatgcccag ggcaggcacc cctatgccta tgtgcccttc   1380
agtgctggcc ccaggaactg cattggccag aagtttgctg tgatggagga aagaccatc    1440
ctgagctgca tcctgaggca cttctggatt gagagcaacc agaagaggga ggagctgggc   1500
ctggagggcc agctgatcct gaggcccagc aatggcatct ggatcaagct gaagaggagg   1560
aatgctgatg agaggtga                                                 1578

SEQ ID NO: 10          moltype = DNA  length = 1578
FEATURE                Location/Qualifiers
source                 1..1578
                       mol_type = other DNA
                       organism = synthetic construct
SEQUENCE: 10
atggctggcc tgtggctggg gctggtctgg cagaagctgc tcctgtgggg ggctgcctca    60
gccctctccc tggctggggc tagcctggtg ctgagcctgc tgcagagagt ggctagctat   120
gctagaaagt ggcagcagat gagacccatc cccacagtgg ctagagccta cccctggta   180
ggccatgccc tgctgatgaa gcctgatggc agagagttct ttcagcagat cattgagtac   240
acagaggagt acagacacat gcccctgctg aagctgtggg tgggccctgt gcctatggta   300
gcactgtaca atgctgagaa tgtggaggtg atcctgacaa gcagcaagca gattgacaag   360
agcagcatgt acaagttcct ggagccctgg ctgggcctgg gctgctgac aagcactggc    420
aacaagtgga gaagcagaag aaaagtgctg accccctcac catcctggag               480
gacttcctgg acatcatgaa tgagcaagcc aacatcctgg tgaagaagct ggagaagcac   540
atcaaccaag aggccttcaa ctgcttcttc tacatcaccc tgtgtgccct ggatatcatc   600
tgtgagacag ccatgggcaa gaacattggg gctcagagca atgatgacag tgagtatgtg   660
agagctgtgt acagaatgag tgagatgatc ttcagaagaa tcaagatgcc ctggctgtgg   720
ctggacctgt ggtacctgat gttcaaggag ggctgggagc acaagaagaa cctgcagatc   780
ctgcacacct tcaccaactc tgtgattgct gagagagcca tgagatgaa tgccaatgag    840
gactgcagag ggatggcag aggcagtgcc cctagcaaga caagagaag agccttcctg     900
gacctgctcc tgtcagtgac agatgatgag ggcaacagac tggacatcga ggacatcaga   960
gaagaggtgg acaccttcat gtttgagggc catgacacca cagctgctgc catcaactgg  1020
agcctgtacc tgctgggcag caaccctgag gtgcagaaga aggtggacca tgagctggat  1080
gatgtgtttg gcaagagtga cagacctgcc acagtggagg acctgaagaa gctgagatac  1140
ctggagtgtg tgatcaagga gaccctgaga ctgttccccct cagtgcccct gtttgctaga  1200
agtgtgtctg aggactgtga ggtggctggc tacagagtgc tgaagggcac agaggctgtg  1260
atcatcccct atgccctgca cagagaccct agatacttcc ccaaccctga ggagtttcag  1320
cctgagagat tcttccctga gaatgcccaa ggcagacacc cctatgccta tgtgcccttc  1380
agtgctggcc ctagaaactg cattgggcag aagtttgctg tgatggagga aagaccatc   1440
ctgagctgca tcctgagaca cttctggatt gagagcaatc agaagagaga ggagctgggc  1500
ctggagggcc agctgatcct gagacctagc aatggcatct ggatcaagct gagagaaga   1560
aatgctgatg agagatga                                                1578

SEQ ID NO: 11          moltype = DNA  length = 1578
FEATURE                Location/Qualifiers
source                 1..1578
                       mol_type = other DNA
                       organism = synthetic construct
SEQUENCE: 11
atggctggac tgtggctggg cctggtgtgg cagaagctgc tgctgtgggg agctgccagt    60
gctctgtctc tggctggagc ctccctggtg ctgagcctgc tgcagagggt ggcctcctat   120
gccagaaagt ggcagcagat gagcccatc cccacagtgg ccagggccta ccctctggta   180
ggccatgctc tgctgatgaa gcctgatggc agggagtttt tccagcagat cattgagtac   240
acagaggagt acaggcacat gcccctgctg aagctgtggg tgggccctgt gcctatggtg   300
gccctgtaca atgctgagaa tgtggaggtc attctgacat cctccaagca gattgataag   360
tcctccatgt acaagtttct ggaccctggg ctgggcctgg gcctgctgac aagcacaggc   420
aataagtgga ggagcaggag aaagatgctg acccctacct ttcactttac aatcctggag   480
gactttctgg atatcatgaa tgagcaggcc aacatcctgg tgaagaagct ggagaagcac   540
atcaaccagg aggccttcaa ttgtttcttc tacatcacac tgtgtgccct ggacatcatc   600
tgtgagacag ccatgggcaa gaatattgga gcccagtcca atgatgattc tgagtatgtg   660
agggctgtgt acaggatgag tgagatgatc tttaggagaa tcaagatgcc ctggctgtgg   720
ctggacctgt ggtacctgat gtttaaggag ggctgggagc acaagaagag cctgcagatc   780
ctgcacacat tcacaaattc tgtgattgct gagagagcca tgagatgaa tgccaatgag    840
gactgtagag agatggcag ggctctgcc cctctaaga taagaggag gccttcctg         900
gacctgctcc tgtctgtgac agatgatgag ggcaataggc tgtcccatga ggatatcagg   960
gaggaggtgg acaccttcat gtttgagggc catgacacaa cagctgctgc catcaactgg  1020
agcctgtacc tgctgggcag caatcctgag gtgcagaaga aggtggatca tgagctggat  1080
gatgtgtttg gcaagagtga cagacctgcc acagtggagg atctgaagaa gctgagatac  1140
ctggagtgtg tgatcaagga cacactgaga ctgttccctt ctgtgcccct gtttgccaga  1200
agtgtgtctg aggactgtga ggtggctggc tacagatgtc tgaagggcac agaggctgtg  1260
atcatcccct atgccctgca cagggatcct agatacttcc ctaaccctga ggagttccag  1320
cctgagaggt tcttccctga gaatgcccag ggcaggcacc cctatgccta tgtgcccttc  1380
agtgctggcc ctaggaactg tattggccag aagtttgctg tgatggagga aagaccatc   1440
ctgtcctgca tcctgagaca cttctggatt gagtccaacc agaagaggga ggagctgggc  1500
ctggagggcc agctgatcct gagacctagc aatggcatct ggatcaagct gagagaaga   1560
aatgctgatg agagatga                                                1578

SEQ ID NO: 12          moltype = DNA  length = 1578
FEATURE                Location/Qualifiers
source                 1..1578
```

```
                    mol_type = other DNA
                    organism = synthetic construct
SEQUENCE: 12
atggcaggac tgtggctggg actggtgtgg cagaagctgc tgctgtgggg agcagcaagt    60
gccctgtccc tggcaggagc ctccctggtg ctgtctctgc tgcagagggt gccaagctat   120
gcaaggaagt ggcagcagat gaggcccatc cctacagtgg caagagcata tccactggtg   180
ggacatgcac tgctgatgaa gcctgatggc agggagttct ttcagcagat cattgagtac   240
acagaggagt ataggcacat gccactgctg aagctgtggg tgggaccagt gccaatggtg   300
gccctgtaca atgctgagaa tgtggaagtg atcctgacca gctccaagca gattgataag   360
tctagcatgt ataagttcct ggagccttgg gactgctgac ctccacaggc                420
aacaagtgga ggtctaggag aaagatgctg accccaacat tccactttac aatcctggag   480
gacttcctgg atatcatgaa tgagcaggcc aatatcctgg tgaagaagct ggagaagcac   540
atcaaccagg aggcctttaa ttgcttcttc tacatccacc tgtgtgccct ggacatcatc   600
tgtgagacag ccatgggcaa gaacattgga gcccagagca atgatgattc tgagtatgtg   660
agggctgtgt ataggatgtc tgagatgatc tttaggagga tcaagatgcc ctggctgtgg   720
ctggatctgt ggtatctgat gttcaaggag ggctgggagc acaagaagag cctgcagatc   780
ctgcacacct tcacaaactc tgtgattgct gagagggcca tgagatgaa tgccaatgag    840
gactgtaggg gagatggaag aggctctgcc cctagcaaga acaagaggag agccttcctg   900
gacctgctgc tgtctgtgac agatgatgag ggcaatagac tgagccatga ggacatcagg   960
gaggaggtgg atacattcat gtttgaggga catgacacca cagcagcagc catcaactgg  1020
tctctgtacc tgctgggcag caatccagag gtgcagaaga aggtggatca tgagctggat  1080
gatgtgtttg gcaagagtga cagacctgcc acagtggaga atctgaagaa gctgaggtac  1140
ctggagtgtg tgatcaagga gacactgaga ctgttcccct ctgtgcctct gtttgccagg  1200
tctgtgtctg aggactgtga ggtgctggc tatagggtgc tgaagggcac agaggctgtg   1260
atcatccctt atgccctgca cagggacccc agatatttcc ctaacccaga ggagtttcag  1320
ccagaggt tcttcccaga gaatgcacag ggcaggcacc cttatgccta tgtgccattc    1380
tctgctggac caaggaactg cattggacag aagtttgctg tgatggagga gaagaccatc  1440
ctgtcctgta tcctgaggca cttctggatt gagtctaatc agaagaggga ggagctggga  1500
ctggagggac agctgatcct gagaccctcc aatggcatct ggatcaagct gaagaggagg  1560
aatgctgatg agaggtga                                                 1578

SEQ ID NO: 13           moltype = DNA   length = 1578
FEATURE                 Location/Qualifiers
source                  1..1578
                        mol_type = other DNA
                        organism = synthetic construct
SEQUENCE: 13
atggctgggc tgtggctggg gctggtgtgg cagaagctgc tgctgtgggg agctgctagt    60
gccctcagcc tggctggagc aagcctggtg ctgagtctcc tgcagagagt ggcctcctat   120
gccaggaagt ggcaacagat gaggcccatc ccaacagtgg ctagagcata cccactggtg   180
ggccatgcct tgctgatgaa gcctgatggc agggagttct ttcagcagat cattgaatac   240
actgaggagt acagacacat gcctctgctg aagctgtggg tgggcccagt gcctatggtg   300
gccctctaca atgctgagaa tgtggaagtg attctgacca gcaagcaagc gattgataag   360
agtagcatgt acaagttcct ggagccctgg ctggggttag gcctgctgac cagcacagga   420
aacaagtgga ggagtaggag aaagatgctg accccaccct tccactttca catcctggag   480
gactttctgg atattatgaa tgaacaggca acatcttgg tgaagaagct ggagaagcac    540
attaatcagg aggccttcaa ctgcttcttc tatattaccc tgtgtgccct gggatatcatc   600
tgtgagacag ccatgggaaa gaatattgga gcccagagta atgatgactc tgagtatgtg   660
agggctgtgt acagaatgag tgagatgatc ttcaggagaa tcaagatgcc atggctgtgg  720
ctggacctgt ggtacctgat gttcaaggag ggtgggagc acaagaagtc cctgcagatt    780
ctgcacacct ttaccaacag tgtgattgct gagagggcca tgagatgaa tgccaatgag    840
gattgcaggg gagatggaag aggctctgcc cccagcaaga acaaaagaag ggccttcctg   900
gacctgctgt tgtctgtgac tgatgatgaa gggaacaggc tgtcacatga ggacatcaga   960
gaggaggtgg acaccttcat gtttgagggc catgacacca cagctgctgc cattaactgg  1020
agcctgtacc tgctgggaag caacccagag gtgcagaaga aggtggacca tgagctggat  1080
gatgtgtttg gcaagtcaga caggcctgcc acagtggagg acctgaagaa gctgaggtac  1140
ctggagtgtg tgatcaagga aacactgagg ctgttcccaa gtgtgcctct gtttgccagg  1200
tctgtgtcag aggactgtga agtggctggc tacagggtgc tgaagggaac agaggcagtg  1260
atcccat atgcactgca cagggaccct aggtattttc ctaaccctga ggagttccag     1320
ccagagaggt tctttcctga gaatgctcag ggcaggcatc cttatgccta tgtgcctttc   1380
tctgctggcc ccaggaactg cattggcacag aagtttgctg tgatgaaga gaagaccatt    1440
ttgtcctgta ttctgaggca cttctggatt gaatccaacc agaagaggga ggagctgggc  1500
ctggaagggc agctgatcct gaggccctcc aatggcattt ggatcaaact gaagaggaga  1560
aatgctgatg agagatga                                                 1578

SEQ ID NO: 14           moltype = DNA   length = 1578
FEATURE                 Location/Qualifiers
source                  1..1578
                        mol_type = other DNA
                        organism = synthetic construct
SEQUENCE: 14
atggctggcc tgtggctggg cctggtgtgg cagaagctgc tcctgtgggg agctgcctct    60
gccctgtccc tggctggggc tagcctggtg ctgtctctgt gcagagagt ggccagctat    120
gccaggaagt ggcaacagat gagacccatc cccacagtgg caagcata ccccctggtg     180
ggccatgcct tgctgatgaa gcctgatggc agagagttct ccagcagat cattgagtac    240
acagaggaat acagacacat gcctctgctg aagctgtggg tgggcccgt gcctatggtg    300
gctctctaca atgctgagaa tgtggaagtg atcctgacca gcagcaagca gattgacaag   360
tctagcatgt acaagttcct ggagccttgg ctgggactgg gactgctgac cagcacaggc   420
aacaagtgga ggagcagaag aaagatgctg acacctacct tccactttac catcctggaa  480
```

-continued

```
gatttcctgg acattatgaa tgagcaggcc aacatcctgg tcaagaagct ggaaaagcac    540
atcaaccagg aggcttttaa ctgcttcttc tacatcaccc tgtgtgccct ggacatcatc    600
tgtgagacag ccatgggcaa gaacattgga gctcagagca atgatgatag tgaatatgtt    660
agagctgtct acaggatgag tgagatgatc ttcaggagaa tcaagatgcc ctggctgtgg    720
ctggatctgt ggtacctgat gttcaaggaa ggatgggagc acaagaaaag cctgcagatc    780
ctgcacacct tcaccaacag tgtgattgct gagagagcca atgagatgaa tgccaatgag    840
gactgtagag gagatggcag gggcagtgcc ccttctaaga acaagagaag ggccttcctg    900
gacctgctgc tgagtgttac agatgatgag ggcaatagac tgtctcatga ggatatcaga    960
gaagaggtgg acaccttcat gtttgagggc catgacacta cagctgctgc tattaactgg   1020
tccctgtacc tgctgggcag caaccctgaa gtgcagaaga aggtggacca tgagctggat   1080
gatgtgtttg gaaagagtga tagacctgcc acagtggaag acctgaagaa gctaaggtac   1140
ctggagtgtg tgatcaagga aacactgaga ctgttccct ctgtgcctct gtttgccaga   1200
agtgtgtctg aggattgtga ggtggctggc tacagggtgc tgaagggcac agaggctgtg   1260
atcatccctt atgctctgca cagggaccc agatatttcc ctaaccctga ggagttccag   1320
cctgagaggt tcttcccaga gaatgcccag ggcagacatc cttatgccta tgtgccattc   1380
agtgctggtc ctagaaactg cattggccag aagtttgctg tgatgaaga gaagaccatc   1440
ctgagctgca tcctgaggca cttctggatt gagtctaatc agaagagaga ggaactgggc   1500
ctggaaggcc agctgatcct caggccaagc aatggcatct ggatcaagct gaagaggagg   1560
aatgctgatg agaggtga                                                 1578
```

SEQ ID NO: 15          moltype = DNA  length = 1578
FEATURE                Location/Qualifiers
source                 1..1578
                       mol_type = other DNA
                       organism = synthetic construct
SEQUENCE: 15
```
atggctggac tgtggctggg actggtgtgg cagaaactgc tgctttgggg agctgcctct     60
gctctgtctc ttgctggtgc ttctctggtg ctgagcctgc tgcagagagt ggcctcttat    120
gccagaaagt ggcagcagat gaggcccatt cctacagtgg ccagagccta tcctcttgtg    180
ggacatgccc tgctgatgaa gcctgatggc agagagttct tccagcagat cattgagtac    240
acagaggaat acaggcacat gccccctgctc aagctgtggg ttggacctgt gcctatggtg    300
gccctgtaca atgctgagaa tgtggaagtg atcctgacca gcagcaagca gattgacaag    360
tccagcatgt acaagtttct ggaaccctgg ctgggcctgg gctgctgac atctactgga    420
aacaagtgga ggagcaggag gaagatgctg accccctacc tccactttac aattctggag    480
gacttcctgg acatcatgaa tgagcaggcc aacatcctgg tcaagaagct ggaaaagcac    540
atcaatcaag aggccttcaa ctgcttcttc tacatcaccc tgtgtgccct ggatatcatc    600
tgtgagacag ccatgggcaa gaacattgga gcccagagca atgatgatag tgaatatgtg    660
agggctgtgt acaggatgag tgagatgatc ttcaggagga tcaagatgcc ttggctgtgg    720
ctggacctgt ggtatctgat gttcaaagaa ggctgggagc acaagaagtc cctgcagatc    780
ctgcacacct tcaccaacag tgtgattgct gagagggcca atgagatgaa tgccaatgaa    840
gattgcagag agatggcag gggaagtgcc cctagcaaga acaagagaag ggccttcctg    900
gatctgctgc tgagtgtgac agatgatgag ggcaatagac tgagccatga ggacatcaga    960
gaagaggtgg acaccttcat gtttgagggc catgacacaa cagctgctgc catcaattgg   1020
agcctgtacc tgctgggcag caaccctgag gtgcagaaga aggtggacca tgagctggat   1080
gatgtgtttg gcaagtctga tagacctgcc acagtggaag atctgaagaa gctgagatac   1140
ctggaatgtg tgatcaaaga gacactgagg ctgttcccta gtgtgcccct gtttgccaga   1200
agtgtgtctg aggattgtga agtggctggc tacagagtgc tgaagggcac agaggctgtg   1260
atcatcccct atgctctgca cagagatccc aggtacttcc ccaatcctga gagttccag   1320
cctgagaggt tcttcccaga gaatgcccag ggcagacacc cctatgccta tgtgccattc   1380
tctgctggac ctaggaactg cattggccag aagtttgctg tgatgaaga gaaaaccatc   1440
ctgagctgta tcctgaggca cttctggatt gagagcaacc agaagagaga ggaactgggc   1500
ctggagggac agctgattct gaggcctagc aatggcatct ggatcaagct gaagaggaga   1560
aatgctgatg agaggtga                                                 1578
```

SEQ ID NO: 16          moltype = DNA  length = 1578
FEATURE                Location/Qualifiers
source                 1..1578
                       mol_type = other DNA
                       organism = synthetic construct
SEQUENCE: 16
```
atggctggac tttggctggg actggtgtgg cagaagctgc tgctgtgggg agctgctagt     60
gccctgagcc tggctggagc ttctctttgtg ctgagcttac tgcaaagagt ggccagctat    120
gccagaaagt ggcagcagat gagacccatc cccacagtgg ctagagctta tcctctggtg    180
ggacatgctc tgctgatgaa gcctgatgga agagagtttt tccagcagat cattgagtac    240
acagaggagt acagacacat gccccctgct aagctgtggg tgggcccagt tcctatggtg    300
gctctgtata atgctgagaa tgtggaggtg atcctgacca gcagcaagca gattgacaag    360
agcagcatgt acaagttcct ggagccctgg ctgggcctgg gattactgac atctacagga    420
aataaatgga agcagaaag aaagatgctg acccccacct tccactttca catcctggag    480
gacttcctgg acatcatgaa tgagcaggcc aacatcctgg tcaagaagct ggaagagcac    540
atcaaccagg aggccttcaa ctgcttcttc tacatcaccc tgtgtgccct ggacatcatc    600
tgtgagacag ctatgggcaa gaacattgga gctcagagca atgatgacag tgagtatgtg    660
agagctgtgt acagaatgag tgagatgatc ttcagaagaa tcaagatgcc ctggctgtgg    720
ctggacctgt ggtatctgat gttcaaggag gctgggagc acaagaagag cctgcagatc    780
ctgcacacct tcaccaacag tgtgattgct gagagagcca atgagatgaa tgccaatgaa    840
gactgcagag agatggcag aggatctgct cctagcaaaa ataagagaag agccttcctg    900
gacctgctgc tgagtgtgac agatgatgaa ggaaacagac tgagccatga ggacatcaga    960
gaggaggtgg acaccttcat gtttgagggc catgacacca cagctgctgc tattaattgg   1020
agcctgtatc tgctggaag caaccctgaa gtgcagaaga aggtggacca tgagctggat   1080
gatgtgtttg gcaagagtga cagacctgcc acagtggagg atctgaagaa gctgagatac   1140
```

```
ctggagtgtg tgatcaagga gaccctgaga ctgttcccca gtgtgcccct gtttgctaga    1200
tctgtgagtg aagattgtga ggtggctggc tatagagtgc tgaaaggcac agaagctgtg    1260
atcatcccct atgctctgca cagagacccc agatacttcc ccaaccctga ggagtttcag    1320
cctgagagat tcttccctga gaatgcccaa ggcagacacc cctatgctta tgtgcccttc    1380
agtgctggcc ccagaaattg cattggacag aagtttgctg tgatggagga gaagaccatc    1440
ctgagctgca tcctgagaca cttctgggatt gagagcaacc agaagagaga ggagctgggc    1500
ctggagggcc aactgattct gagacctagc aatggcatct ggatcaagct gaagagaagg    1560
aatgctgatg agagatga                                                  1578

SEQ ID NO: 17           moltype = DNA   length = 1578
FEATURE                 Location/Qualifiers
source                  1..1578
                        mol_type = other DNA
                        organism = synthetic construct
SEQUENCE: 17
atggctggac tgtggctggg actggtgtgg cagaaactgc tgctgtgggg agctgcttct     60
gcactgtctc tggctgggc atctctggtc ctgtccctgc tgcagagagt ggcctcctat    120
gccagaaagt ggcagcagat gagacctatc cccacagtgg ccaggagcata ccccctggtg    180
ggtcatgccc tcctgatgaa accagatggg agggaatttt tccagcagat tattgagtac    240
acagaagaat atagacacat gcccctcctc aagctgtggg ttgggcctgt ccctatggtt    300
gccctctata atgctgagaa tgttgaagtt attctcacat catctaagca gattgataag    360
agtagcatgt ataagtttct ggaaccctgg ctggggctgg ggctcctcac ctcaactggg    420
aacaagtgga ggtctagaag aaaaatgctc accccccacct tccatttcac catcctggaa    480
gactttctgg acatcatgaa tgagcaggct aacatcctgg ttaaaaaact ggagaaacat    540
atcaatcagg aagccttcaa ttgtttcttc tatattactc tctgtgctct ggacattatc    600
tgtgagactg caatgggaaa gaatattggt gcacagtcaa atgatgattc agatatgtc    660
agggctgtct acagaatgtc tgagatgatc tttaggagaa tcaagatgcc ctggctgtgg    720
ctggatctgt ggtacctcat gttcaaggaa ggatgggagc ataagaaaag tctgcagatt    780
ctgcatacct tcaccaactc agtgattgca gagagagcaa atgagatgaa tgctaatgaa    840
gattgcaggg gggatggaag gggaagtgcc cctagcaaaa taagagaagg ggcctttctg    900
gatctcctcc tgagtgttac agatgatgag ggtaatagac tcagccatga agatatcaga    960
gaagaggtgg acacattcat gtttgagggc catgatacta ctgcagcagc tattaactgg   1020
agtctgtacc tgctgggctc aaaccctgag gttcagaaga agttgacca tgaactggat   1080
gatgtctttg ggaagtcaga caggcctgct actgtggaaga atctgaagaa agctgaggtac   1140
ctggagtgcg tcattaagga aacctgaga ctcttcccct ctgtccccct gtttgctaga   1200
tcagtttcag aagattgtga ggtggctggc tataggtgtcc tgaagggtac tgaggcagtg   1260
attatccctt atgctctcca cagggatcct aggtactttc caaatcctga ggagttccag   1320
cctgagagat tttccccaga aaatgcccag gcaggcatc cctatgctta tgtcccctttc   1380
agtgcaggac caagaaactg tattggccag aaatttgcag tcatggagga gaaaacaatc   1440
ctgtcttgca tcctgaggca ttttctggatt gaatccaacc agaaaagaga ggagctggga   1500
ctggaagggc agctgattct gagaccaagc aatgggattt ggatcaagct gaagaggagg   1560
aatgcagatg agaggtaa                                                 1578

SEQ ID NO: 18           moltype = DNA   length = 4325
FEATURE                 Location/Qualifiers
source                  1..4325
                        mol_type = other DNA
                        organism = synthetic construct
SEQUENCE: 18
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gactcgagac gcgttgacat tgattattga ctagttatta    180
atagtaatca attacggggt cattagttca tagcccatat atggagttcc gcgttacata    240
acttacggta aatggcccgc ctggctgacc gcccaacgac ccccgcccat tgacgtcaat    300
aatgacgtat gttcccatag taacgccaat agggactttc cattgacgtc aatgggtgga    360
ctatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatgggtcg    540
aggtgagccc cacgttctgc ttcactctcc ccatctcccc ccctccccac ccccaattt    600
tgtatttatt tattttttaa ttattttgtg cagcgatggg ggcgggggg gggggggcgc    660
gcgccaggcg gggcggggcg gggcgagggg cgggcggggc gaggcggag aggtgcggcg    720
gcagccaatc agagcggcgc gctccgaaag tttccttta tggcgaggcg gcggcggcgg    780
cggccctata aaagcgaag gcgcggcgg gcgggagtcc ctgcgttgcc ttcgccccgt    840
gccccgctcc gcgccgcctc gcgccgcccg ccccgcctcc gactgaccgc gttactccca    900
caggtgagcg ggcgggacgg cccttctcct ccgggctgta attagcgctt ggtttaatga    960
cggctcgttt cttttctgtg gctgcgtgaa agccttaaag ggctccggga gggccctttg   1020
tgcgggggg agcggctcgg ggggtgcgtg cgtgtgtgtg tgcgtgggga gccgccgcgtg   1080
cggccccgc tgcccggcgg ctgtgagcgc tgcgggcgcg gcgcgggct tgtgcgctc    1140
cgcgtgtgcg cgaggggagc gcggccgggg cggtgccc cggtgccgcga ctgcagccga   1200
ggggaacaaa ggctgcgtgc ggggtgtgtg cgtgggggg tgagcagggg gtgtgggcgc    1260
ggcggtcggg ctgtaacccc ccctgcacc ccctccccg agttgctgag cacggcccgg    1320
cttcgggtgc ggggctccgt acgggcgtg gcgcggggct cgccgtgccg ggcggggggt    1380
ggcggcaggt gggggtgccg gcggggcgg gccgcctcg ggccgggag ggctcggggg    1440
aggggcggg cggccccgg agccggccgc gctgtcgagg cgcggcgagc cgcagccatt    1500
gccttttatg gtaatcgtgc gagagggcgc agggacttcc tttgtcccaa atctgtgcgg   1560
agccgaaatc tgggaggcgc cgccgcaccc cctctagcgg gcgcggggcg aagcggtgcg   1620
gcgccggcag gaaggaaatg ggcggggagg gccttcgtgc gtcgccgcgc cgccgtcccc   1680
ttctccatct ccagcctcgg ggctgtccgc aggggggacgg ctgccttcgg ggggacgg   1740
gcagggcggg gttcggcttc tggcgtgtga ccggcggctc tagtgcctct gctaaccatg   1800
```

```
ttcatgcctt cttctttttc ctacagctcc tgggcaacgt gctggttatt gtgctgtctc   1860
atcattttgg caaaaagctt gccaccatgc cggggctctg gctggggctc gtgtggcaga   1920
agctgctgct gtggggcgcg cgagtgccc tttccctggc cggcgccagt ctggtcctga   1980
gcctgctgca gagggtggcg agctacgcgc ggaaatggca gcagatgcgg cccatcccca   2040
cggtgcccg cgcctaccca ctggtgggcc acgcgctgct gatgaagccg gacgggcgag   2100
aattttttca gcagatcatt gagtacacag aggaataccg ccacatgccg ctgctgaagc   2160
tctgggtcgg gccagtgccc atggtggccc tttataatgc agaaaatgtg gaggtaattt   2220
taactagttc aaagcaaatt gacaaatcct ctatgtacaa gtttttagaa ccatggcttg   2280
gcctaggact tcttacaagt actggaaaca aatggcgctc caggagaaag atgttaacac   2340
ccactttcca ttttaccatt ctggaagatt tcttagatat catgaatgaa caagcaaata   2400
tattggttaa gaaacttgaa aaacacatta accaagaagc atttaactgc tttttttaca   2460
tcactctttg tgcctagat atcatctgtg aaacagctat ggggaagaat attggtgctc   2520
aaagtaatga tgattccgag tatgtccgtg cagtttatag aatgagtgag atgatatttc   2580
gaagaataaa gatgccctgg cttttggcttg atctctggta cctatgttt aaagaaggat   2640
gggaacacaa aaagagcctt cagatcctac atactttac caacagtgtc atcgctgaac   2700
gggccaatga aatgaacgcc aatgaagact gtagaggtga tggcaggggc tctgccccct   2760
ccaaaaataa acgcagggcc tttcttgact tgcttttaag tgtgactgat gacgaaggga   2820
acaggctaag tcatgaagat attcgagaag aagttgacac cttcatgttt gaggggcacg   2880
atacaactgc agctgcaata aactggtcct tatacctgtt gggttctaac ccagaagtcc   2940
agaaaaaagt ggatcatgaa ttggatgacg tgtttgggaa gtctgaccgt cccgctacag   3000
tagaagacct gaagaaactt cggtatctgg aatgtgttat taaggagacc cttcgccttt   3060
tccttctgt tccttatttt gccccgtagtg ttagtgaaga ttgtgaagtg gcaggttaca   3120
gagttctaaa aggcactgaa gccgtcatca ttcccctatgc attgcacaga gatccgagat   3180
acttccccaa ccccgaggag ttccagcctg agccggttctt ccccgagaat gcacaagggc   3240
gccatcccata tgcctacgtg cccttctctg ctggccccag gaactgtata ggtcaaaagt   3300
ttgctgtgat ggaagaaaag accattcttt cgtgcatcct gaggcacttt tggatagaat   3360
ccaaccagaa aagagaagag cttggtctag aaggacagtt gattcttcgt ccaagtaatg   3420
gcatctggat caagttgaag aggagaaatg cagatgaacg ctgagaattc aatcaacctc   3480
tggattacaa aatttgtgaa agattgactg gtattcttaa ctatgttgct ccttttacgc   3540
tatgtggata cgctgcttta atgcctttgt atcatgctat tgcttcccgt atggcttttca   3600
ttttctcctc cttgtataaa tcctggttgc tgtctcttta tgaggagttg tggcccgttg   3660
tcaggcaacg tggcgtggtg tgcactgtgt ttgctgacgc aacccccact ggttggggca   3720
ttgccaccac ctgtcagctc ctttccggga cttttcgcttt cccctccct attgccacgg   3780
cggaactcat cgccgcctgc cttgcccgct gctggacagg ggctcggctg ttgggcactg   3840
acaattccgt ggtgtttgtcg gggaaatcat cgtccttttcc ttggctgtc gcctgtgttg   3900
ccacctggat tctgcgcggg acgtccttct gctacgtccc ttcggccctc aatccagcgg   3960
accttccttc ccgcggcctg ctgccggctc tgcggcctct tccgcgtctt cgccttcgcc   4020
ctcagacgag tcggatctcc ctttgggccg cctccccgcg tttattgcag cttataatgg   4080
ttacaaataa agcaatagca tcacaaattt cacaaataaa gcatttttt cactgcattc   4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccgggcggc ctcagtgagc gagcgagcgc gcagctgcct   4320
gcagg                                                              4325

SEQ ID NO: 19         moltype = DNA   length = 4325
FEATURE               Location/Qualifiers
source                1..4325
                      mol_type = other DNA
                      organism = synthetic construct
SEQUENCE: 19
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gactcgagac gcgttgacat tgattattga ctagttatta    180
atagtaatca attacggggt cattagttca tagcccatat atggagttcc gcgttacata    240
acttacggta aatggcccgc ctggctgacc gcccaacgac ccccgcccat tgacgtcaat    300
aatgacgtat gttcccatag taacgccaat agggactttc cattgacgtc aatgggtgga    360
ctatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatggtgtc    540
aggtgagccc cacgttctgc ttcactctcc ccatctcccc ccctccccca ccccaatttt    600
tgtatttatt tattttttaa ttattttgtg cagcgatggg ggcgggggg gggggggcgc    660
gcgccaggcg gggcggggcg gggcgagggg cggggcgggg cgaggcggag aggtgcggcg    720
gcagccaatc agagcggcgc gctccgaaag ttttcttttta tggcgaggcg gcggcggcgg    780
cggccctata aaaagcgaag cgcgcggcgg cgggagtgcg ttcgccccgg tcgccccgg    840
gccccgctcc gcgccgcctc gcgccgcccg cccgggctct gactgaccgc gttactccca    900
caggtgagcg ggcgggacgg ccccttctcct ccgggctgta attagcgctt ggtttaatga    960
cggctcgttt cttttctgtg gctgcgtgaa agccttaaag ggctccggga gggccctttg   1020
tgcgggggg agcggctcgg ggggtgcgtg cgtgtgtgtg tgcgtgggga gcgccgcgtg   1080
cggcccgcgc tgccccgcgg ctgtgagcgc tgcgggcgcg gcgcggggct ttgtgcgctc   1140
cgcgtgtgcg cgaggggagc gcggccgggg gcggtgcccc gcggtgcggg ggggctgcga   1200
ggggaacaaa ggctgcgtgc ggggtgtgtg cgtgggggg tgagcagggg gtgtgggcgc   1260
ggcggtcggc ctgtaacccc ccctgcacc cccctccccg agttgctgag cacggcccgg   1320
cttcgggtgc ggggctccgt acgggcgtg gcgcggggct cgccgtgccg gcgggggt     1380
ggcggcaggt ggggtgccgg ggggcgtgcg gcgcggcggg gggtgccggc ggctcgggga   1440
aggggcgcgg cggccccgg agcgccggcg gctgtcgagg cgcggcgagc cgagctcatt   1500
gcctttatg gtaatcgtgc gagagggcgc agggacttcc tttgtcccaa atctgtgcgg   1560
agccgaaatc tggaggcgc cgcgccacc cctctagcgg gcgcggggcg aagcggtgcg   1620
gcgccggcag gaaggaaatg ggcggggagg ccttcgtgc gtcgccgcgc cgccgtcccc   1680
ttctccatct ccagcctcgg ggctgtccgc agggggacgg ctgccttcgg gggggacggg   1740
```

```
gcagggcggg gttcggcttc tggcgtgtga ccggcggctc tagtgcctct gctaaccatg 1800
ttcatgcctt cttcttttc ctacagctcc tgggcaacgt gctggttatt gtgctgtctc 1860
atcattttgg caaaaagctt gccaccatgg ccggactgtg gctggggctg gtgtggcaga 1920
agctgctgct gtgggggggcc gccagcgctc tgtctctggc tggagccagc ctggtgctga 1980
gcctgctgca gagggtggcc agctacgcta gaaagtggca gcagatgagg cccatccccca 2040
ctgtggcccg ggcctaccct ctggtggac acgctctgct gatgaaaccc gatggcagag 2100
aattcttcca gcagattatc gagtataccg aggaatacag acacatgccc ctgctgaaac 2160
tgtgggtggg acctgtgccc atggtggccc tgtacaacgc cgagaacgtg gaagtgatcc 2220
tgaccagcag caagcagatc gacaaaagca gcatgtacaa attcctggaa ccctggctg 2280
gactgggact gctgaccagc actggaaaca gtggagaag cagaagaaag atgctgaccc 2340
ccaccttcca cttcaccatc ctggaggact tcctggacat catgaacgaa caggccaaca 2400
tcctggtgaa aaagctggaa aaacacatca accaggaagc cttcaactgc ttcttctaca 2460
tcaccctgtg cgccctggac atcatctgcg aaaccgccat gggaaagaac atcggcgccc 2520
agagcaacga cgacagcgaa tacgtgagag ccgtgtatcg gatgtccgag atgatcttca 2580
gaagaatcaa aatgccctgg ctgtggctgg acctgtggta tctgatgttc aaggagggct 2640
gggagcacaa gaagagcctg cagatcctgc ataccttcac caacagcgtg atcgccgaaa 2700
gagccaacga gatgaacgcc aacgaggact gccggggaga cggagaggc agcgctccta 2760
gcaaaaacaa aagaagagcc ttcctggacc tgctgctgag cgtgaccgac gacgaaggaa 2820
atagactgag ccacgaagac atcagagagg aagtggacac attcatgttc gaaggccacg 2880
acacaacagc cgccgccatc aactggtccc tgtacctgct gggcagcaac cccgaggtgc 2940
agaagaaggt ggaccacgag ctggacgacg tgtttgggaa gagcgacaga cctgccaccg 3000
tggaggatct gaaaaagctg agatatctgg agtgcgtgat taaagagcac ctgagactgt 3060
tcccaagtgt gcccctgttc gccagatctg tgagtgagga ctgcgaggtg gccggctata 3120
gagtgctgaa aggaaccgag gccgtgatta ttccctacgc cctgcacagg accccaggt 3180
acttccccca ccccgaggaa ttccagcctg agagattctt tccgagaat gctcaggaa 3240
gacacccccta cgcctatgtg cccttcagcg ccggccccaa aaactgcatt ggccagaagt 3300
tcgccgtgat ggaggagaag accatcctga gctgcatcct gagacacttt tggattgaga 3360
gcaaccagaa gcgggaggag ctgggactgg aaggccagct gatcctgaga ccaagcaacg 3420
gaatctggat caagctgaaa agaagaaacg ccgacgagag atgagaattc aatcaacctc 3480
tggattacaa aatttgtgaa acatattgcg gtattcttaa ctatgttgct ccttttacgc 3540
tatgtggata cgctgcttta atgcctttgt atcatgctat tgcttcccgt atggctttca 3600
ttttctcctc cttgtataaa tcctggttgc tgtctcttta tgaggagttg tggcccgttg 3660
tcaggcaacg tggcgtggtg tgcactgtgt ttgctgacgc aaccccccact ggttggggca 3720
ttgccaccac ctgtcagctc ctttccggga ctttcgcttt cccccctcct attgccactg 3780
cggaactcat cgccgcctgc cttgcccgct gctggacagg ggctcggctg ttgggcactg 3840
acaattccgt ggtgttgtcg gggaaatcat cgtcctttcc ttggctgctc gcctgtgttg 3900
ccacctggat tctgcgcggg acgtccttct gctacgtccc ttcggccctc aatccagcgg 3960
accttccttc ccgcggcctg ctgccggctc tgcggcctct tccgcgtctt cgccttcgcc 4020
ctcagacgag tcggatctcc ctttgggccg cctccccgcg tttattgcag cttataatgg 4080
ttacaaataa agcaatagca tcacaaattt cacaaataaa gcatttttt cactgcattc 4140
tagttgtggt ttgtccaaac tcatcaatgt atcttagcgg ccgcaggaac ccctagtgat 4200
ggagttggcc actccctctc tgcgcgctcg ctcgctcact gaggccgggc gaccaaaggt 4260
cgcccgacgc ccgggctttg cccgggcggc ctcagtgagc gagcgagcgc gcagctgcct 4320
gcagg                                                              4325
SEQ ID NO: 20           moltype = DNA  length = 4325
FEATURE                 Location/Qualifiers
source                  1..4325
                        mol_type = other DNA
                        organism = synthetic construct
SEQUENCE: 20
cctgcaggca gctgcgcgct cgctcgctca ctgaggccgc ccgggcgtcg ggcgaccttg 60
gtcgcccgg cctcagtgag cgagcgagcg cgcagagagg gagtggccaa ctccatcact 120
aggggttcct gcgcctcta gactcgagac gcgttgacat tgattattga ctagttatta 180
atagtaatca attacggggt cattagttca tagcccatat atggagttcc gcgttacata 240
acttacggta aatggcccgc ctggctgacc gcccaacgac ccccgcccat tgacgtcaat 300
aatgacgtat gttcccatag taacgccaat agggactttc cattgacgtc aatgggtgga 360
ctatttacgg taaactgccc acttggcagt acatcaagtg tatcatatgc caagtacgcc 420
ccctattgac gtcaatgacg gtaaatggcc cgcctggcat tatgcccagt acatgacctt 480
atgggacttt cctacttggc agtacatcta cgtattagtc atcgctatta ccatgggtcg 540
aggtgagccc cacgttctgc ttcactctcc ccatctcccc cccctcccca ccccaattt 600
tgtatttatt tattttttaa ttattttgtg cagcgatggg ggcggggggg gggggggcgc 660
gcgccaggcg gggcggggcg gggcgagggg cgggcgggg cgaggcggag aggtgcggcg 720
gcagccaatc agagcggcgc gctccgaaag tttccttttta tggcgaggcg gcggcggcgg 780
cggccctata aaaagcgaag cgcgcggcgg gcgggagtcg ctgcgttgcc ttcgccccgt 840
gccccgctcc gcgccgcctc gcgccgcccg cccggctct gactgaccgc gttactccca 900
caggtgagcg ggcgggacgg ccccttctcct ccgggctgta attagcgctt ggtttaatga 960
cggctcgttt cttttctgtg gctgcgtgaa agccttaaag ggctccggga gggccctttg 1020
tgcggggggg agcggctcgg gggtgcgtg cgtgtgtgtg tgcgtgggga gcgccgggcg 1080
cggcccgcgc tgcccggcgg ctgtgagcgc tgcgggcgcg gcgcggggct tgtgcgctc 1140
cgcgtgtgcg cgaggggagc gcggccgggg cggtgccccc gcggtgcggg ggggctgcga 1200
ggggaacaaa ggctgcgtgc ggggtgtgtg cgtgggggg tgagcagggg gtgtgggcgc 1260
ggcggtcggg ctgtaacccc cccctgcacc cccctcccca agttgctgag cacggcccgg 1320
cttcgggtgc ggggctccgt acggggcgtg gcgcggggct cgccgtgccg ggcggggggt 1380
ggcggcaggt gggggtgccg gcggggcggg gcgcctcg ggccggggag ggctcggggg 1440
aggggcgcgg cggccccggg agcgccgcg gctgtcgagg cgcggcgagc gcagccatt 1500
gccttttatg gtaatcgtgc gagagggcgc agggacttcc tttgtcccaa atctgtgcgg 1560
agccgaaatc tgggaggcgc cgccgcaccc cctctagcgg gcgcggggcg aaggcggtcg 1620
gcgccggcag gaaggaaatg ggcggggagg gccttcgtgc gtcgccgcgc cgccgtcccc 1680
```

```
ttctccatct ccagcctcgg ggctgtccgc aggggacgg ctgccttcgg ggggacggg    1740
gcagggcggg gttcggcttc tggcgtgtga ccggcggctc tagtgcctct gctaaccatg    1800
ttcatgcctt cttcttttc ctacagctcc tgggcaacgt gctggttatt gtgctgtctc    1860
atcattttgg caaaaagctt gccaccatgc ccggactgtg gctgggcctg gtgtggcaga    1920
agctgctgct gtggggcgcc gccagcgctc tgtctctgga tggagcctcc ctggtgctga    1980
gcctgctgca gagggtggcc tcctacgcca gaaagtggca gcagatgagg cccatcccca    2040
cagtggccag ggcctaccct ctggtgggcc acgtctctgct gatgaagcct gacggcaggg    2100
agttttccca gcagatcatc gagtacaccg aggagtacag gcacatgccc ctgctgaagc    2160
tgtgggtggg ccccgtgcct atggtggccc tgtacaatgc cgagaatgtg gaggtcattc    2220
tgacatcctc caagcagatc gataagtcct ccatgtacaa gtttctggag ccttggctgg    2280
gcctcggcct gctgacaagc acaggcaata agtggaggag caggagaaag atgctgaccc    2340
ctaccttca ctttacaatc ctggaggact ttctggatat catgaacgag caggccaaca    2400
tcctggtgaa gaagctggag aagcacatca accaggaggc cttcaattgt ttcttttaca    2460
tcacactgtg cgccctggac atcatctgcg agaccgcaa gggcaagaat atcggcgcc    2520
agtccaacga cgattccgag tacgtgaggg ccgtgtacag gatgagcgag atgatcttta    2580
ggagaatcaa gatgccctgg ctgtggctgg acctgtggta cctgatgttt aaggagggct    2640
gggagcacaa gaagagcctg cagatcctgc acacattcac aaattccgtg atcgccgaga    2700
gagccaacga gatgaatgcc aatgaggact gtagaggcga tggcagggc tccgcccct    2760
ctaagaataa gaggagggcc tttctgacc tgctgctgtc cgtgacagat gacgaggca    2820
ataggctgtc ccacgaggat atcagggagg aggtggacac cttcatgttt gagggccacg    2880
acacaacagc cgccgccatc aactggaggcc tgtacctgct gggcagcaat cccgaggtgc    2940
agaagaaggt ggatcacgag ctggatgatg tgttcggcaa gagcgacaga cccgccacag    3000
tggaggatct gaagaagctg agatacctgg agtgcgtgat caaggagaca ctgagactgt    3060
tcccttccgt gcccctgttc gccagaagcg tgtccgagga ctgtgaggtg gccggctaca    3120
gagtgctgaa gggcaccgag gccgtgatca tccctacgc cctgcacagg atcctagat    3180
acttccctaa ccccgaggag ttccagcccg agaggttttt ccccgagaat gcccagggca    3240
ggcaccccta cgcctacgtg ccttttagcg ccggccctag gaactgtatc ggccagaagt    3300
ttgccgtgat ggaggagaag accatcctgt cctgcatcct gagacacttc tggatcgagt    3360
ccaaccagaa gagggaggag ctgggcctgg agggccagct gatcctgaga cctagcaacg    3420
gcatctggat caagctgaag agaagaaatg ccgatgagga atgagaattc aatcaactc    3480
tggattacaa aatttgtgaa agattgactg gtattcttaa ctatgttgct ccttttacgc    3540
tatgtggata cgctgcttta atgcctttgt atcatgctat tgcttcccgt atggctttca    3600
ttttctcctc cttgtataaa tcctggttgc tgtctctttta tgaggagttg tggcccgttg    3660
tcaggcaacg tggcgtggtg tgcactgtgt ttgctgacgc aacccccact ggttgggca    3720
ttgccaccac ctgtcagctc ctttccggga cttcgcttt ccccctcct attgccacag    3780
cggaactcat cgccgcctgc cttgcccgct gctggacagg ggctcggctg ttgggcactg    3840
acaattccgt ggtgttgtcg gggaaatcat cgtccttttcc ttggctgctc gcctgtgttg    3900
ccacctggat tctgcgcggg acgtccttct gctacgtccc ttcggccctc aatccagcgg    3960
accttccttc ccgcggcctg ctgccggctc tgcggcctct tccgcgtctt cgccttcgcc    4020
ctcagacgag tcggatctcc ctttgggccg cctccccgcg tttattgcag cttataatgg    4080
ttacaaataa agcaatagca tcacaaattt cacaaataaa gcatttttt cactgcattc    4140
tagttgtggt ttgtccaaac tcatcaatgt atcttagcgg ccgcaggaac ccctagtgat    4200
ggagttggcc actccctctc tgcgcgctcg ctcgctcact gaggccgggc gaccaaaggt    4260
cgcccgacgc ccgggctttg cccgggcggc ctcagtgagc gagcgagcgc gcagctgcct    4320
gcagg                                                                4325
```

```
SEQ ID NO: 21         moltype = DNA  length = 4325
FEATURE               Location/Qualifiers
source                1..4325
                      mol_type = other DNA
                      organism = synthetic construct
SEQUENCE: 21
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggcctcta gactcgagac gcgttgacat tgattattga ctagttatta    180
atagtaatca attacggggt cattagttca tagcccatat atggagttcc gcgttacata    240
acttacggta aatggcccgc ctggctgacc gcccaacgac ccccgcccat tgacgtcaat    300
aatgacgtat gttcccatag taacgccaat agggactttc cattgacgtc aatgggtgga    360
ctatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatgggtcg    540
aggtgagccc cacgttctgc ttcactctcc ccatctcccc ccctcccca ccccaatttt    600
tgtatttatt tattttttaa ttattttgtg cagcgatggg gcggggggg ggggggcgc    660
gcgccaggcg gggcggggcg gggcgagggg cgggcggag aggtgcgggg g cagccaatc    720
gcagccaatc agagcggcgc gctccgaaag tttccttttta tggcgaggcg cggcggcgg    780
cggccctata aaagcgaag cgcgcggcg cgggagtcg ctgcgttgcc ttcgccccgt    840
gccccgctcc gcgccgcctc gcgccgcccg ccccggctct gactgaccgc gttactccca    900
caggtgagcg ggcgggacgg cccttctcct ccgggctgta attagcgctt ggtttaatga    960
cggctcgttt cttttctgtg gctgcgtgaa agccttaaag ggctccggga gggcccttg    1020
tgcgggggg agcggctcgg ggggtgcgtg cgtgtgtgtg tgcgtgggga gcgccgcgtg    1080
cggcccgcgc tgcccggcgg ctgtgagcgc tgcgggcgcg gcgcgggct ttgtgcgctc    1140
cgcgtgtgcg cgaggggagc gcggccgggg cggtgcccc gcgtgcggg ggggctgcga    1200
ggggaacaaa ggctgcgtgc ggggtgtgtg cgtgggggg tgagcagggg gtgtgggcgc    1260
ggcggtcggc ctgtaacccc ccctgcacc ccccctcgcc agttgctgag cacggccgg    1320
cttcgggtgc ggggctccgt acggggcgtg gcggggggt cgccgtgccg gcggggggt    1380
ggcggcaggt ggggtgccg ggcggggcgg ggccgcctcg ggccgggag ggctcggggg    1440
aggggcgcgc ggccccgg agccgccgc gctgtcgagg cgcggcgagc gcagccatt    1500
gcctttatg gtaatcgtgc gagagggcgc agggacttc tttgtcccaa atctgtgcgg    1560
agccgaaatc tgggaggcgc cgccgcaccc cctctagcgg gcgcgggcg aagcggtgcg    1620
```

```
gcgccggcag gaaggaaatg ggcggggagg gccttcgtgc gtcgccgcgc cgccgtcccc  1680
ttctccatct ccagcctcgg ggctgtccgc aggggacgg  ctgccttcgg ggggacggg   1740
gcagggcggg gttcggcttc tggcgtgtga ccggcggctc tagtgcctct gctaaccatg  1800
ttcatgcctt cttcttttc  ctacagctcc tgggcaacgt gctggttatt gtgctgtctc  1860
atcattttgg caaaaagctt gccaccatgg ctggactttg gctggactg  tgtggcaaa   1920
aactgctgct gtgggcgct  gctagcgccc tgagcctggc tggagcttct cttgtgctga  1980
gcttactgca aagagtggcc agctatgcca gaaagtggca gcagatgaga cccatcccca  2040
ccgtggctag agcttatcct ctggtgggac atgctctgct gatgaagccc gacggaagag  2100
agttttttcca gcagatcatc gagtacaccg aggagtacga acacatgccc ctgctgaagc  2160
tgtgggtggg cccagttcct atggtggctc tgtataatgc tgaaaacgtg gaggtgatcc  2220
tgaccagcag caagcagatc gacaagagca gcatgtacaa gttcctggag ccctggctgg  2280
gcctgggatt actgacatct acaggaaata aatggagaag cagaagaaag atgctgaccc  2340
ccaccttcca cttcaccatc ctggaggact tcctggacat catgaacgag caggccaaca  2400
tcctggtgaa gaagctggag aagcacatca accaggaggc cttcaactgc ttcttctaca  2460
tcaccctgtg cgcccctggac atcatctgcg agacagctat gggcaagaac atcggcgctc  2520
aaagcaatga cgacagcgag tatgtgagag ccgtgtacag aatgagcgag atgatcttca  2580
gaagaatcaa gatgccctgg ctgtggctgg acctgtggta tctgatgttc aaggagggct  2640
gggagcacaa gaagagcctg cagattctgc acaccttcac caacagcgtg atcgccgaga  2700
gagccaacga gatgaacgcc aacgaggact gcagaggcga cggcagagga tctgctccta  2760
gcaaaaataa gagaagagcc ttcctggacc tgctgctgag cgtgacagat gacgaaggaa  2820
acagactgag ccacgaggac atcagagagg aggtggacac cttcatgttc gagggccacg  2880
acaccaccgc cgctgctatt aattggagcc tgtatctgct gggaagcaac cctgaagtgc  2940
aaaagaaagt ggaccacgag ctggacacgg tgttcggcaa aagcgacaga cccgccacag  3000
tggaggatct gaaaaagctg agatacctgg agtgcgtgat caaggagacc ctgagactgt  3060
tccccagcgt gcccctttc  gctagatctg tgagcgaaga ttgcgaggtg gccggctata  3120
gagtgctgaa aggcaccgaa gccgtgatca tccccctacg ctgcacaga  gaccccagat  3180
acttccccaa ccccgaggag tttcagcccg agagattttt ccccgagaac gcccaaggca  3240
gacacccta  tgcttatgtg cctttcagcg ccggccccag aaattgcatt ggacaaaagt  3300
tcgccgtgat ggaggagaag accatcctga gctgcatcct gagacactc  tggatcgaga  3360
gcaaccagaa gagagaggag ctgggcctgg agggccaagt gattctgaga cctagcaacg  3420
gcatctggat caagctgaag agaagaaacc ccgacgagag atgagaattc aatcaacctc  3480
tggattacaa aatttgtgaa agattgactg gtattcttaa ctatgttgct cctttacgc   3540
tatgtggata cgctgcttta atgcctttgt atcatgctat tgcttcccgt atggctttca  3600
ttttctcctc cttgtataaa tcctggttgc tgtctcttta tgaggagttg tggcccgttg  3660
tcaggcaacg tggcgtggtg tgcactgtgt ttgctgacgc aaccccccact ggttgggca   3720
ttgccaccac ctgtcagctc ctttccggga ctttcgcttt cccctccct  attgccacgg   3780
cggaactcat cgccgcctgc cttgcccgct gctggacagg ggctcggctg ttgggcactg  3840
acaattccgt ggtgttgtcg gggaaatcat cgtcctttcc ttggctgctc gcctgtgttg  3900
ccacctggat tctgcgcggg acgtccttct gctacgtccc ttcggccctc aatccagcgg  3960
accttcctcc ccgcggcctg ctgccggctc tgcggcctct tccgcgtctt cgccttcgcc  4020
ctcagacgag tcggatctcc ctttgggccg cctccccgcg tttattgcag cttataatgg  4080
ttacaaataa agcaatagca tcacaaattt cacaaataaa gcatttttt  cactgcattc   4140
tagttgtggt ttgtccaaac tcatcaatgt atcttagcgg ccgcaggaac cctagtgat   4200
ggagttggcc actccctctc tgcgcgctcg ctcgctcact gaggccgggc gaccaaaggt  4260
cgcccgacgc ccgggctttg cccgggcggc ctcagtgagc gagcgagcgc gcagctgcct  4320
gcagg                                                              4325

SEQ ID NO: 22           moltype = DNA   length = 4325
FEATURE                 Location/Qualifiers
source                  1..4325
                        mol_type = other DNA
                        organism = synthetic construct
SEQUENCE: 22
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct gcggcctcta gactcgagac gcgttgacat tgattattga ctagttatta  180
atagtaatca attacggggt cattagttca tagcccatat atggagttcc gcgttacata  240
acttacggta aatggcccgc ctggctgacc gcccaacgac ccccgcccat tgacgtcaat  300
aatgacgtat gttcccatag taacgccaat agggactttc cattgacgtc aatgggtgga  360
ctatttacgg taaactgccc acttggcagt acatcaagtg tatcatatgc caagtacgcc  420
ccctattgac gtcaatgacg gtaaatggcc cgcctggcat tatgcccagt acatgacctt  480
atgggacttt cctacttggc agtacatcta cgtattagtc atcgctatta ccatgggtcg  540
aggtgagccc cacgttctgc ttcactctcc ccatctcccc ccctcccca  ccccaattt    600
tgtatttatt tattttttgt gcagcgatgg gggcgggggg gggggggggc gcgcgccagg  660
cgcccaggcg gggcggggcg gggcgagggg cggggcgggg cgaggcggag aggtgcggcg  720
gcagccaatc agagcggcgc gctccgaaag ttcctttta  tggcgaggcg gcggcggcgg  780
cggccctata aaaagcgaag cgcgcggcgg gcgggagtcg ctgcgttgcc ttcgccccgt  840
gccccgctcc gccgccgcct cgcgccgccc g ccccggctct gactgaccgc gttactccca  900
caggtgagcg ggcgggacgg cccttctcct ccgggctgta attagcgctt ggtttaatga  960
cggctcgttt ctttttctgtg gctgcgtgaa agccttaaag ggctccggga gggccctttg  1020
tgcggggggg agcggctcgg ggggtgcgtg cgtgtgtgtg tgcgtgggga gcgccgcgtg  1080
cggcccgcgc tgcccggcgg ctgtgagcgc tgcgggcgcg gcgcggggct ttgtgcgctc  1140
cgcgtgtgcg cgaggggagc gcggccgggg cggtgcccc  gcggtgcggg ggggctgcga  1200
ggggaacaaa ggctgcgtgc ggggtgtgtg cgtgggggga tgcagccggg gtggggacgg  1260
ggcggtcgcg ctgtaacccc cccctgcacc cccctccccg agttgctgag cacgccggg   1320
cttcgggtgc ggggctccgt acggggcgtg gcgcggggct cgccgtgccg gggcggggt   1380
ggcggcaggt gggggtgccg gcggggcgg  gccgcctcg  ggccggggag ggctcggggg   1440
aggggcgcgg cgcccccgg  agcgccgcg  gctgtcgagg cgcggcgagc cgcagccatt  1500
gccttttatg gtaatcgtgc gagagggcgc aggaacttcc tttgtcccaa atctgtgcgg  1560
```

```
agccgaaatc tgggaggcgc cgccgcaccc cctctagcgg gcgcggggcg aagcggtgcg   1620
gcgccggcag gaaggaaatg ggcggggagg gccttcgtgc gtcgccgcgc cgccgtcccc   1680
ttctccatct ccagcctcgg ggctgtccgc aggggacgg  ctgccttcgg ggggacggg   1740
gcagggcggg gttcggcttc tggcgtgtga ccggcggctc tagtgcctct gctaaccatg   1800
ttcatgcctt ctttcttttc ctacagctcc tgggcaacgt gctggttatt gtgctgtctc   1860
atcattttgg caaaaagctt gccaccatgg caggactgtg gctgggactg gtgtggcaga   1920
agctgctgct gtggggagca gcaagcgccc tgtccctggc aggcgcctcc ctggtgctgt   1980
ctctgctgca gagggtggca agctacgcaa ggaagtggca gcagatgcgg cccatcccta   2040
ccgtggcaag agcatatcca ctggtgggac acgcactgct gatgaagcct gacggccgcg   2100
agttctttca gcagatcatc gagtacacag aggagtatcg gcacatgcca ctgctgaagc   2160
tgtgggtggg accagtgcca atggtggccc tgtacaacgc cgagaatgtg gaagtgatcc   2220
tgaccagctc caagcagatc gataagtcta gcatgtataa gttcctggag ccttggctgg   2280
gactgggact gctgacctcc acaggcaaca agtgagggtc tcggagaaag atgtgaccc    2340
caacattcca ctttacaatc ctggaggact tcctggtaga tcatgaacgag caggccaata   2400
tcctggtgaa gaagctggag aagcacatca accaggagge ctttaattgc ttcttttaca   2460
tcaccctgtg cgccctggac atcatctgtg agacagccat gggcaagaac atcggcgccc   2520
agagcaatga cgattccgag tacgtgaggg ccgtgtatcg catgtccgag atgatcttta   2580
ggcgcatcaa gatgccctgg ctgtggctgg atctgtggta tctgatgttc aaggagggct   2640
gggagcacaa gaagagcctg cagatcctgc acaccttta  aaactccgtg atcgccgagc   2700
gggccaatga gatgaacgcc aatgaggact gtaggggcga tggaagaggc tctgcccta    2760
gcaagaacaa gcggagagcc ttcctggacc tgctgctgtc tgtgaccgac gatgagggca   2820
atagactgag ccacgaggac atcagggagg aggtggatac attcatgttt gagggacacg   2880
acaccacagc agcagccatc aactggtctc tgtacctgct gggcagcaat ccagaggtgc   2940
agaagaaggt ggatcacgag ctggacgacg tgttcggcaa gagcgacaga cccgccaccg   3000
tggaggatct gaagaagctg aggtacctgg agtgcgtgat caaggagaca ctgagactgt   3060
tccctccgt gcctctgttt gccagtccg tgtctgagga ctgtgaggtg gccggctatc   3120
gcgtgctgaa gggcaccgag ccgtgatca tccttacgc cctgcaccgg gaccccagat   3180
atttcctaa cccagaggag ttcagcag agcggttctt cccagagaat gcacagggcc   3240
ggcaccctta cgcctatgtg ccattctctg ccggaccaag gaactgcatc ggacagaagt   3300
ttgccgtgat ggaggaagaa accatcctgt cctgtatcct gcgccacttc tggatcgaat   3360
ctaatcagaa gagggagag ctggactgga agggacagct gatcctgaga ccctccaacg   3420
gcatctggat caagctgaag aggcgcaatg ccgatgagag gtgagaattc aatcaacctc   3480
tggattacaa aatttgtgaa agattgactg gtattcttaa ctatgttgct cctttacgc   3540
tatgtggata cgctgcttta atgcctttgt atcatgctat tgcttcccgt atggctttca   3600
ttttctccctc cttgtataaa tcctggttgc tgtctctttta tgaggagttg tggcccgttg   3660
tcaggcaacg tggcgtggtg tgcactgtgt ttgctgacgc aacccccact ggttgggca   3720
ttgccaccac ctgtcagctc ctttccggga ctttcgcttt cccctcct attgccacgg   3780
cggaactcat cgccgcctgc cttgcccgct gctggacagg ggctcggctg ttgggcactg   3840
acaattccgt ggtgttgtcg gggaaatcat cgtcctttcc ttggctgctc gcctgtgttg   3900
ccacctggat tctgcgcggg acgtcctct gctacgtccc ttcggccctc aatccagcgg   3960
accttccttc ccgcggcctg ctgccggctc tgcggcctct tccgcgtctt cgccttcgcc   4020
ctcagacgag tcggatctcc ctttgggccg cctccccgcg tttattgcag cttataatgg   4080
ttacaaataa agcaatagca tcacaaattt cacaaataaa gcatttttt cactgcattc   4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccgggcggc ctcagtgagc gagcgagcgc gcagctgcct   4320
gcagg                                                             4325

SEQ ID NO: 23         moltype = DNA   length = 4325
FEATURE               Location/Qualifiers
source                1..4325
                      mol_type = other DNA
                      organism = synthetic construct
SEQUENCE: 23
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gactcgagac gcgttgacat tgattattga ctagttatta    180
atagtaatca attacggggt cattagttca tagcccatat atggagttcc gcgttacata    240
acttacggta aatggcccgc ctggctgacc gcccaacgac ccccgcccat tgacgtcaat    300
aatgacgtat gttcccatag taacgccaat agggactttc cattgacgtc aatgggtgga    360
ctatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatgggtcg    540
aggtgagccc cacgttctgc ttcactctcc ccatctcccc ccccctcca ccccaattt    600
tgtatttatt tatttttaa ttattttgtg cagcgatggg ggcggggggg gggggggcgc    660
gcgccaggcg gggcggggcg gggcgagggg cgggcgggg cgaggcggag aggtgcggcg    720
gcagccaatc agagcggcgc gctccgaaag tttcctttta ggcgaggcg gcggcggcgg    780
cggccctata aaaagcgaag cgcgcggcgg gcggagtcgc ctgcgttgcc ttcgccccgt    840
gccccgctcc gcgccgcctc gcgccgcccg cccgcccgcc gactgaccgc gttactccca    900
caggtgagcg ggcgggacgg cccttctcct ccgggctgta attagcgctt ggtttaatga    960
cggctcgttt cttttctgtg gctgcgtgaa agccttaaag gctccggga gggccctttg    1020
tgcgggggg agcggctcgg ggggtgcgtg cgtgtgtgt gcgtgggga gcgccgcgtg    1080
cggccccgcg tgcccggcgg ctgtgagcgc tgcgggcgcg gcgcgggct ttgtgcgctc   1140
cgcgtgtgcg cgaggggagc cgggccgcgc tgcccgcgtc gcgaggcgcga   1200
ggggaacaaa ggctgcgtgc gggggtgtgtg cgtgggggg tgagcagggg gtgtgggcgc   1260
ggcggtcggg ctgtaacccc ccctgcacc ccctccccg agttgctgag cacggcccgg    1320
cttcgggtgc ggggctccgt acgggggcgtg gcgcggggct cgccgtgccg ggcggggggt  1380
ggcggcaggt ggggggtgccg gcggggcgg ggccgcctcg ggccggggag ggctcggggg   1440
aggggcgcg cggccccgg agcgccggcg gctgtcgagg cgcggcgagc cgcagccatt    1500
```

```
gccttttatg gtaatcgtgc gagagggcgc agggacttcc tttgtcccaa atctgtgcgg   1560
agccgaaatc tgggaggcgc cgccgcaccc cctctagcgg gcgcggggcg aagcggtgcg   1620
gcgccggcag gaaggaaatg ggcggggagg gccttcgtgc gtcgccgcgc cgccgtcccc   1680
ttctccatct ccagcctcgg ggctgtccgc aggggagcgg ctgccttcgg ggggacggg    1740
gcagggcggg gttcggcttc tggcgtgtga ccggcggctg tagtgcctct gctaaccatg   1800
ttcatgcctt cttctttttc ctacagctcc tgggcaacgt gctggttatt gtgctgtctc   1860
atcattttgg caaaaagctt gccaccatgg ctggactgtg gctggactg gtgtggcaga    1920
agctgctgct gtgggcgct gcctctgccc tcagtctggc tggagccagc ctggtcctgt    1980
ctctgctcca gagagtggct tcttatgcca gaaagtggca gcaaatgagg cctatcccta   2040
ctgtcgccag agcctaccct ctggttggac acgccctgct gatgaagcct gacggcaggg   2100
agttctttca gcagataatc gaatacactg aagaatacag acacatgcct ctcctgaaac   2160
tctgggtggg accagttcct atggtcgccc tgtacaatgc cgagaatgtc gaagtgatcc   2220
tgaccagctc aaagcagatt gataagtcta gcatgtacaa gttcctggag ccctggctgg   2280
gactcggcct gctcacctcc accggcaata gtggccgtc aagaaggaag atgctcactc   2340
caacctttca ctttaccata ctggaggact ttctcgacat catgaatgag caagccaaca   2400
ttctcgttaa gaagctggag aaacacataa accaggaggc tttcaactgt ttcttctaca   2460
taaccctgtg cgctctggac atcatctgcg aaaccgctat gggcaagaac ataggagccc   2520
aatccaatga cgattctgag tacgtcaggg ctgtctaccg catgtctgag atgatcttca   2580
gacggattaa gatgccctgg ctgtggctgg atctgtggta tctgatgttc aaggaaggat   2640
gggagcacaa gaagtctctg caaatcctcc atacattcac taacagtgtc attgctgaaa   2700
gggctaacga gatgaatgct aatgaagatt gcagaggaga tggacgcggt tccgcacctt   2760
ccaagaacaa gcgcagagca tttctcgatc cctgctgag tgttaccgac gacgagggca   2820
accggctgtc ccatgaggac atcagggaag aggtggatac ctttatgttc gagggccacg   2880
ataccaccgc agctgctatc aactggtccc tctatctgct gggttccaac cctgaagtgc   2940
agaagaaggt tgaccacgaa ctcgatgacg tgtttggtaa gagcgacaga cctgccaccg   3000
tcgaggacct gaagaagctc cgctacctgg agtgtgtgat caaggagaca ctcaggctgg   3060
ttcctagcgt gcctctgttc gctaggtctg tctctgagga ttgcgaggtt gccggataca   3120
gagtgctcaa aggaactgag gccgtcataa tcccttacgc cctgcaccgc gaccctagat   3180
actttccaa tcccgaggag ttccaaccag agagattctt ccctgagaat gcccaaggca   3240
ggcatcctta tgcttatgtc ccattctctg ccggacctag gaattgtatt ggacagaagt   3300
tcgccgttat ggaagagaag acaatcctgt cctgtatact gcgccacttc tggatcgaga   3360
gcaatcagaa gagggaggaa ctcggcctgg aaggacagct cattctcaga ccttcaaacg   3420
ggatttggat caaactcaaa cggagaaacg ccgacgagag gtgagaattc aatcaacctc   3480
tggattacaa aatttgtgaa agattgactg gtattcttaa ctatgttgct ccttttacgc   3540
tatgtggata cgctgcttta atgcctttgt atcatgctat tgcttcccgt atggctttca   3600
ttttctcctc cttgtataaa tcctggttgc tgtctcttta tgaggagttg tggcccgttg   3660
tcaggcaacg tggcgtggtg tgcactgtgt ttgctgacgc aacccccact ggttgggca    3720
ttgccaccac ctgtcagctc ctttccggga ctttcgcttt ccccctccct attgccacgg   3780
cggaactcat cgccgcctgc cttgcccgct gctggacagg ggctcggctg ttgggcactg   3840
acaattccgt ggtgttgtcg gggaaatcat cgtcctgtcc ttggctgctc gcctgtgttg   3900
ccacctggat tctgcgcggg acgtccttct gctacgtccc ttcggccctc aatccagcgg   3960
accttccttc ccgcggcctg ctgccggctc tgcggcctct tccgcgtctt cgccttcgcc   4020
ctcagacgag tcggatctcc ctttgggccg cctccccgcc tgttattgcg ctataatgg    4080
ttacaaataa agcaatagca tcacaaattt cacaaataaa gcatttttt cactgcattc    4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccgggcggc ctcagtgagc gagcgagcgc gcagctgcct   4320
gcagg                                                              4325
```

```
SEQ ID NO: 24          moltype = DNA  length = 4325
FEATURE                Location/Qualifiers
source                 1..4325
                       mol_type = other DNA
                       organism = synthetic construct
SEQUENCE: 24
cctgcaggca gctgcgcgct cgctcgctca ctgaggccgc cgggcgtcg ggcgaccttt     60
ggtcgcccgg cctcagtgag cgagcgagcg cgcagagagg gagtggccaa ctccatcact   120
aggggttcct gcgcctcta gactcgagac gcgttgacat tgattattga ctagttatta   180
atagtaatca attacggggt cattagttca tagcccatat atggagttcc gcgttacata   240
acttacggta aatggcccgc ctggctgacc gcccaacgac ccccgcccat tgacgtcaat   300
aatgacgtat gttcccatag taacgccaat agggactttc cattgacgtc aatgggtgga   360
ctatttacgg taaactgccc acttggcagt acatcaagtg tatcatatgc caagtacgcc   420
ccctattgac gtcaatgacg gtaaatggcc cgcctggcat tatgcccagt acatgacctt   480
atgggacttt cctacttggc agtacatcta cgtattagtc atcgctatta ccatggtcg    540
aggtgagccc cacgttctgc ttcactctcc ccatctcccc ccctcccca cccccaatttt   600
tgtatttatt tatttttaa ttattttgtg cagcgatggg ggcgggggg gggggggcgc    660
gcgccaggcg gggcggggcg gggcgagggg cgggcgggg cgaggcggag aggtgcggc    720
gcagccaatc agagcggcgc gctccgaaag tttccttta tggcgaggcg gcggcggcgg   780
cggccctata aaaagcgaag cgcgcggcgg gcgggagtcg ctgcgttgcc ttcgcccgt    840
gccccgctcc gcgccgcctc gcgccgcccg cccggctct gactgaccgc gttactccca    900
caggtgagcg ggcgggacgg cccttctcct ccgggctgta attagcgctt ggtttaatga   960
cggctcgttt cttttctgtg gctgcgtgaa agccttaaag gctccggga gggccctttt   1020
tgcgggggg agcggctcgg ggggtgcgtg cgtgtgtgt gcgtgggga cgccgcgtg     1080
cgcccgcgc tgcccggcgc ctgtgagcgc ggcggcgct ttgtcgctca               1140
ccgtgtgcg cgaggggagc gggcggcggg gcggtgcccc gcggtgcggg gggctgcga    1200
ggggaacaaa ggctgcgtgc gggtgtgtg cgtgggggg tgagcagggg gtgtgggcgc    1260
ggcggtcggc ctgtaacccc ccctgcacc ccctccccg agttgctgag cacggccgg     1320
cttcgggtgc ggggctccgt acggggcgtg gcgcggggct cgccgtgccg ggcgggggt   1380
ggcggcaggt ggggtgccg ggcggggcgg ggccgctcg ggccggggag ggctcgggg    1440
```

```
agggggcgcgg cggcccccgg agcgccggcg gctgtcgagg cgcggcgagc cgcagccatt 1500
gcctttatg gtaatcgtgc gagagggcgc agggacttcc tttgtcccaa atctgtgcgg 1560
agccgaaatc tgggaggcgc cgccgcaccc cctctagcgg gcgcggggcg aagcggtgcg 1620
gcgccggcag gaaggaaatg ggcggggagg gccttcgtgc gtcgccgcgc cgccgtcccc 1680
ttctccatct ccagcctcgg ggctgtccgc aggggacgg ctgccttcgg gggggacggg 1740
gcagggcggg gttcggcttc tggcgtgtga ccggcggctc tagtgcctct gctaaccatg 1800
ttcatgcctt cttctttttc ctacagctcc tgggcaacgt gctggttatt gtgctgtctc 1860
atcatttgg caaaaagctt gccaccatgc tggtctgtg gctgggcctg gtgtggcaga 1920
agctgctgct gtgggagct gcctctgctc tgtcctggc tggtgcctcc ctggtgctga 1980
gcctgctgca gagggtggcc tcctatgcta ggaagtggca gcagatgagg cccatcccca 2040
cagtggccag ggcctacccc ctggtgggcc atgctctgct gatgaagcct gatggcaggg 2100
agttcttcca gcagatcatt gaatacacag aagagtacag gcacatgcct ctgctgaagc 2160
tgtgggtggg ccctgttcct atggtggccc tgtacaatgc tgagaatgtt gaggtcattc 2220
tgacctcctc caagcagatt gataagtcca gcatgtacaa gttctgtgag cctggctgg 2280
gcctgggtct gctgacatcc acaggtaata agtggagaag cagaaggaag atgctgacac 2340
ccaccttttca cttcacaatc ctggaggact tcctggatat catgaatgag caggccaaca 2400
tcctggtgaa gaagctggag aagcacatca atcaggaggc cttcaactgc ttttctaca 2460
tcaccctgtg tgccctggat atcatctgtg aaacagctat gggcaagaat attggtgccc 2520
agagcaatga tgactctgaa tatgttaggg ctgtttacag aatgtctgaa atgatcttta 2580
gaaggatcaa gatgccttgg ctgtggctgg atctgtggta cctgatgttt aaggagggct 2640
gggagcacaa gaagtccctg cagatcctgc acacctttac caactctgtt attgctgaga 2700
gagccaatga aatgaatgcc aatgaggact gcaggggaga tgcagaggc tctgctcctt 2760
ccaagaataa gagaagagcc ttcctggatc tgctgctgtc tgttacagat gatgaaggca 2820
acaggctgag ccatgaagac atcagggagg aggtggatac attcatgttt gagggccatg 2880
ataccacagc tgctgctatc aactggtccc tgtacctgct gggcagcaac cctgaggtgc 2940
agaagaaggt ggaccatgaa ctggatgatg ttttggcaga gtctgataga cctgctacag 3000
ttgaggacct gaagaagctg aggtacctgg agtgtgtgat caaggagaca ctgaggctgt 3060
ttccttctgt tcccctgttt gccagatctg tttctgaaga ttgtgaagtg gctggttaca 3120
gggtgctgaa gggcacagag gctgttatca tccctatgc tctgcacaga ccccagat 3180
actttcctaa tcctgaggag tttcagcctg aaaggtttt ccctgagaat gctcagggca 3240
gacacccta tgcttatgtt cccttctctg ctgccctag gaactgcatt ggtcagaagt 3300
tgctgtgat ggaggagaag accatcctga gctgcatcct gagacacttc tggattgaaa 3360
gcaaccagaa gagggaggag ctgggcctgg agggccagct gatcctgagg ccctccaatg 3420
gcatctggat caagctgaag agaagaaatg ctgatgagag atgagaattc aatcaacctc 3480
tggattacaa aattgtgaa agattgactg gtattcttaa ctatgttgct ccttttacgg 3540
tatgtggata cgctgcttta atgcctttgt atcatgctat tgcttcccgt atggctttca 3600
tttttctcctc cttgtataaa tcctggttgc tgtctcttta tgaggagttg tgggcccgttg 3660
tcaggcaacg tggcgtggtg tgcactgtgt ttgctgacgc aacccccact ggttgggca 3720
ttgccaccac ctgtcagctc cttttcggga cttttcgcttt tgtgccacgg 3780
cggaactcat cgccgcctgc cttgcccgct gctggacagg ggctcggctg tgggcactg 3840
acaattccgt ggtgttgtcg gggaaatcat cgtccttttcc ttgctgctc gcctgtgttg 3900
ccacctggat tctgcgcggg acgtcctcct gctacgtccc ttcggccctc aatccagcgg 3960
accttcttcc ccggcggcctc ctgccggctc tgcgctcttc gcccttgcc 4020
ctcagacgag tcggatctcc ctttgggccg cctcccgcg tttattgcag cttataatgg 4080
ttacaaataa agcaatagca tcacaaattt cacaaataaa gcattttttt cactgcattc 4140
tagttgtggt ttgtccaaac tcatcaatgt atcttagcgg ccgcaggaac ccctagtgat 4200
ggagttggcc actccctctc tgcgcgctcg ctcgctcact gaggccgggc gaccaaaggt 4260
cgcccgacgc ccgggctttg cccgggcggc ctcagtgagc gagcgagcgc gcagctgcct 4320
gcagg                                                               4325
```

SEQ ID NO: 25          moltype = DNA   length = 4325
FEATURE                Location/Qualifiers
source                 1..4325
                       mol_type = other DNA
                       organism = synthetic construct
SEQUENCE: 25

```
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggcctcta gactcgagac gcgttgacat tgattattga ctagttatta 180
atagtaatca attacggggt cattagttca tagcccatat atggagttcc gcgttacata 240
acttacggta aatggcccgc ctggctgacc gcccaacgac ccccgcccat tgacgtcaat 300
aatgacgtat gttcccatag taacgccaat agggactttc cattgacgtc aatgggtgga 360
ctatttacgg taaactgccc acttggcagt acatcaagtg tatcatatgc caagtacgcc 420
ccctattgac gtcaatgacg gtaaatggcc cgcctggcat tatgcccagt acatgacctt 480
atgggacttt cctacttggc agtacatcta cgtattagtc atcgctatta ccatgggtcg 540
aggtgagccc cacgttctgc ttcactctcc ccatctcccc ccctcccca ccccaatttt 600
gtatttatt tattttttaa ttattttgtg cagcgatggg ggcgggggg gggggggcgc 660
gcgccaggcg gggcggggcg gggcgagggg cggggcgggg cgaggcggag aggtgcggcg 720
gcagccaatc agagcggcgc gctccgaaag tttccttttta tggcgaggcg gcggcggcgg 780
cggccctata aaaagcgaag cgcgcggcgg gcgggagtcg ctgcgttgcc ttcgccccgt 840
gccccgctcc gcgccgcctc gcgccgcccg cccggctct gactgaccgc gttactccca 900
caggtgagcg ggcgggacgg cccttctcct ccgggctgta attagcgctt ggtttaatga 960
cggctcgttt cttttctgtg gctgcgtgaa agccttaaag ggctccggga gggccctttg 1020
tgcgggggg agcggctcgg ggggtgcgtg cgtgtgtgtg tgcgtgggga gcgccgcgtg 1080
cggcccgcgc tgcccggcgg ctgtgagcgc tgcgggcgcg gcgcggggct ttgtgcgctc 1140
cgcgtgtgcg cgaggggagc gcggccgggg gcggtgcccc gcggtgcggg gggctgcga 1200
ggggaacaaa ggctgcgtgc ggggtgtgtg cgtgggggg tgagcagggg gtgtgggcgc 1260
ggcggtcggg ctgtaacccc cccctgcacc ccctccccg agttgctgag cacggcccgg 1320
cttcgggtgc ggggctccgt acgggcgtg gcgcggggct cgccgtgccg ggcggggggt 1380
```

```
ggcggcaggt gggggtgccg ggcggggcgg ggccgcctcg ggccggggag ggctcggggg    1440
aggggcgcgg cggcccccgg agcgccggcg gctgtcgagg cgcggcgagc cgcagccatt    1500
gccttttatg gtaatcgtgc gagagggcgc agggacttcc tttgtcccaa atctgtgcgg    1560
agccgaaatc tgggaggcgc cgccgcaccc cctctagcgg gcgcggggcg aagcggtgcg    1620
gcgccggcag gaaggaaatg ggggcgggag ggccttcgtg gtcgccgcgc cgccgtcccc    1680
ttctccatct ccagcctcgg ggctgtccgc aggggacggg ctgccttcgg ggggacggg     1740
gcagggcggg gttcggcttc tggcgtgtga ccggcggctc tagtgcctct gctaaccatg    1800
ttcatgcctt cttcttttc ctacagctcc tgggcaacgt gctggttatt gtgctgtctc     1860
atcattttgg caaaaagctt gccaccatgg ctggcctgtg gctggggcgg gtctggcaga    1920
agctgctcct gtgggggct gcctccgcc tctccctggc tggggctagc ctggtgctga      1980
gcctgctgca gagagtggct agctatgcta gaaagtggca gcagatgaga cccatcccca    2040
cagtggctag agcctacccc ctggtgggcc atgcccgct gatgaagcct gatggcagag      2100
agttcttca gcagatcatt gagtacacag gagagtacag acacatgccc ctgctgaagc     2160
tgtgggtggg ccctgtgcct atggtagcac tgtacaatgc tgagaatgtg gaggtgatcc    2220
tgacaagcag caagcagatt gacaagagca gcatgtacaa gttcctggag ccctggctgg    2280
gcctgggcct gctgacaagc accggcaaca agtggagaag cagaagaaag atgctgaccc    2340
ccaccttcca cttcaccatc ctggaggact tcctggacat catgaatgag caagccaaca    2400
tcctggtgaa gaagctggag aagcatcatca accaagagc cttcaactgc ttcttctaca    2460
tcaccctgtg tgccctggat atcatctgtg agacagccca gggcaagaac attgggctc      2520
agagcaatga tgacagcgag tatgtgagag ctgtgtacag aatgagcgag atgatcttca    2580
gaagaatcaa gatgccctgg ctgtggctgg acctgtggta cctgatgttc aaggagggct    2640
gggagcaacaa gaagagcctg cagatcctgc acaccttcac caacagcgtg attgctgaga   2700
gagccaatga tgatgaatgcc aatgaggact gcagaggga tggcagaggc agcgccccta    2760
gcaagaacaa gagaagagcc ttcctggacc tgctcctgag cgtgacagat gatgagggca    2820
acagactgag ccatgaggac atcagagaag aggtggcac cttcatgttt gagggccatg    2880
acaccacagc tgctgccatc aactggagcc tgtacctgct ggcagccaac cctgaggtgc    2940
agaagaaggt ggaccatgag ctggatgatg tgtttggcaa gagcgacaga cctgccacag    3000
tggaggacct gaagaagctg agatacctgg agtgtgtgat caaggagacc ctgagactgt    3060
tccccagcgt gccccctgttt gctagaagcg tgagcgagga ctgtgaggtg gctggctaca    3120
gagtgctgaa gggcacagag gctgtgatca tccccctatgc cctgacacga gaccctagat   3180
acttccccaa ccctgaggag tttcagcctg agagattctt ccctgagaat gcccaaggca    3240
gacacccccta tgcctatgtg cccttcagcg ctggccctag aaactgcatt gggcagaagt    3300
tgctgtgat ggaggagaag accatcctga gctgcatcct gagacacttc tggattgaga    3360
gcaatcagaa gagagaggag ctgggcctgg aggggcagct gatcctgaga cctagcaatg    3420
gcatctggat caagctgaag agaagaaatg atgagaattc aatcaacctc tggattacaa    3480
aatttgtgaa agattgactg gtattcttaa ctatgttgct ccttttacgc                 3540
tatgtggata cgctgcttta atgcctttgt atcatgctat tgcttccgt atggcttca     3600
ttttctcctc cttgtataaa tcctggttgc tgtctctta tgaggagttg tggcccgttg     3660
tcaggcaacg tggcgtggtg tgcactgtgt ttgctgacac aacccccact ggttgggca     3720
ttgccaccac ctgtcagctc ctttccggga cttcgcttt cccctcct attgccacgg       3780
cggaactcat cgccgcctgc cttgcccgct gctggacagg ggctcggctg ttgggcactg    3840
acaattccgt ggtgttgtcg gggaaatcat cgtcctttcc ttggctgctc gcctgtgttg    3900
ccacctggat tctgcgcggg acgtccttct gctacgtccc ttcggccctc aatccagcgg    3960
accttccttc ccgcggcctg ctgccggctc tgcggcctct tccgcgtctt cgccttcgcc    4020
ctcagacgag tcggatctcc cttgggccg cctcccgcg tttattgcag cttataatgg      4080
ttacaaataa agcaatagca tcacaaattt cacaaataaa gcatttttt cactgcattc     4140
tagttgtggt ttgtccaaac tcatcaatgt atcttagttc ccgcaggaac ccctagtgat    4200
ggagttggcc actccctctc tgcgcgctcg ctcgctcact gaggccgggc gaccaaaggt    4260
cgcccgacgc ccgggctttg cccgggcggc ctcagtgagc gagcgagcgc gcagctgcct    4320
gcagg                                                                4325
```

```
SEQ ID NO: 26          moltype = DNA   length = 4325
FEATURE                Location/Qualifiers
source                 1..4325
                       mol_type = other DNA
                       organism = synthetic construct
SEQUENCE: 26
cctgcaggca gctgcgcgct cgctcgctca ctgaggccgc ccgggcgtcg ggcgaccttt      60
ggtcgcccgg cctcagtgag cgagcgagcg cgcagagagg gagtgccaa ctccatcact      120
aggggttcct gcggcctcta gactcgagac gcgttgacat tgattattga ctagttatta     180
atagtaatca attacggggt cattagttca tagcccatat atggagttcc gcgttacata     240
acttacggta aatggcccgc ctggctgacc gcccaacgac ccccgcccat tgacgtcaat     300
aatgacgtat gttcccatag taacgccaat agggactttc cattgacgtc aatgggtgga    360
ctatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatgggtcg    540
aggtgagccc cacgttctgc ttcactctcc ccatctcccc ccctcccca ccccaatttt     600
tgtatttatt tattttttaa ttatttgtg cagcgatggg ggcggggggg ggggggcgc     660
gcgccaggcg gggcggggcg gggcgagggg cgggcggga aggtgcggcg                720
gcagccaatc agagcggcgc gctccgaaag tttcctttta tggcgaggcg gcggcggcgg   780
cggccctata aaaagcgaag cgcgcggcgg gcgggagtcg ctgcgttgcc ttcgccccgt     840
gccccgctcc gcgccgcctc gcgccgcccg cccggctct gactgaccgc gttactccca    900
caggtgagcg gcgggacgg ccctttctcct ccgggctgta attagcgctt ggtttaatga    960
cggcttgttt cttttctgtg gctgcgtgaa agccttaaag ggctccggga gggccctttg    1020
tgcggggggg agcggctcgg ggggtgcgtg cgtgtgtgtg tgcgtgggga gcgccgcgtg    1080
cggcccgcgc tgcccggcgg ctgtgagcgc tgcgggcgcg gcgcggggct ttgtgcgctc    1140
cgcgtgtgcg cgaggggagc gcggccgggg cggtgccccc gcggtgcggg ggggctgcga    1200
ggggaacaaa ggctgcgtgc ggggtgtgtg cgtgggggg tgagcagggg gtgtgggcgc     1260
ggcggtcggg ctgtaacccc ccctgcacc cccctcccg agttgctgag cacggcccgg    1320
```

```
cttcggggtgc ggggctccgt acggggcgtg gcgcggggct cgccgtgccg ggcggggggt 1380
ggcggcaggt gggggtgccg ggcggggcgg ggccgcctcg ggccggggag ggctcggggg 1440
aggggcgcgg cggcccccgg agccgccgcg gctgtcgagg cgcggcgagc cgcagccatt 1500
gccttttatg gtaatcgtgc gagagggcgc agggacttcc tttgtcccaa atctgtgcgg 1560
agccgaaatc tgggaggcgc cgccgcaccc cctctacggg cgcgggaacg aagcggtgcg 1620
gcgccggcag gaaggaaatg ggcggggagg gccttcgtgc gtcgccgcgc cgccgtcccc 1680
ttctccatct ccagcctcgg ggctgtccgc aggggacggg ctgccttcgg ggggacggg 1740
gcagggcggg gttcggcttc tggcgtgtga ccggcggctc tagtgcctct gctaaccatg 1800
ttcatgcctt cttcttttc ctacagctcc tgggcaacgt gctggttatt gtgctgtctc 1860
atcattttgg caaaaagctt gccaccatgg ctgggcctgt gctgggcctg gtgtggcaga 1920
agctgctgct gtggggagct gccagtgccc tgagcctggc tggggccagc ctggtgctga 1980
gcctgctgca gagggtggcc agctatgcca ggaagtggca gcagatgagg cccatcccca 2040
cagtggccag ggcctacccc ctggtgggcc atgccctgct gatgaagcct gatggcaggg 2100
agttcttcca gcagatcatt gagtacacag aggagtacag gcacatgcgc ctgctgaagc 2160
tgtgggtggg ccctgtccct atggtggccc tgtacaatgc tgagaatgtg gaggtgatcc 2220
tgaccagcag caagcagatt gacaagagca gcatgtacaa gttcctggag ccctggctgg 2280
gcctgggcct gctgaccagc acaggcaaca agtggaggag caggaggaag atgctgaccc 2340
ccaccttcca cttcaccatc ctggaggact tcctggacat catgaatgag tggcaacaa 2400
tcctggtgaa gaagctggag aagcacatca accaggaggc cttcaactgc ttcttctaca 2460
tcaccctgtg tgccctggac atcatctgta gacagccat gggcaagaac attggagccc 2520
agagcaatga tgacagtgag tatgtgaggg ctgtgtacag gatgagtgag atgatcttca 2580
ggaggatcaa gatgcctgg ctgtggctgg acctgtggta cctgatgttc aaggagggct 2640
gggagcacaa aaaagcctg cagatcctgc acaccttcac caacagtgtg attgctgaga 2700
gggccaatga tgatgaatgcc aatgaggact gcagggagag tggcagggc agtgcccca 2760
gcaagaacaa gaggagagcc ttcctggacc tgctgctgag tgtgacagat gatgagggca 2820
acaggctgag ccatgaggac aatcaggagg aggtggacac cttcatgtt gagggccatg 2880
acaccacagc tgcagctatc aactggagcc tgtacctgcc gggcagcaac cctgaggtgc 2940
agaagaaggt ggaccatgag ctggatgatg tgtttggcaa gagtgacagg cctgccacag 3000
tggaggacct gaagaagctg aggtacctgg agtgtgtgat caaggagacc ctgaggctgt 3060
tccccagtgt gccctgtttt gccaggagtg tgtctgagga ctgtgaggtg gctgctaca 3120
gggtgctgaa gggcacagag gctgtgatca tccccatgc cctgcacagg gaccccaggt 3180
acttccccaa ccctgaggag ttccagcctg agaggttctt ccctgagaat gcccagggca 3240
ggcaccccta tgcctatgtg cccttcagtg ctggcccagg aactgcatt ggccagaagt 3300
ttgctgtgat ggaggagaag accatcctga gctgcatcct gaggccactc tggattgaga 3360
gcaaccagaa gagggaggag ctgggcctgg agggccagct gatcctgagg cccagcaatg 3420
gcatctggat caagctgaag aggaggaatg ctgatgagag gtgagaattc aatcaacctc 3480
tggattacaa aatttgtgaa agattgactg gtattcttaa ctatgttgct ccttttacgc 3540
tatgtggata cgctgcttta atgccttgt atcatgctat tgcttcccgt atggctttca 3600
ttttctcctc cttgtataaa tcctggttgt tgtctcttta tgaggagttg tgcccgttgt 3660
tcaggcaacg tggcgtggtg tgcactgtgt ttgctgacgc aacccccact ggttgggca 3720
ttgccaccac ctgtcagctc ctttccggga ctttcgcttt ccctccct attgccacgg 3780
cggaactcat cgccgcctgc cttgcccgct gctggacagg ggctcggctg ttgggcactg 3840
acaattccgt ggtgttgtcg gggaaatcat cgtcttttcc ttggctgctc gcctgtgttg 3900
ccacctggat tctgcgcggg acgtccttct gctacgtccc ttcggccctc aatccagcgg 3960
accttccttc ccgcggcctg ctgccggctc tgcggcctct tccgcgtctt cgccttcgcc 4020
ctcagacgag tcggatctcc ctttgggccg cctccccgcg tttattgcag cttataatgg 4080
ttacaaataa agcaatagca tcacaaattt cacaaatttt cagtttttt cactgcattc 4140
tagttgtggt ttgtccaaac tcatcaatgt atcttagcgg ccgcaggaac ccctagtgat 4200
ggagttggcc actccctctc tgcgcgctcg ctcgctcact gaggccgggc gaccaaaggt 4260
cgcccgacgc ccgggctttg cccggcggc tcagtgagc gagcgagcgc gcagctgcct 4320
gcagg                                                               4325
SEQ ID NO: 27         moltype = DNA  length = 4325
FEATURE               Location/Qualifiers
source                1..4325
                      mol_type = other DNA
                      organism = synthetic construct
SEQUENCE: 27
cctgcaggca gctgcgcgct cgctcgctca ctgaggccgc ccgggcgtcg ggcgaccttt 60
ggtcgcccgg cctcagtgag cgagcgagcg cgcagagagg gagtgccaa ctccatcact 120
aggggttcct gcggcctcta gactcgagac gcgttgacat tgattattga ctagttatta 180
atagtaatca attacggggt cattagttca tagcccatat atggagttcc gcgttacata 240
acttacggta aatggcccgc ctggctgacc gcccaacgac ccccgcccat tgacgtcaat 300
aatgacgtat gttcccatag taacgccaat agggactttc cattgacgtc aatgggtgga 360
ctatttacgg taaactgccc acttggcagt acatcaagtg tatcatatgc caagtacgcc 420
ccctattgac gtcaatgacg gtaaatggcc cgcctggcat tatgcccagt acatgacctt 480
atgggacttt cctacttggc agtacatcta cgtattagtc atcgctatta ccatgggtcg 540
aggtgagccc cacgttctgc ttcactctcc ccatctcccc ccctccccac ccccaatttt 600
gtatttattt attttttaa ttatttttgt gcagcgatgg gggcggggg gggggggcgc 660
gcgccaggcg gggcggggcg gggcgagggg cggggcgggg cgaggcggag aggtgcggcg 720
gcagccaatc agagcggcgc gctccgaaag ttttccttta ggcgaggcg gcggcggcgg 780
cggccctata aaagcgaag cgcgcggcgg gcggagtcg ctgcgttgcc ttcgccccgt 840
gccccgctcc gcgccgcctc gcgccgcccg ccccggctct gactgaccgc gttactccca 900
caggtgagcg ggcgggacgg cccttctcct ccgggctgta attagcgctt ggtttaatga 960
cggctcgttt cttttctgtg gctgcgtgaa agccttaaag gctccggga gggccctttg 1020
tgcgggggg agcggctcgg gggtgcgtg cgtgtgtgtg tgcgtgggga gcgccgcgtg 1080
cggcccgcgc tgcccggcgg ctgtgagcgc tgcgggcgcg gcgcggggct ttgtgcgctc 1140
cgcgtgtgcg cgagggagc gcggccgggg cggtgccccc gcggtgcggg gggctgcga 1200
gggaacaaa ggctgcgtgc ggggtgtgtg cgtgggggg tgagcagggg gtgtgggcgc 1260
```

```
ggcggtcggg ctgtaacccc cccctgcacc cccctcccccg agttgctgag cacggcccgg   1320
cttcgggtgc ggggctccgt acggggcgtg gcgcggggct cgccgtgccg ggcgggggt    1380
ggcggcaggt gggggtgccg ggcggggcgg ggccgcctcg ggccggggag ggctcggggg   1440
aggggcgcgg cggcccccgg agcgccggcg gctgtcgagg cgcggcgagc cgcagccatt   1500
gccttttatg gtaatcgtgc gagagggcgc agggacttcc tttgtcccaa atctgtgcgg   1560
agccgaaatc tgggaggcgc cgccgcaccc cctctagcgg gcgcggggcg aagcggtgcg   1620
gcgccggcag gaaggaaatg ggcggggagg ggccttcgtgc gtcgccgcgc cgccgtcccc  1680
ttctccatct ccagcctcgg ggctgtccgc aggggggacgg ctgccttcgg ggggacgggg  1740
gcagggcggg gttcggcttc tggcgtgtga ccggcggctc tagtgcctct gctaaccatg   1800
ttcatgcctt cttctttttc ctacagctcc tgggcaacgt gctggttatt gtgctgtctc   1860
atcattttgg caaaaagctt gccaccatgg ctggcctgtg gctggggctg gtctggcaga   1920
agctgctcct gtggggggct gcctcagccc tctccctggc tggggctagc ctggtgctga   1980
gcctgctgca gagagtggct agctatgcta gaaagtggca gcagatgaga cccatcccca   2040
cagtggctag agcctacccc ctggtgggcc atgccctgct gatgaagcct gatggcagag   2100
agttctttca gcagatcatt gagtacacag aggagtacag acacatgccc ctgctgaagc   2160
tgtgggtggg ccctgtgcct atggtagcac tgtacaatgc tgagaatgtg gaggtgatcc   2220
tgacaagcag caagcagatt gacaagagca gcatgtacaa gttcctggag ccctggctgg   2280
gcctgggcct gctgacaagc actgccaaca gtggagaag cagaagaaag atgctgaccc    2340
ccaccttcca cttcaccatc ctggaggact tcctggacat catgaatgag caagccaaca   2400
tcctggtgaa gaagctggag aagcacatca accaagaggc cttcaactgc ttcttctaca   2460
tcaccctgtg tgccctggat atcatctgtg agacagccat gggcaagaac attggggctc   2520
agagcaatga tgacagtgag tatgtgagag ctgtgtacaa aatgagtgag atgatcttca   2580
gaagaatcaa gatgcctgg ctgtggctgg acctgtggta cctgatgttc aaggagggct   2640
gggagcacaa gaagagcctg cagatcctgc acaccttcac caactctgtg attgctgaga   2700
gagccaatga gatgaatgcc aatgaggact gcagaggga tggcagaggc agtgccccta   2760
gcaagaacaa gagaagagcc ttcctggacc tgctcctgtc agtgacagat gatgagggca   2820
acagactgag ccatgaggac atcagagaag aggtggacac cttcatgttt gagggccatg   2880
acaccacagc tgctgccatc aactggagcc tgtacctgct gggcagcaac cctgaggtgc   2940
agaagaaggt ggaccatgag ctggatgatg tgtttggcaa gagtgacaga cctgccacag   3000
tggaggacct gaagaagctg agatacctgg agtgtgtgat caaggagccc ctgagactgt   3060
tcccctcagt gccccctgtt gctagaagtg tgagtgagga ctgtgaggtg gctggctaca   3120
gagtgctgaa gggcacagag gctgtgatca tcccctatgc cctgcacaga ccctagat    3180
acttccccaa ccctgaggag tttcagcctg agagattctt ccctgagaat gcccaaggca   3240
gacacccta tgcctatgtg cccttcagtg ctggccctag aaactgcatt gggcagaagt   3300
ttgctgtgat ggaggagaag accatcctga gctgcacttc tggattgaga                3360
gcaatcagaa gagagaggag ctgggcctgg aggggcagct gatcctgaga cctagcaatg   3420
gcatctggat caagctgaag agaagaaatg ctgatgagag atgagaattc aatcaacctc   3480
tggattacaa aatttgtgaa agattgactg gtattcttaa ctatgttgct ccttttacgc   3540
tatgtggata cgctgcttta atgcctttgt atcatgctat tgcttcccgt atggctttca   3600
ttttctcctc cttgtataaa tcctggttgc tgtctcttta tgaggagttg tggcccgttg   3660
tcaggcaacg tggcgtggtg tgcactgtgt ttgctgacgc aaccccact ggttgggca    3720
ttgccaccac ctgtcagctc ctttccggga cttttcgctt tccccctcct attgccacgg   3780
cggaactcat cgccgcctgc cttgccctgc gctggacagg ggctcggctg ttgggcactg   3840
acaattccgt ggtgttgtcg gggaaatcat cgtcctttcc ttggctgctc gcctgtgttg   3900
ccacctggat tctgcgcggg acgtcctctt gctacgtccc ttcggccctc aatccagcgg   3960
accttccttc ccgcggcctg ctgccggctc tgcggcctct tccgcgtctt cgccttcgcc   4020
ctcagacgag tcggatctcc ctttgggccg cctccccgc ttatggcgtt gtataatgg    4080
ttacaaataa agcaatagca tcacaaattt cacaaataaa gcatttttt cactgcattc   4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccggcggc ctcagtgagc gagcgagcgc gcagctgcct   4320
gcagg                                                                4325
```

SEQ ID NO: 28         moltype = DNA   length = 4325
FEATURE               Location/Qualifiers
source                1..4325
                      mol_type = other DNA
                      organism = synthetic construct
SEQUENCE: 28

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gactgagac gcgttgacat tgattattga ctagttatta    180
atagtaatca attacggggt cattagttca tagcccatat atggagttcc gcgttacata   240
acttacggta aatggcccgc ctggctgacc gcccaacgac ccccgcccat tgacgtcaat   300
aatgacgtat gttcccatag taacgccaat agggactttc cattgacgtc aatgggtgga   360
ctatttacgg taaactgccc acttggcagt acatcaagtg tatcatatgc caagtacgcc   420
ccctattgac gtcaatgacg gtaaatggcc cgcctggcat tatgcccagt acatgacctt   480
atgggacttt cctacttggc agtacatcta cgtattagtc atcgctatta ccatggtcg    540
aggtgagccc cacgttctgc ttcactctcc ccatctcccc ccctccccca cccccaattt   600
tgtatttatt tatttttttaa ttattttgtg cagcgatggg ggcggggggg gggggggcgc   660
gcgcaggcg gggcggggcg gggcgagggg cgggcgggg cggggcggag aggtgcggcg     720
gcagccaatc agagcggcgc gctccgaaag ttttcctttta ggcgaggcg gcggcggcgg   780
cggccctata aaagcgaag cgcgcggcgg gcgggagtcg ctgcgttgcc ttcgccccgt    840
gccccgctcc gccgccgctc gcgccgcccg gactgaccgc gttactccca                900
caggtgagcg ggcgggacgg ccctttctcct ccgggctgta attagcgctt ggtttaatga   960
cggcctcgttt cttttttctgtg gctgcgtgaa agccttaaag gctccgggga gggcccttttg  1020
tgcgggggggg agcggctcgg ggggtgcgtg cgtgtgtgtg tgcgtgggga gcgccgcgtg   1080
cggccccgcgc tgcccggcgg ctgtgagcgc tgcgggcgcg gcgcggggct ttgtgcgctc   1140
cgcgtgtgcg cgaggggagc gcggccgggg cggtgcccg cggtgcggg gggctgcga     1200
```

-continued

```
ggggaacaaa ggctgcgtgc ggggtgtgtg cgtgggggg tgagcagggg gtgtgggcgc  1260
ggcggtcggg ctgtaacccc ccctgcacc ccctccccg agttgctgag cacggcccgg  1320
cttcgggtgc ggggctccgt acggggcgtg gcgcggggct cgccgtgccg ggcgggggt  1380
ggcggcaggt gggggtgccg ggcggggcgg ggccgcctcg ggccggggag ggctcggggg  1440
aggggcgcgg cggccccgg agcgccggcg gctgtcgagg cgcggcgagc cgcagccatt  1500
gccttttatg gtaatcgtgc gagagggcgc agggacttcc tttgtcccaa atctgtgcgg  1560
agccgaaatc tgggaggcgc cgccgcaccc cctctagcgg gcgcggggcg aagcggtgcg  1620
gcgccggcag gaaggaaatg ggcggggagg gccttcgtgc gtcgccgcgc cgccgtcccc  1680
ttctccatct ccagcctcgg ggctgtccgc aggggacgg ctgccttcgg gggggacggg  1740
gcagggcggg gttcggcttc tggcgtgtga ccggcggctc tagtgcctct gctaaccatg  1800
ttcatgcctt cttctttttc ctacagctcc tgggcaacgt gctggttatt gtgctgtctc  1860
atcattttgg caaaaagctt gccaccatgg ctggactgtg gctgggcctg tgtgtggaga  1920
agctgctgct gtggggagct gccagtgctc tgtctctggc tggagcctcc ctggtgctga  1980
gcctgctgca gagggtgggcc tcctatgcca gaaagtggca gcagatgagg cccatcccca  2040
cagtggccag ggcctaccct ctggtgggcc atgctctgct gatgaagcct gatggcaggg  2100
agttttccca gcagatcatt gagtacacag aggagtacag gcacatgccc ctgctgaagc  2160
tgtgggtggg ccctgtgcct atggtggccc tgtacaatgc tgagaatgtg gaggtcattc  2220
tgacatcctc caagcagatt gataagtcct ccatgtacaa gtttctggag ccttggctgg  2280
gcctgggcct gctgacaagc acaggcaata gtggaggag caggagaaag atgctgaccc  2340
ctaccttca ctttacaatc ctggaggact ttctggatat catgaatgag caggccaaca  2400
tcctggtgaa gaagctggag aagcacatca accaggaggc cttcaattgt ttcttctaca  2460
tcacactgtg tgccctggac atcatctgtg agacagccat gggcaagaat attggagccc  2520
agtccaatga tgattctgag tatgtgaggg ctgtgtacag gatgagtgag atgatcttta  2580
ggagaatcaa gatgccctgg ctgtggctgg acctgtggta cctgatgttt aaggagggct  2640
gggagcacaa gaagagcctg cagatcctgc acacattcac aaattctgtg attgctgaga  2700
gagccaatga tgaatgcc aatgaggact gtagaggaga tgcagggggc tctgccccct  2760
ctaagaataa gaggagggcc ttcctgacc tgctgctgtc tgtgacagat gatgagggca  2820
ataggctgtc ccatgaggat atcagggagg aggtggacac cttcatgttt gagggccatg  2880
acacaacagc tgctgccatc aactggaacc tgtacctgct gggcagcaat cctgaggtgc  2940
agaagaaggt ggatcatgag tggatgatg tgtttgacaa gagtgacaga ctgccacacg  3000
tggaggatct gaagaagctg agatacctgg agtgtgtgat caaggagaca ctgagactgt  3060
tcccttctgt gccctgttt gccagaagtg tgtctgagga ctgtgaggtg gctggctaca  3120
gagtgctgaa gggcacagag gctgtgatca tccctatgc cctgcacagg atcctagat  3180
acttccctaa ccctgaggag ttccagcctg agaggttcct cctgagaat gcccagggca  3240
ggcaccccta tgcctatgtg cccttcagtg ctggccctag gaactgtatt ggcagaagt  3300
ttgctgtgat ggaggagaag accatcctgt cctgcatcct gagacacttc tggattgagt  3360
ccaaccagaa gagggaggag ctgggcctgg agggccagct gatcctgaga cctagcaatg  3420
gcatctggat caagctgaag agaagaaatg ctgatgagag atgaaattc aatcaacctc  3480
tggattacaa aatttgtgaa agattgactg gtattcttaa ctatgttgct cctttttacgc  3540
tatgtggata cgctgcttta atgcctttgt atcatgctat tgcttcccgt atggctttca  3600
ttttctcctc cttgtataaa tcctggttgc tgtctcttta tgaggagttg tgggcccgttg  3660
tcaggcaacg tggcgtggtg tgcactgtgt ttgctgacgc aaccccact ggttgggca  3720
ttgccaccac ctgtcagctc cttttcggga ctttcgcttt attgccacgg  3780
cggaactcat cgccgcctgc cttgcccgct gctggacagg ggctcggctg ttgggcactg  3840
acaattccgt ggtgttgtcg gggaaatcat cgtccttttcc ttggctgctc gcctgtgttg  3900
ccacctggat tctgcgcggg acgtccttct gctacgtccc ttcggccctc aatccagcgg  3960
accttcctc ccgcggcctc ctgccgctc tgccgtctt cgccttcgc  4020
ctcagacgag tcggatctcc ctttgggccg cctccccgcg tttattgcag cttataatgg  4080
ttacaaataa agcaatagca tcacaaattt cacaaataaa gcatttttt cactgcattc  4140
tagttgtggt ttgtccaaac tcatcaatgt atcttagcgg ccgcaggaac ccctagtgat  4200
ggagttggcc actccctctc tgcgcgctcg ctcgctcact gaggccgggc gaccaaaggt  4260
cgcccgacgc ccgggctttg cccgggcggc ctcagtgagc gagcgagcgc gcagctgcct  4320
gcagg                                                             4325
```

```
SEQ ID NO: 29         moltype = DNA  length = 4325
FEATURE               Location/Qualifiers
source                1..4325
                      mol_type = other DNA
                      organism = synthetic construct
SEQUENCE: 29
cctgcaggca gctgcgcgct cgctcgctca ctgaggccgc ccgggcgtcg ggcgaccttt   60
ggtcgcccgg cctcagtgag cgagcgagcg cgcagagagg gagtgccaa ctccatcact  120
aggggttcct gcggcctcta gactcgagac gcgttgacat tgattattga ctagttatta  180
atagtaatca attacggggt cattagttca tagcccatat atggagttcc gcgttacata  240
acttacggta aatggcccgc ctggctgacc gcccaacgac ccccgcccat tgacgtcaat  300
aatgacgtat gttcccatag taacgccaat agggactttc cattgacgtc aatgggtgga  360
ctatttacgg taaactgccc acttggcagt acatcaagtg tatcatatgc caagtacgcc  420
ccctattgac gtcaatgacg gtaaatggcc cgcctggcat tatgcccagt acatgacctt  480
atgggacttt cctacttggc agtacatcta cgtattagtc atcgctatta ccatgggtcg  540
aggtgagccc cacgttctgc ttcactctcc ccatctcccc cccctcccca ccccaatttt  600
tgtatttatt tattttttaa ttattttgtg cagcgatggg ggcgggggg gggggggcgc  660
gcgccaggcg gggcggggcg gggcgagggg cgggcgggg cgaggcggag aggtgcggcg  720
gcagccaatc agagcggcgc gctccgaaag ttttccttt ggcgaggcg gcggcggcgg  780
cggccctata aaaagcgaag cgcgcggcgg gcgggagtgg gttgcgtgc ttcgcccag  840
gccccgctcc gcgccgcctc gcgccgcccg cccggctct gactgaccgc gttactccca  900
caggtgagcg gcgggacgg ccctctcct ccggctgta attagcgctt ggtttaatga  960
cggctcgttt ctttctgtg gctgcgtgaa agccttaaag ggctccggga gggcccttttg  1020
tgcggggggg agcggctcgg ggggtgcgtg cgtgtgtgtg tgcgtgggga gcgccgcgtg  1080
cggccccgcc tgcccggcgg ctgtgagcgc tgcgggcgcg gcgcggggct ttgtgcgctc  1140
```

```
cgcgtgtgcg cgaggggagc gcggccgggg gcggtgcccc gcggtgcggg ggggctgcga    1200
ggggaacaaa ggctgcgtgc ggggtgtgtg cgtgggggggg tgagcagggg gtgtgggcgc    1260
ggcggtcggg ctgtaacccc ccctgcacc ccctcccg agttgctgag cacggcccgg       1320
cttcgggtgc ggggctccgt acgggcgtg gcgcggggct cgccgtgccg ggcgggggt       1380
ggcggcaggt gggggtgccg ggcggggcgg ggccgcctcg gggcggggcg ggctcggggg    1440
aggggcgcgg cggcccccgg agcgccggcg gctgtcgagg cgcggcgagc cgcagccatt    1500
gccttttatg gtaatcgtgc gagagggcgc agggacttcc tttgtcccaa atctgtgcgg    1560
agccgaaatc tgggaggcgc cgccgcaccc cctctagcgg gcgcggggcg aagcggtgcg    1620
gcgccggcag gaaggaaatg ggcggggagg gccttcgtgc gtcgccgcgc cgccgtcccc    1680
ttctccatct ccagcctcgg ggctgtccgc aggggacgg ctgccttcgg tggcttcggt      1740
gcagggcggg gttcggcttc tggcgtgtga ccggcggctc tagtgcctct gctaaccatg    1800
ttcatgcctt cttcttttc ctacagctcc tgggcaacgt gctggttatt gtgctgtctc      1860
atcattttgg caaaaagctt gccaccatgg caggactgtg gctgggactg gtgtggcaga    1920
agctgctgct gtggggagca gcaagtgccc tgtccctggc aggagcctcc ctggtgctgt    1980
ctctgctgca gagggtggca agctatgcaa ggaagtggca gcagatgagg cccatcccta    2040
cagtggcaag agcatatcca ctggtgggac atgcactgct gatgaagcct gatggcaggg    2100
agttctttca gcagatcatt gagtacacag aggagtatag gcacatgcca ctgctgaagc    2160
tgtgggtggg accagtgcca atggtggccc tgtacaatgc tgagaatgtg gaagtgatcc    2220
tgaccagctc caagcagatt gataagtcta gcatgtataa gttcctggag ccttggctgg    2280
gactgggact gctgacctcc acaggcaaca agtggaggtc taggagaaag atgctgaccc    2340
caacattcca ctttacaatc ctggaggact tcctggatat catgaatgag caggccaata    2400
tcctggtgaa gaagctggag aagcacatca accaggaggc cttaattgc ttcttctaca     2460
tcaccctgtg tgcccgggac atcatctgtg agacagccag ggcaagaac attggagccc      2520
agagcaatga tgattctgag tatgtgaggg ctgtgtatag gatgtctgag atgatcttta    2580
ggaggatcaa gatgccctgg ctgtggctgg atctgtggta tctgatgttc aaggagggct    2640
gggagcacaa gaagagcctg cagatcctgc acaccttcaa aaactctgtg attgctgaga    2700
gggccaatga gatgaatgcc aatgaggact gtaggggaga tggaagaggc tctgcccta    2760
gcaagaacaa gaggagagcc ttcctggacc tgctgctgtc tgtgacagat gatgagggca    2820
atagactgag ccatgaggac atcagggagg aggtggac attcatgttt gagggacatg      2880
acaccacagc agcagccatc aactggtctc tgtacctgct gggcagcaat ccagaggtgc    2940
agaagaaggt ggatcatgag ctggatgatg tgtttggcaa gagtgacaga cctgccacag    3000
tggaggatct gaagaagctg aggtacctgg agtgtgtgat caaggagaca ctgagactgt    3060
tcccctctgt gcctctgttt gccaggtctg tgtctgagga ctgtgaggtg gctggctata    3120
gggtgctgaa gggcacagag gctgtgatca tcccttatgc cctgcacagg gacccccagat    3180
atttccctaa cccagaggag tttcagccag agaggttctt cccagagaat gcacagggca    3240
ggcacccta tgcctatgtg ccattctctg ctggaccaag gaactgcatt ggacagaagt    3300
ttgctgtgat ggaggagaag accatcctgt cctgtatcct gaggcacttc tggattgagt    3360
ctaatcagaa gaggaggag ctgggactgg agggacagct gatcctgaga ccctccaatg      3420
gcatctggat caagctgaag aggaggaatg ctgatgagg gtgagaattc aatcaacctc    3480
tggattacaa aatttgtgaa agattgactg gtattcttaa ctatgttgct ccttttacgc    3540
tatgtggata cgctgcttta atgcctttgt atcatgctat tgcttcccgt atggctttca    3600
ttttctcctc cttgtataaa tcctggttgc tgtctcttta tgaggagttg tggcccgttg    3660
tcaggcaacg tggcgtggtg tgcactgtgt ttgctgacgc aaccccact ggttgggca     3720
ttgccaccac ctgtcagctc ctttccggga ctttcgcttt ccccctccct attgccacgg     3780
cggaactcat cgccgcctgc cttgcccgct gctggacagg ggctcggctg ttgggcactg    3840
acaattccgt ggtgttgtcg gggaaatcat cgtccttcc ttggctgctc gcctgtgttg     3900
ccacctggat tctgcgcggg acgtccttct gctacgtccc ttcggccctc aatccagcgg    3960
accttccttc ccgcggcctg ctgccggctc tgcggcctct tccgcgtctt cgccttcgcc    4020
ctcagacgag tcggatctcc ctttgggccg cctccccgcg tttattgcag cttataatgg    4080
ttacaaataa agcaatagca tcacaaattt cacaaataaa gcatttttt cactgcattc    4140
tagttgtggt ttgtccaaac tcatcaatgt atcttagcgg ccgcaggaac cctagtgat    4200
ggagttggcc actccctctc tgcgcgctcg ctcgctcact gaggccgggc gaccaaaggt   4260
cgcccgacgc ccgggctttg cccgggcggc ctcagtgagc gagcgagcgc gcagctgcct   4320
gcagg                                                              4325
```

SEQ ID NO: 30            moltype = DNA   length = 4325
FEATURE                  Location/Qualifiers
source                   1..4325
                         mol_type = other DNA
                         organism = synthetic construct SEQUENCE: 30
```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact   120
aggggttcct gcggcctcta gactcgagac gcgttgacat tgattattga ctagttatta   180
atagtaatca attacggggt cattagttca tagcccatat atggagttcc gcgttacata   240
acttacggta aatggcccgc ctggctgacc gcccaacgac ccccgcccat tgacgtcaat    300
aatgacgtat gttcccatag taacgccaat agggactttc cattgacgtc aatgggtgga   360
ctatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatgggtcg   540
aggtgagccc cacgttctgc ttcactctcc ccatctcccc ccctccca ccccaatttt     600
tgtatttatt tatttttaa ttatttgtg cagcgatggg ggcggggggg gggggggcgc    660
gcgccaggcg gggcggggcg gggcgagggg cgggcgggg cgaggcggag aggtgcggcg    720
gcagccaatc agagcggcgc gctccgaaag tttcttttg gcgggagtcg ctgcgttgcc     780
cggcccctata aaaagcgaag cgcgcggcgg cgggagtcg ctgcgttgcc ttcgccccgt   840
gccccgctcc gccgccgcctc gcgccgcccg cccggctct gactgaccgc gttactccca   900
caggtgagcg gcggcgacgg ccccttctcct ccgggctgta attagcgctt ggtttaatga   960
cggctcgttt cttttctgtg gctgcgtgaa agccttaaag ggctccggga gggccctttg   1020
tgcgggggg agcggctcgg ggggtgcgtg cgtgtgtgtg tgcgtgggga gcgccgcgtg    1080
```

```
cggcccgcgc tgcccggcgg ctgtgagcgc tgcgggcgcg gcgcggggct tgtgcgctc   1140
cgcgtgtgcg cgaggggagc gcggccgggg gcggtgcccc gcggtgcggg ggggctgcga   1200
gggaacaaa ggctgcgtgc ggggtgtgtg cgtggggggg tgagcagggg gtgtgggcgc    1260
ggcggtcggg ctgtaacccc cccctgcacc cccctcccg agttgctgag cacggcccgg    1320
cttcgggtgc ggggctccgt acggggcgtg gcgcggggct cgccgtgccg ggcgggggt    1380
ggcggcaggt gggggtgccg ggcggggcgg ggccgcctcg ggccgggag gggctcgggg    1440
aggggcgcgg cggcccccgg agccgccgcg gctgtcgagg cgcggcgagc cgcagccatt   1500
gccttttatg gtaatcgtgc gagagggcgc agggacttcc tttgtcccaa atctgtgcgg   1560
agccgaaatc tgggaggcgc cgccgcaccc cctctagcgg gcgcggggcg aagcggtgcg   1620
gcgccggcag gaaggaaatg ggcggggagg gccttcgtgc gtcgccgcgc cgccgtcccc   1680
ttctccatct ccagcctcgg ggctgtccgc aggggacgg ctgccttcgg ggggacggg     1740
gcagggcggg gttcggcttc tggcgtgtga ccggcggctc tagtgcctct gctaaccatg   1800
ttcatgcctt cttctttttc ctacagctcc tgggcaacgt gctggttatt gtgctgtctc   1860
atcattttgg caaaaagctt gccaccatgg ctgggctgtg gggggctg gtgtggcaga     1920
agctgctgct gtggggagct gctagtgccc tcagcctgtg tggagcaagc ctggtgctga   1980
gtctcctgca gagagtggcc tcctatgcca ggaagtggca acagatgagg cccatcccaa   2040
cagtggctag agcataccca ctggtgggcc atgccttgct gatgaagcct gatggcaggg   2100
agttctttca gcagatcatt gaatacactg aggagtacag acatgcctgc tgctgaagc    2160
tgtgggtggg cccagtgcct atggtggccc tctacaatgc tgagaatgtg gaagtgattc   2220
tgaccagtag caagcagatt gataagagta gcatgtacaa gttcctggag ccctggctgg   2280
ggttaggcct gctgaccagc acaggaaaca agtggaggag taggaggaag atgctgaccc   2340
ccaccttcca cttcaccatc ctggaggact tctgagcact tatgaatgaa caggcaaaca   2400
tcttggtgaa gaagctggag aagcacatta tcaggaggc cttcaactgc ttcttctata   2460
ttaccctgtg tgccctggat atcatctgtg agacagccat gggaaagaat attgagcccc   2520
agagtaatga tgactctgag tatgtgaggg ctgtgtacag aatgagtgag atgatcttca   2580
ggagaatcaa gatgccatgg ctgtggctgg acctgtgta gctgatgttc aaggaggggt    2640
gggagcacaa gaagtccctg cagattctgc acacctttac caacagtgtg attgctgaga   2700
gggcaatga tgatgaatgcc aatgaggatt gcaggggaga tggaagaggc tctgccccca    2760
gcaagaacaa aagaagggcc ttcctggacc tgctgttgtc tgtgactgat gatgaaggga   2820
acaggctgtc acatgaggac atcagagagg aggtggacac cttcatgttt gagggccatg   2880
acaccacagc tgctgccatt aactggagcc tgtacctgct gggaagcaac ccagaggtgc   2940
agaagaaggt ggaccatgag ctggatgatg tgtttggcaa gtcagacagg cctgccacag   3000
tggaggacct gaagaagctg aggtacctgg agtgtgtgat caaggaaaca ctgaggctgt   3060
tcccaagtgt gcctctgttt gccaggtctg tgtcagagga ctgtgaagtg gctgctaca    3120
gggtgctgaa gggaacagag gcagtgatca tcccatatgc actgacagag gaccctaggt   3180
attttcctaa ccctgaggag ttccagccag agaggttctt tcctgagaat gctcaggca    3240
ggcatcctta tgcctatgtg cctttctctg ctggccccag gaactgcatt ggccagaagt   3300
ttgctgtgat ggaagagaag accattttgt cctgtattc gaggcacttc tggattgaat   3360
ccaaccagaa gagggaggag ctgggccgga aagggcagct gatcctgagg ccctccaatg   3420
gcatttggat caaactgaag aggagaaatg ctgatgagag atgagaattc aatcaacctc   3480
tggattacaa aatttgtgaa agattgactg gtattcttaa ctatgttgct ccttttacgc   3540
tatgtggata cgctgcttta atgcctttgt atcatgctat tgcttcccgt atggctttca   3600
ttttcctcc cttgtataaa tcctggttgc tgtctcttta tgaggagttg tggcccgttg   3660
tcaggcaacg tggcgtggtg tgcactgtgt ttgctgacgc aacccccact ggttgggca    3720
ttgccaccac ctgtcagctc ctttccggga ctttcgcttt ccctctccct attgccacgg   3780
cggaactcat cgccgcctgc cttgcccgct gctggacagg ggctcggctg ttgggcactg   3840
acaattccgt ggtgttgtcg gggaaatcat cgtcctttc tggctgtc gcctgtgttg      3900
ccacctggat tctgcgcggg acgtcctct gctacgtccc ttcggccctc aatccagcgg    3960
accttccttc ccgcggcctg ctgccggctc tgcggcctct tccgcgtctt cgccttcgc    4020
ctcagacgag tcggatctcc ctttgggccg cctccccgcg tttattgcag cttataatgg   4080
ttacaaataa agcaatagca tcacaaattt cacaaataaa gcattttttt cactgcattc   4140
tagttgtggt ttgtccaaac tcatcaatgt atcttagcgg ccgcaggaac ccctagtgat   4200
ggagttggcc actccctct tgcgcgctcg ctcgctcact gaggccgggc gaccaaaggt    4260
cgcccgacgc ccgggctttg cccggcggc ctcagtgagc gagcgagcgc gcagctgcct    4320
gcagg                                                                4325
```

| SEQ ID NO: 31 | moltype = DNA length = 4325 |
|---|---|
| FEATURE | Location/Qualifiers |
| source | 1..4325 |
| | mol_type = other DNA |
| | organism = synthetic construct |

SEQUENCE: 31
```
cctgcaggca gctgcgcgct cgctcgctca ctgaggccgc ccggcgtcg ggcgacctttt    60
ggtcgcccgg cctcagtgag cgagcgagcg cgcagagggg gagtgccaa ctccatcact   120
aggggttcct gcggcctcta gactcgagac gcgttgacat tgattattga ctagttatta   180
atagtaatca attacggggt cattagttca tagcccatat atggagttcc gcgttacata   240
acttacggta aatggcccgc ctggctgacc gcccaacgac ccccgcccat tgacgtcaat   300
aatgacgtat gttcccatag taacgccaat agggactttc cattgacgtc aatgggtgga   360
ctatttacgg taaactgccc acttggcagt acatcaagtg tatcatatgc caagtacgcc   420
ccctattgac gtcaatgacg gtaaatggcc cgcctggcat tatgcccagt acatgacctt   480
atgggacttt cctacttggc agtacatcta cgtattagtc atcgctatta ccatgggtcg   540
aggtgagccc cacgttctgc ttcactctcc ccatctcccc ccctcccca cccccaattt   600
tgtatttatt tattttttaa ttattttgtg cagcgatggg gcgggggg ggggggcgc      660
gcgccaggcg gggcggggcg gggcgagggg cgggcgggg agcgggcgag aggtgcgga    720
gcagccaatc agagcggcgc gctccgaaag tttccttta tggcgaggcg gcggcggcgg   780
cggccctata aaaagcgaag cgcgcggcgg cgggagtcg ctgcgttgcc ttcgcccgt     840
gccccgctcc gcgccgcctc gcgccgcccg cccggctct gactgaccgc gttactccca   900
caggtgagcg ggcgggacgg cccttctcct ccgggctgta attagcgctt ggtttaatga   960
cggctcgttt cttttctgtg gctgcgtgaa agccttaaag gctccgggga gggccctttg  1020
```

```
tgcgggggggg agcggctcgg ggggtgcgtg cgtgtgtgtg tgcgtgggga gcgccgcgtg   1080
cggcccgcgc tgcccggcgg ctgtgagcgc tgcgggcgcg gcgcggggct ttgtgcgctc   1140
cgcgtgtgcg cgaggggagc gcggccgggg gcggtgcccc gcggtgcggg ggggctgcga   1200
ggggaacaaa ggctgcgtgc ggggtgtgtg cgtgggggGG tgagcagggg gtgtgggcgc   1260
ggcggtcggg ctgtaacccc cccctgcacc ccctcccgcg agttgctgag cacggcccgg   1320
cttcgggtgc ggggctccgt acggggcgtg gcgcggggct cgccgtgccg ggcgggggt    1380
ggcggcaggt gggggtgccg ggcggggcgg ggccgcctcg ggccggggag ggctcggggg   1440
agggggcgcg cggccccggg agcgccggcg gctgtcgagg cgcggcgagc cgcagccatt   1500
gccttttatg gtaatcgtgc gagagggcgc agggacttcc tttgtcccaa atctgtgcgg   1560
agccgaaatc tgggaggcgc cgccgcaccc cctctagcgg gcgcggggcg aagcggtgcg   1620
gcgccggcag gaaggaaatg ggcggggagg gccttcgtgc gtcgccgcgc cgccgtcccc   1680
ttctccatct ccagcctcgg ggctgtccgc aggggacggg ctgccttcgg ggggacggg    1740
gcagggcggg gttcggcttc tggcgtgtga ccggcggctc tagtgcctct gctaaccatg   1800
ttcatgcctt cttctttttc ctacagtctt tgggcaacgt gctggtttatt gtgctgtctc   1860
atcattttgg caaaaagctt gccaccatgc tggcctgtg gctgggcctg tgtggcaga    1920
agctgctcct gtggggagct gcctctgccc tgtcccggc tggggctagc ctggtgctgt   1980
ctctgttgca gagagtggcc agctatgcca ggaagtggcc acagatgaga cccatcccca   2040
cagtggccag agcataccc ctggtgggcc atgccctgct gatgaagcct gatggcagag    2100
agttcttcca gcagatcatt gagtacacag aggaatacag acacatgcct ctgctgaagc   2160
tgtgggtggg ccctgtgcct atggtggctc tctacaatgc tgagaatgtg gaagtgatcc   2220
tgaccagcag caagcagatt gacaagtcta gcatgtacaa gttcctggag ccttggctgg   2280
gactgggact gctgaccagc acaggcaaca agtggaggag cagaagaaag atgctgacac   2340
ctaccttcca ctttaccatc ctggaagatt tcctggacat tatgaatgag caggccaaca   2400
tcctggtcaa gaagctggaa aagcacatca accaggaggc ttttaactgc ttcttctaca   2460
tcaccctgtg tgccctggac atcatctgtg agacagccat gggcaagaac attggagctc   2520
agagcaatga tgatagtgaa tatgttagag ctgtctcaga gatgagtgag atgatcttca   2580
ggagaatcaa gatgccctgg ctgtggctga atctgtggta cctgatgttc aaggaaggat   2640
gggagcacaa gaaaagcctg cagatcctgc acaccttcac caacagtgtg attgctgaga   2700
gagccaatga gatgaatgcc aatgaggact gtagaggaga tggcagggc agtgcccctt    2760
ctaagaacaa gagaagggcc ttcctggacc tgctgctgga tgttacagat gatgagggca   2820
atagactgtc tcatgaggat atcagagaag aggtggacac cttcatgttt ggagggccatg   2880
acactacagc tgctgctatt aactggtccc tgtacctgct gggcagcaac cctgaagtgc   2940
agaagaaggt ggaccatgag ctggatgatg tgtttggaaa gagtgataga cctgccacag   3000
tggaagacct gaagaagcta aggtacctgg agtgtgtgat caaggaaaca ctgagactgt   3060
tccctctgt gcctctgttt gccagaagtg tgtctgagga ttgtgaggtg gctggctaca   3120
gggtgctgaa gggcacagag gctgtgatca tcccttatgc cctgcacagg gaccccagat   3180
atttccctaa ccctgaggag ttccagcctg agaggttctt cccagagaat gcccagggca   3240
gacatccta tgcctatgtg ccattcagtg ctggtcctag aaactgcatt ggccagaagt   3300
ttgctgtgat ggaagagaag accatcctga gctgcatcct gaggcacttc tggattgagt   3360
ctaatcagaa gagagaggaa ctgggcctgg aaggccagct gatcctcagg ccaagcaatg   3420
gcatctggat caagctgaag aggaggaatg ctgatgagag gtgagaattc aatcaacctc   3480
tggattacaa aatttgtgaa agattgactg gtattcttaa ctatgttgct ccttttacgc   3540
tatgtggata cgctgcttta atgcctttgt atcatgctat tgcttcccgt atggctttca   3600
tttttctcctc cttgtataaa tcctggttgc tgtctcttta tgaggagttg tgcccgttg    3660
tcaggcaacg tggcgtggtg tgcactgtgt ttgctgacgc aacccccact ggttggggca   3720
ttgccaccac ctgtcagctc ctttccggga cttttcgcttt cccctccct attgccacgg   3780
cggaactcat cgccgcctgc cttgcccgct gctggacagg ggctcggctg ttgggcactg   3840
acaattccgt ggtgttgtcg gggaaatcat cgtcctttcc ttggctgctc gcctgtgttg   3900
ccacctggat tctgcgcggg acgtccttct gctacgtccc ttcggccctc aatccagcgg   3960
accttccttc ccgcggcctg ctgccggctc tgcggcctct tccgcgtctt cgccttcgcc   4020
ctcagacgag tcggatctcc cttttgaccg cctccccgcc tttattgcag cttataatgg   4080
ttacaaataa agcaatagca tcacaaattt cacaaataaa gcatttttt cactgcattc    4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccgggcggc ctcagtgagc gagcgagcgc gcagctgcct   4320
gcagg                                                             4325
```

SEQ ID NO: 32       moltype = DNA   length = 4325
FEATURE             Location/Qualifiers
source              1..4325
                    mol_type = other DNA
                    organism = synthetic construct
SEQUENCE: 32

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gactgagac gcgttgacat tgattattga ctagttatta    180
atagtaatca attacggggt cattagttca tagcccatat atggagttcc gcgttacata    240
acttacggta aatggcccgc ctggctgacc gcccaacgac ccccgcccat tgacgtcaat    300
aatgacgtat gttcccatag taacgccaat agggactttc cattgacgtc aatgggtgga   360
ctatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatgggtcg   540
aggtgagccc cacgttctgc ttcactctcc ccatctcccc ccctcccca ccccaatttt    600
tgtatttatt tattttttaa ttattttgtg cagcgatggg gggcggggcg cgaggcggcg    660
gcgccaggcg ggggggggcg gggcgagggg cgggcgtggg gaggcgggag aggtgcggcg    720
gcagccaatc agagcggcgc gctccgaaag ttttccttta tggcgaggcg gcggcggcgg   780
cggccctata aaaagcgaag cgcgcggcgg cgggagtcg ctgcgttgcc ttcgcccgt     840
gccccgctcc gcgccgcctc gcgccgcccg cccggctct gactgaccgc gttactccca   900
caggtgagcg ggcgggacgg cccttctcct ccgggctgta attagcgctt ggtttaatga   960
```

```
cggctcgttt cttttctgtg gctgcgtgaa agccttaaag ggctccggga gggccctttg   1020
tgcgggggg  agcggctcgg ggggtgcgtg cgtgtgtgtg tgcgtgggga gcgccgcgtg   1080
cggcccgcgc tgcccggcgg ctgtgagcgc tgcgggcgcg gcgcggggct ttgtgcgctc   1140
cgcgtgtgcg cgaggggagc gcggccgggg gcggtgcccc gcggtgcggg ggggctgcga   1200
ggggaacaaa ggctgcgtgc ggggtgtgtg cgtggggggg tgagcagggg gtgtgggcgc   1260
ggcggtcggg ctgtaacccc ccctgcacc  ccctccccg  agttgctgag cacggcccgg   1320
cttcgggtgc ggggctccgt acggggcgtg gcgcggggct cgccgtgccg ggcgggggt    1380
ggcggcaggt ggggtgccg  ggcggggcgg ggccgcctcg ggccggggag ggctcggggg   1440
aggggcgcgg cggccccggg agcgccgcg  gctgtcgagg cgcgcgagc  cgcagccatt   1500
gccttttatg gtaatcgtgc gagagggcgc agggacttcc tttgtcccaa atctgtgcgg   1560
agccgaaatc tgggaggcgc cgccgcaccc cctctagcgg gcgcggggcg aagcggtgcg   1620
gcgccggcag gaaggaaatg gcgggggagg gccttcgtgc gtcgccgcgc cgccgtcccc   1680
ttctccatct ccagcctcgg ggctgtccgc aggggggacgg ctgccttcgg ggggggacggg  1740
gcagggcggg gttcggcttc tggcgtgtga ccggcggctc tagtgcctct gctaaccatg   1800
ttcatgcctt cttctttttc ctacagctcc tgggcaacgt gctggttatt gtgctgtctc   1860
atcatttttgg caaaaagctt gccaccatgg ctggactgtg gctgggactg gtgtggcaga   1920
aactgctgct ttggggagct gcctctgctc tgtctcttgc tggtgcttct ctggtgctga   1980
gcctgctgca gagagtggcc tcttatgcca gaaagtggca gcagatggga cccattccta   2040
cagtggccag agcctatcct cttgtggac  atgcccctgct gatgaagcct gatggcagag   2100
agttcttcca gcagatcatt gagtacacag aggaatacag gcacatgccc ctgctcaagc   2160
tgtgggttgg acctgtgcct atggtggccc tgtacaatgc tgagaatgtg gaagtgatcc   2220
tgaccagcag caagcagatt gacaagtcca gcatgcaaga gtttctggaa ccctggctgg   2280
gcctgggcct gctgacatct actgaaaca  agtggaggag caggaggaag atgctgaccc   2340
ctaccttcca ctttacaatt ctggaggact tcctggacat catgaatgag caggccaaca   2400
tcctggtcaa gaagctggaa aagcacatca atcaagaggc cttcaactgc ttcttctaca   2460
tcaccctgtg tgccctggat atcatctgtg agacagccat gggcaagaac attggagccc   2520
agagcaatga tgatagtgaa tatgtgaggg ctgtgtacag gatgagtgag atgatcttca   2580
ggaggatcaa gatgccttgg ctgtggctgg acctgtggta tctgatgttc aaagaaggct   2640
gggagcacaa gaagtccctg cagatcctgc acaccttcac caacagtgtg attgctgaga   2700
gggccaatga gatgaatgcc aatgaagatt gcagaggaga tggcaggga  agtgccccta   2760
gcaagaacaa gagaagggcc ttcctggatc tgctgctgag tgtgacagat gatgagggca   2820
atagactgag ccatgaggac atcagagaag aggtggacac cttcatgttt gagggccatg   2880
atacaacagc tgctgccatc aattggagcc tgtacctgct gggcagcaac cctgaggtgc   2940
agaagaaggt ggaccatgag ctggatgatg tgtttggcaa gtctgataga cctgccacag   3000
tggaagatct gaagaagctg agataccggg aatgtgtgat caaagagaca ctgaggctgt   3060
tccctagtgt gccccgtgttt gccagaagtg tgtctgagga ttgtgaagtg gctggctaca   3120
gagtgctgaa gggaacagag gctgtgatca tcccctatgc tctgcacaga gatcccaggt   3180
acttccccaa tcctgaagag ttccagcctg agaggttctt cccagagaat gcccagggca   3240
gacaccccta tgcctatgtg ccattctctg ctggacctag gaactgcatt ggccagaagt   3300
ttgctgtgat ggaagagaaa accatcctga gctgtatcct gaggcacttc tggattgaga   3360
gcaaccagaa gagagaggaa ctgggcctgg agggacagct gattctgagg cctagcaatg   3420
gcatctggat caagctgaag aggagaaatg ctgatgagag gtgagaattc aatcaacctc   3480
tggattacaa aatttgtgaa agattgactg gtattcttaa ctatgttgct cctttttacgc   3540
tatgtggata cgctgcttta atgcctttgt atcatgctat gcttcccgt  atggctttca   3600
ttttctcctc cttgtataaa tcctggttgc tgtctcttta tgaggagttg tgggccgttg   3660
tcaggcaacg tggcgtggtg tgcactgtgt ttgctgacgc aacccccact ggttgggca   3720
ttgccaccac ctgtcagctc cttttccggga ctttcgcttt ccccctccct attgccacgg   3780
cggaactcat cgccgcctgc cttgcccgct gctggacagg ggctcggctg ttgggcactg   3840
acaattccgt ggtgttgtcg gggaaatcat cgtcctttcc ttggctgctc gcctgtgttg   3900
ccacctggat tctgcgcggg acgtccttct gctacgtccc ttcggccctc aatccagcgg   3960
accttccttc ccgcggcctg ctgccgctc  tgcggcctct tccgcgtctt cgccttcgcc   4020
ctcagacgag tcggatcctc ctttgggccg cctccccgcg tttattgcag cttataagcg   4080
ttacaaataa agcaatagca tcacaaattt cacaaataaa gcattttttt cactgcattc   4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccgggcggc ctcagtgagc gagcgagcgc gcagctgcct   4320
gcagg                                                              4325

SEQ ID NO: 33        moltype = DNA   length = 4325
FEATURE              Location/Qualifiers
source               1..4325
                     mol_type = other DNA
                     organism = synthetic construct
SEQUENCE: 33
cctgcaggca gctgcgcgct cgctcgctca ctgaggccgc ccgggcgtcg ggcgaccttt   60
ggtcgcccgg cctcagtgag cgagcgagcg cgcagagagg gagtgccaa  ctccatcact   120
aggggttcct gcgcctcta  gactcgagac gcgttgacat tgattattga ctagttatta   180
atagtaatca attacggggt cattagttca tagcccatat atggagttcc gcgttacata   240
acttacggta aatggcccgc ctggctgacc gcccaacgac ccccgcccat tgacgtcaat   300
aatgacgtat gttcccatag taacgccaat agggactttc cattgacgtc aatgggtgga   360
ctatttacgg taaactgccc acttggcagt acatcaagtg tatcatatgc caagtacgcc   420
ccctattgac gtcaatgacg gtaaatggcc cgcctggcat tatgcccagt acatgacctt   480
atgggacttt cctacttggc agtacatcta cgtattagtc atcgctatta ccatgggtcg   540
aggtgagccc cacgttctgc ttcactctcc ccatctcccc ccccctcccc acccccaattt   600
tgtatttatt tattttttaa ttattttgtg cagcgatggg ggcgggggg  gggggggcgc   660
gcgccaggcg gggcggggcg gggcgagggg cgggcgggg  cgaggcggag aggtgcggcg   720
gcagccaatc agagcggcgc gctccgaaag ttttccttttt ggcgaggcg gcggcggcgg   780
cggccctata aaaagcgaag cgcgcggcgg gcgggagtcg ctgcgttgcc ttcgccccgt   840
gccccgctcc gcgccgcctc gcgccgcccg ccccggctct gactgaccgc gttactccca   900
```

```
caggtgagcg ggcgggacgg cccttctcct ccgggctgta attagcgctt ggtttaatga   960
cggctcgttt cttttctgtg gctgcgtgaa agccttaaag ggctccggga gggccctttg  1020
tgcgggggggg agcggctcgg ggggtgcgtg cgtgtgtgtg tgcgtgggga gcgccgcgtg  1080
cggcccgcgc tgcccggcgg ctgtgagcgc tgcgggcgcg gcgcgggggct ttgtgcgctc  1140
cgcgtgtgcg cgaggggagc gcggccgggg gcggtgcccc gcggtgcggg gggctgcga   1200
ggggaacaaa ggctgcgtgc ggggtgtgtg cgtgggggggg tgagcagggg gtgtgggcgc  1260
ggcggtcggg ctgtaacccc ccctgcacc ccctccccg agttgctgag cacggcccgg   1320
cttcgggtgc ggggctccgt acgggcgtg gcgcggggct cgccgtgccg ggcgggggt   1380
ggcggcaggt gggggtgccg ggcggggcgg ggccgcctcg ggccggggag ggctcggggg  1440
aggggcgcgg cggccccgg agcgccggcg gctgtcgagg cgcgcgagc cgcagccatt  1500
gcctttatg gtaatcgtgc gagagggcgc agggacttcc tttgtcccaa atctgtgcgg  1560
agccgaaatc tgggaggcgc cgccgcaccc cctctagcgg gcgcggggcg aagcggtgcg  1620
gcgccggcag gaaggaaatg ggcggggagg gccttcgtgc gtcgccgcgc cgccgtcccc  1680
ttctccatct ccagcctcgg ggctgtccgc aggggacgg ctgccttcgg gggggacggg  1740
gcagggcggg gttcggcttc tggcgtgtga ccggcggctc tagtgcctct gctaaccatg  1800
ttcatgcctt cttcttttttc ctacagctcc tgggcaacgt gctggttatt gtgctgtctc  1860
atcattttgg caaaaagctt gccaccatgc tggactttg gctgggactg gtgtggcaga  1920
agctgctgct gtggggagct gctagtgccc tgagcctgcc tggagcttct cttgtgctga  1980
gcttactgca aagagtggcc agctatgcca gaaagtggca gcagatgaga cccatccca   2040
cagtggctag agcttatcct ctggtgggac atgctctgct gatgaagcct gatgaagag   2100
agttttttcca gcagatcatt gagtacacag aggagtacag acacatgccc ctgctgaagc  2160
tgtgggtggg cccagttcct atggtggctc tgtataatgt gaggtgatcc                 2220
tgaccagcag caagcagatt gacaagagca gcatgtacaa gttcctggaa ccctggctga  2280
gcctgggatt actgacatct acaggaaata aatggagaag cagaagaaag atgctgaccc  2340
ccaccttcca cttcaccatc ctggaggact tcctggacat catgaatgag caggccaaca  2400
tccgtggtgaa gaagctggag aagcacatca accaggagca cttcaactgc ttcttctaca  2460
tcaccctgtg tgccctggac atcatctgtg acagcagtat gggcaagaac attggagctc  2520
agagcaatga tgacagtgag tatgtgagag ctgtgtacag aatgagtgag atgatcttca  2580
gaagaatcaa gatgccctgg ctgtggctgg acctgtggta tctgatgttc aaggagggct  2640
gggagcacaa gaagagcctg cagatcctgc acacctttcaa caacagtgtg attgctgaga  2700
gagccaatga tgatgaatgcc aatgaggact gcagaggaga tggcagagga tctgctccta  2760
gcaaaaataa gagaagagcc ttcctggacc tgctgctgag tgtgacagat gatgaaggaa  2820
acagactgag ccatgaggac atcagagagg aggtggacac cttcatgttt gagggccatg  2880
acaccacagc tgctgctatt aattggagcc tgtatctgct gggaagcaac cctgaagtgc  2940
agaagaaggt ggaccatgag ctggatgatg tgtttggcaa gagtgacaga cctgccacag  3000
tggaggatct gaagaagctg agatacctgg agtgtgtgat caaggagacc ctgagctgt   3060
tccccagtgt gcccctgttt gctagatctg tgagtgaaga ttgtgaggtg gctggctata  3120
gagtgctgaa aggcacagaa gctgtgatca tccccctatgc tctgcacaga gacccagat   3180
acttcccaa ccctgaggag tttcagcctg agagattctt ccctgagaat gccaaggca   3240
gacacccta tgcttatgtg cccttcagtg ctggccccag aaattgcatt ggacagaagt   3300
ttgctgtgat ggaggagaag accatcctga gctgcatcct gagacacttc tggattgaga   3360
gcaaccagaa gagagaggag ctgggcctgg agggccaact gattctgaga cctagcaatg  3420
gcatctggat caagctgaag agaaggaaga ctgatgagag agaaattc aatcaacctc   3480
tggattacaa aatttgtgaa agattgactg gtattcttaa ctatgttgct cctttacgc   3540
tatgtggata cgctgcttta atgcctttgt atcatgctat tgcttcccgt atggctttca   3600
ttttctcctc cttgtataaa tcctggttgc tgtctcttta tgaggagttg tggcccgttg   3660
tcaggcaacg tggcgtggtg tgcactgtgt ttgctgacgc aaccccact ggttggggca   3720
ttgccaccac ctgtcagctc ctttccggga cttcgctttt cccctccct attgccacgg   3780
cggaactcat cgccgcctgc cttgcccgct gctggacagg ggctcggctg ttgggcactg   3840
acaattccgt ggtgttgtcg gggaaatcat cgtcctttcc ttggctgctc gcctgtgttg   3900
ccacctggat tctgcgcggg acgtccttct gctacgtccc ttcggccctc aatccagcgg   3960
accttcttc ccgcggcctg ctgccggctc tgcggcctct tccgcgtctt cgccttcgcc   4020
ctcagacgag tcggatctcc ctttgggccg cctccccgcg tttattgcag cttataatgg   4080
ttacaaataa agcaatagca tcacaaattt cacaaataaa gcattttttt cactgcattc   4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccgggcggc ctcagtgagc gagcgagcgc gcagctgcct   4320
gcagg                                                               4325

SEQ ID NO: 34           moltype = DNA   length = 4325
FEATURE                 Location/Qualifiers
source                  1..4325
                        mol_type = other DNA
                        organism = synthetic construct
SEQUENCE: 34
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact  120
agggggttcct gcggcctcta gactcgagac gcgttgacat tgattattga ctagttatta  180
atagtaatca attacggggt cattagttca tagcccatat atggagttcc gcgttacata  240
acttacggta aatggcccgc ctggctgacc gcccaacgac ccccgcccat tgacgtcaat  300
aatgacgtat gttcccatag taacgccaat agggactttc cattgacgtc aatgggtgga  360
ctatttacgg taaactgccc acttggcagt acatcaagtg tatcatatgc caagtacgcc  420
ccctattgac gtcaatgacg gtaaatggcc cgcctggcat tatgcccagt acatgacctt  480
atgggacttt cctacttggc agtacatcta cgtattagtc atcgctatta ccatgggtcg  540
aggtgagccc cacgttctgc ttcactctcc ccatctcccc ccctccccca ccccaatttt  600
tgtatttatt tattttttaa ttattttgtg cagcgatggg ggcggggggg gggggggcgc  660
gcgccaggcg gggcggggcg gggcgagggg cggggcgggg cgaggcggag aggtgcggcg  720
gcagccaatc agagcggcgc gctccgaaag tttcctttta tggcgaggcg gcggcggcgg  780
cggccctata aaaagcgaag cgcgcggcgg gcgggagtcg ctgcgttgcc ttcgcccgt   840
```

```
gccccgctcc gcgccgcctc gcgccgcccg ccccggctct gactgaccgc gttactccca    900
caggtgagcg ggcgggacgg cccttctcct ccgggctgta attagcgctt ggtttaatga    960
cggctcgttt cttttctgtg gctgcgtgaa agccttaaag ggctccggga gggccctttg   1020
tgcgggggggg agcggctcgg ggggtgcgtg cgtgtgtgtg tgcgtgggga gcgccgcgtg   1080
cggccgcgcg tgcccggcgg ctgtgagcgc tgcgggcgcg gcgcggggct ttgtgcgctc   1140
cgcgtgtgcg cgaggggagc gcggccgggg gcggtgcccc gcggtgcggg ggggctgcga   1200
ggggaacaaa ggctgcgtgc ggggtgtgtg cgtgggggggg tgagcagggg gtgtgggcgc   1260
ggcggtcggg ctgtaacccc cccctgcacc ccctccccg agttgctgag cacgccccgg    1320
cttcgggtgc ggggctccgt acggggcgtg gcgcggggct cgccgtgccg ggcgggggt    1380
ggcggcaggt ggggggtgccg ggcggggcgg ggcgcctcg ggccggggag ggctcggggg   1440
aggggcgcgg cggccccggg agcgccggcg gctgtcgagg cgcggcgagc cgcagccatt   1500
gccttttatg gtaatcgtgc gagagggcgc agggacttcc tttgtcccaa atctgtgcgg   1560
agccgaaatc tgggaggcgc cgccgcaccc cctctagcgg gcgcggggcg aagcggtgcg   1620
gcgccggcag gaaggaaatg ggcgggggagg gccttcgtgg gtcgccgcgc cgccgtcccc   1680
ttctccatct ccagcctcgg ggctgtccgc agggggacgg ctgccttcgg ggggggacggg   1740
gcagggcggg gttcggcttc tggcgtgtga ccggcggctc tagtgcctct gctaaccatg   1800
ttcatgcctt cttcttttttc ctacagctcc tgggcaacgt gctggttatt gtgctgtctc   1860
atcattttgg caaaaagctt gccaccatgg ctggactgtg atgtggcaga                1920
aactgctgct gtggggagct gcttctgcac tgtctctggc tggggcatct ctggtcctgt   1980
ccctgctgca gagagtggcc tcctatgcca gaaagtggca gcagatgaga cctatcccca   2040
cagtggccag ggcataccccc ctggtgggtc atgccctcct gatgaaacca gatgggaggg   2100
aatttttcca gcagattatt gagtacacag aagaatatag acacatgcct cctcaagc     2160
tgtgggttgg gcctgtccct atggttgccc tctataatga tgagaatgtt gaagttattc   2220
tcacatcatc taagcagatt gataagagta gcatgtataa gttctgttgaa ccctggctgg   2280
ggctggggct cctcacctca actgggaaca agtggaggtc tagaagaaaa atgctcaccc   2340
ccaccttcca tttcaccatc ctggaggact tctgcaact catgaatgag caggctaaca   2400
tcctggttaa aaaactgtgag aaacatatca atcaggaagc cttcaattgt ttcttctata   2460
ttactctctg tgctctggac attatctgtg agactgcaat gggaaagaat attggtgcac   2520
agtcaaatga tgattcagaa tatgtcaggg ctgtctacag aatgtctgag atgatcttta   2580
ggagaatcaa gatgccctgg ctgtggctgg atctgtgtga cctcatgttc aaggaaggat   2640
gggagcataa gaaaagtctg cagattctgc ataccttcac caactcagtg attgcagaga   2700
gagcaaatga gatgaatgct aatgaagatt gcagggggga tggaagggga agtgccccta   2760
gcaaaaataa gagaagggcc tttctggatc tcctcctgag tgttacagat gatgagggta   2820
atagactcag ccatgaagat atcagagaag aggtggacac attcatgttt gagggccatg   2880
atactactgc agcagctatt aactggagtc tgtacctgct gggctcaaac cctgaggttc   2940
agaagaaagt tgaccatgaa ctggatgatg tctttgggaa gtcagacagg cctgctactg   3000
tggaagatct gaagaagctg aggtacctgg agtgcgtcat taaggaaacc ctgagactct   3060
tcccctctgt ccccctgttt gctagatcag tttcagaaga ttgtgaggtg gctggctata   3120
gggtctgcaa gggtactgag gcagtgatta tcccttatgc tctccacagg gatcctaggt   3180
actttccaaa tcctgaggag ttccagcctg agagattttt cccagaaaat gcccagggca   3240
ggcatcccta tgcttatgtc cccttttagtg caggaccaag aaactgtatt ggccagaaat   3300
ttgcagtcat ggaggagaaa acaatcctgt cttgcatcct gaggcatttc tggattgaat   3360
ccaaccagaa aagagaggag ctgggactgg aagggcagct gattctgaga ccaagcaatg   3420
ggatttggat caagctgaag aggaggaatg cagatgagag gtaagaattc aatcaacctg   3480
tggattacaa aatttgtgaa agattgactg gtattcttaa ctatgttgct ccttttacgc   3540
tatgtggata cgctgcttta atgcctttgt atcatgctat tgcttcccgt atggctttca   3600
ttttctcctc cttgtataaa tcctggttgc tgtctcttta tgaggagttg tggcccgttg   3660
tcaggcaacg tggcgtggtg tgcactgtgt ttgctgacgc aaccccccact ggttgggca    3720
ttgccaccac ctgtcagctc cttccgggga ctttcgcttt ccccctccct attgccacgg   3780
cggaactcat cgccgcctgc cttgcccgct gctggacagg ggctcggctg ttgggcactg   3840
acaattccgt ggtgttgtcg gggaaatcat cgtccttttc ttggctgtcc gcctgtgttg   3900
ccacctggat tctgcgcggg acgtccttct gctacgtccc ttcggccctc aatccagcgg   3960
accttccttc ccgcggcctg ctgccggctc tgcggcctct tccgcgtctt cgccttcgcc   4020
ctcagacgag tcggatctcc ctttgggccg cctccccgcg tttattgcag cttataatgg   4080
ttacaaataa agcaatagca tcacaaattt cacaaataaa gcatttttt cactgcattc    4140
tagttgtggt ttgtccaaac tcatcaatgt atcttagcgg ccgcaggaac ccctagtgat   4200
ggagttggcc actccctctc tgcgcgctcg ctcgctcact gaggccgggc gaccaaaggt   4260
cgcccgacgc ccgggctttg cccggcggc ctcagtgagc gagcgagcgc gcagctgcct   4320
gcagg                                                                4325
```

SEQ ID NO: 35           moltype = DNA  length = 1671
FEATURE                 Location/Qualifiers
source                  1..1671
                        mol_type = other DNA
                        organism = synthetic construct
SEQUENCE: 35

```
gacattgatt attgactagt tattaatagt aatcaattac gggtcatta gttcatagcc      60
catatatgga gttccgcgtt acataactta cggtaaatgg cccgcctggc tgaccgccca    120
acgacccccg cccattgacg tcaataatga cgtatgttcc catgtaacg ccaataggga     180
ctttccattg acgtcaatgg gtggactatt tacggtaaac tgcccacttg gcagtacatc    240
aagtgtatca tatgccaagt acgccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtg agccccacgt tctgcttcac tctccccatc   420
tccccccccc ccccaccccc aattttgtat ttatttatt tttaattatt ttgtgcagcg    480
atgggggcgg gggggggggg ggcgcgcgcc aggcggggcg ggggcgggcg aggggcgggg   540
cggggcgagg cggagaggtg cggcggcagc caatcagagc ggcgcgctcc gaaagtttcc   600
ttttatggcg aggcggcggc ggcggcggcc ctataaaaag cgaagcgcgc ggcggcgggg   660
agtcgctgcg ttgccttcgc cccgtgcccc gctccgcgcc gcctcgcgcc gcccgcccccg   720
gctctgactg accgcgttac tcccacaggt gagcggcgcg gacggccctt ctcctccggg   780
```

```
ctgtaattag cgcttggttt aatgacggct cgtttctttt ctgtggctgc gtgaaagcct    840
taaagggctc cgggagggcc ctttgtgcgg ggggagcgg ctcgggggt gcgtgcgtgt    900
gtgtgtgcgt ggggagcgcc gcgtgcggcc cgcgctgccc ggcggctgtg agcgctgcgg    960
gcgcggcgcg gggctttgtg cgctccgcgt gtgcgcgagg ggagcgcggc cggggcggt   1020
gccccgcggt gcggggggc tgcgagggga acaaaggctg cgtgcggggt gtgtgcgtgg   1080
gggggtgagc aggggggtgtg ggcgcggcgg tcgggctgta acccccccct gcacccccct   1140
ccccgagttg ctgagcacgg cccggcttcg ggtgcgggc tccgtacggg gcgtggcgcg   1200
gggctcgccg tgccgggcgg ggggtggcgg caggtggggg tgccgggcgg ggcggggccg   1260
cctcgggcgg gggaggggctc ggggggagggg cgcggcggcc cccggagcgc cggcggctgg   1320
cgaggcgcgg cgagccgcag ccattgcctt ttatggtaat cgtgcgagag ggcgcaggga   1380
cttcctttgt cccaaatctg tgcggagccg aaatctggga ggcgccgccg caccccctct   1440
agcgggcgcg gggcgaagcg gtgcggcgcc ggcaggaagg aaatgggcgg ggagggcctt   1500
cgtgcgtcgc cgcgccgccg tcccttctc catctccagc ctcggggctg tccgcagggg   1560
gacggctgcc ttcgggggg acggggcagg gcggggttcg gcttctggcg tgtgaccggc   1620
ggctctagtg cctctgctaa ccatgttcat gccttcttct ttttcctaca g            1671

SEQ ID NO: 36            moltype = DNA   length = 2796
FEATURE                  Location/Qualifiers
source                   1..2796
                         mol_type = other DNA
                         organism = synthetic construct
SEQUENCE: 36
ctgcgcgctc gctcgctcac tgaggccgcc cgggcaaagc ccgggcgtcg ggcgaccttt     60
ggtcgcccgg cctcagtgag cgagcgagcg cgcagagagg gagtgggggtt aaacgttgac   120
attgattatt gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctcaa agcttgccgc caccatggcg gggctctggc tggggctcgt   780
gtggcagaag ctgctgctgt ggggccggcc gagtgccctt tcctggccg gcgccagtct   840
ggtcctgagc ctgctgcaga gggtggccag ctacggccag ccagggcagg aaatgcggcc   900
```

RECOMBINANT ADENO-ASSOCIATED VIRAL VECTORS FOR TREATING BIETTI CRYSTALLINE DYSTROPHY

FIELD OF THE INVENTION

The present disclosure provides an expression cassette and recombinant adeno-associated virus (rAAV) vector comprising a nucleic acid encoding CYP4V2. Also provided are viral particles comprising a rAAV vector, a composition comprising the viral particles, and uses thereof.

BACKGROUND

Recent progresses have demonstrated that gene therapy holds great promises in treating human genetic disorders[1]. Over 6,000 of inherited diseases have been described[2], the number of which is still increasing with further disclosure of genome sequencing techniques[3]. The discovery of safer delivering vectors and the revelation of new gene editing techniques in recent years significantly enhanced the toolbox for treating these genetic diseases, with which the deficient genes could either be supplemented by exogenetic DNAs that carried by a therapeutic vector or be corrected in situ permanently by gene editing[4]. Contrary to this promising prospect, the list of genetic disorders that are clinically treatable grows slowly[5]. A major limiting factor to this situation is the lack of human translatable animal models, which impeded the therapeutic effect evaluation of gene therapies[6].

Bietti Crystalline Dystrophy (BCD, MIM 210370) is an autosomal recessive inherited disease first described by the Italian ophthalmologist G. B. Bietti in 1937, which was named for its distinguishing yellow-white crystalline deposits observed in patient's fundus[7]. BCD is accounted for ~3% of all nonsyndromic retinitis pigmentosa (RP) and for ~10% of nonsyndromic autosomal recessive RP in Europe [8]. BCD also appears to be more common in East Asia, especially in China, where the genetic mutation frequency is estimated to be 1 in 20,000[9].

In 2000, it was identified that the genetic basis of BCD is associated with chromosome 4q35[8]. CYP4V2, a member of the cytochrome P450 superfamily, was identified as the disease-causing gene of BCD in 2004[10]. Besides the crystalline deposits in retina and cornea, altered fatty acid concentration was also found in the serum of BCD patients, which implied a dysregulation of lipid metabolism[11,12]. More importantly, BCD patients inevitably develop vision loss and night blindness between 20 and 40 years of age and eventually progress to legal blindness between the ages of 50 and 60[11]. Unfortunately, 80 years after the first discovery of BCD, there is still no treatment available for this severe blinding disease.

AAV has become a preferred delivery tool for gene therapies for treating genetic disorders such as BCD due to its demonstrated long-term transgene expression, selective tropism and non-pathogenic nature.

CN111733174B discloses a construct which can be packaged into AAV vectors and comprises both coding sequences of CYP4V2 and RdCVF for treating BCD. The construct comprises a CAG promoter and a BGH polyadenylation signal site.

CN109136266A also provides construct for expressing CYP4V2 by rAAV. In the packaging plasmid, a sequence encoding short peptide C9 is inserted to enable a specific binding to CD59 antigen on human RPE cell membrane. In addition, a sequence encoding HRH peptide is inserted along with the coding sequence of CYP4V2 to inhibit VEGF.

Both CN111733174B and CN109136266A use the wild type coding sequence of CYP4V2.

Accordingly, there is a need in the art for improved gene therapy compositions and methods that can efficiently and safely restore CYP4V2 gene function in BCD patients.

SUMMARY OF THE INVENTION

The present inventors have developed rAAV vectors comprising codon-optimized coding sequence of CYP4V2 and certain combinations of gene expression regulatory sequences, which achieved significantly enhanced expression levels (~26.1 times) as compared to the previously published form[13], thus completing the invention.

Therefore, in a first aspect, the present disclosure relates to an isolated nucleic acid molecule, comprising a nucleotide sequence selected from a group consisting of SEQ ID NOs: 2-17 and encoding human CYP4V2. In a more preferred embodiment, the nucleotide sequence is selected from SEQ ID NOs: 8, 9, 15, 16 and 17. In an even more preferred embodiment, the nucleotide sequence is SEQ ID NO: 8 or SEQ ID NO: 16. In the most preferred embodiment, the nucleotide sequence is SEQ ID NO: 16.

In an embodiment of the first aspect, the isolated nucleic acid molecule further comprises a promoter which is operatively linked to the 5' of the nucleotide sequence encoding CYP4V2. Preferably, the promoter is CAG promoter of SEQ ID NO: 35.

In one embodiment, the isolated nucleic acid molecule further comprises a polyadenylation sequence at the 3' of the nucleotide sequence encoding CYP4V2 polypeptide.

Preferably, the polyadenylation sequence is bovine growth hormone (bGH) polyA, synthesized polyA (SPA) or Simian Virus 40 (SV40) polyA, more preferably SV40 polyA.

In another embodiment, the isolated nucleic acid further comprises a Woodchuck Hepatitis Virus posttranscriptional regulatory element (WPRE) located between the CYP4V2 coding sequence and the SV40 polyA sequence.

In one preferred embodiment, the isolated nucleic acid molecule comprises
(a) a nucleotide sequence of any one of SEQ ID NOs: 18-34, or
(b) a nucleotide sequence having at least 85% homology, at least 90% homology, at least 95% homology, at least 96% homology, at least 97% homology, at least 98% homology, at least 99% homology to any one of SEQ ID NO: 18-34.

In a second aspect, the present disclosure provides a recombinant AAV (rAAV) vector comprising the nucleic acid molecule of the first aspect.

In one embodiment, the rAAV vector comprises at least one ITR, preferably two ITRs. In a preferred embodiment, the two ITRs are derived from AAV2 ITR.

In a third aspect, the present disclosure provides a viral particle comprising the recombinant AAV vector of the second aspect and AAV capsid selected from AAV1, AAV2, AAV4, AAV5, AAV7, AAV8, AAV9, AAVrh10, AAV2.7m8, AAVAnc80L65 and the variants thereof. Preferably, the capsid is AAV8.

In a fourth aspect, the present disclosure provides a pharmaceutical composition comprising the viral particle of the third aspect and a pharmaceutically acceptable excipient.

In a fifth aspect, the present disclosure provides use of the rAAV vector in the manufacture of a medicament for treating or preventing Bietti Crystalline Dystrophy (BCD) or any other diseases of retinal pigment epithelium (RPE) atrophy.

DETAILED DESCRIPTION OF THE INVENTION

Figure 1:
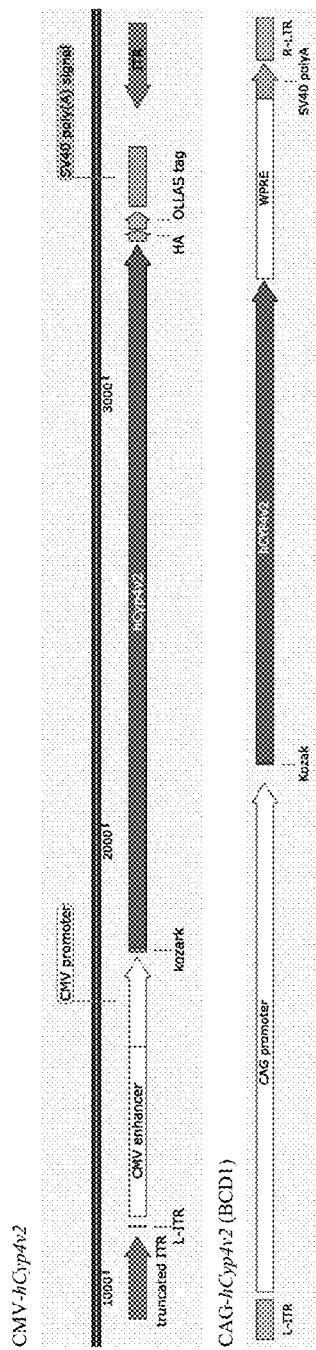
FIG. 1 is an illustrative diagram showing the constructs CMV-hCyp4v2 (upper panel) and CAG-hCyp4v2 (BCD1, lower panel).
Figure 2:
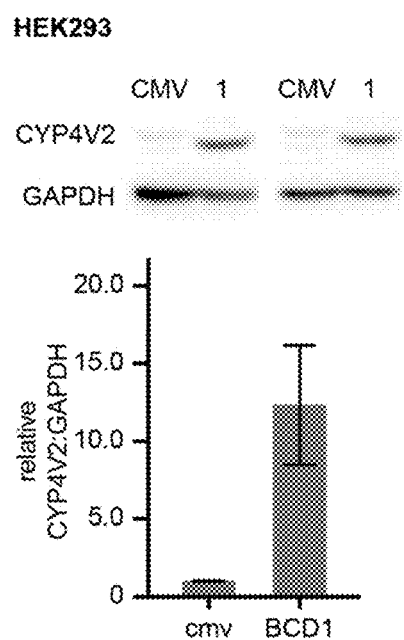
FIG. 2 is a histogram showing the CYP4V2 transgene protein expression levels of the construct CMV-hCyp4v2 in comparion with the construct CAG-hCyp4v2 (BCD1) in HEK293.

Unless specifically defined elsewhere in this document, all the technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

In the context of the present disclosure, unless being otherwise indicated, the wording "comprise", and variations thereof such as "comprises" and "comprising" will be understood to imply the inclusion of a stated element, e.g. an amino acid sequence, a nucleotide sequence, a property, a step or a group thereof, but not the exclusion of any other elements, e.g. amino acid sequences, nucleotide sequences, properties and steps. When used herein the term "comprise" or any variation thereof can be substituted with the term "contain", "include" or sometimes "have" or equivalent variation thereof. In certain embodiments, the wording "comprise" also include the scenario of "consisting of".

The abbreviation "CYP4V2" refers to cytochrome P450 family 4 subfamily V member 2, which is a gene coding for CYP4V2 protein of the cytochrome P450 hemethiolate protein superfamily involved in oxidizing various substrates in the metabolic pathway. Defects in the gene CYP4V2 are known to cause BCD and also fundus dystrophy. The CYP4V2 mentioned here refers to human CYP4V2 in the context of the present disclosure unless otherwise indicated. Isolated Nucleic Acid Encoding CYP4V2 Protein.

The present disclosure provides an isolated nucleic acid sequence comprising a nucleotide sequence coding for CYP4V2 protein, specifically human CYP4V2. By "isolated nucleic acid", it means a DNA or RNA which is removed from all or a portion of a polynucleotide in which the isolated polynucleotide is found in nature, or is linked to a polynucleotide to which it is not linked in nature. An isolated nucleic acid molecule "comprising" a specific nucleotide sequence may include, in addition to the specified sequence, operably linked regulatory sequences that control expression of the coding region of the recited nucleic acid sequences. Due to the codon degeneracy, one skilled in the art can understand that a specific amino acid sequence can be coded by different nucleotide sequences.

The nucleotide sequence coding for CYP4V2 of the present disclosure has been subjected to codon optimization and screening, resulting in an enhanced expression level as compared to the wild-type coding sequence without codon optimization.

For example, the codon optimized coding sequence of CYP4V2 can achieve an expression level about 2-fold, about 3-fold, about 4-fold, about 5-fold, about 10-fold, about 15-fold, or about 20-fold as compared to the wild-type coding sequence by Western blot analysis of CYP4V2 protein expression levels in HEK293 cells and ARPE-19 cells.

Preferably, the codon optimized coding sequence of CYP4V2 has a reduced CpG number and/or a reduced number of CpG island. For example, the codon optimized coding sequence comprises less than 100 CpG, less than 70 CpG, less than 20 CpG, less than 15 CpG, less than 10 CpG, less than 5 CpG or 0 CpG. For example, the codon optimized coding sequence does not have CpG islands. By "CpG island" it stands for a DNA region of at least 200 bp in length, a GC percentage content greater than 50%, and an observed-to-expected CpG ratio greater than 60%.

For example, the codon-optimized coding sequence has a percentage sequence identity of lower than 80% as compared to the wild-type coding sequence of CYP4V2 as shown in SEQ ID NO: 1. The percentage identity of two sequences can be calculated by known programs in the art. Due to the different parameters for alignment and different definition of identity, the calculated percentage identity of two sequences may vary depending on the program being used to do the calculation. In the present disclosure, blastn is used to obtain the percentage identity of two nucleotide sequences, and specifically a "highly similar sequences (megablast)" mode is selected.

The codon-optimized coding sequence can be selected from a group consisting of the nucleotide sequences as set forth in SEQ ID NOs: 2-17. Preferably, the codon-optimized coding sequence is any one of SEQ ID NOs: 8, 9, 15, 16 and 17. More preferably, the codon-optimized coding sequence is SEQ ID NO: 16.

The regulatory sequences comprised in the nucleic acid molecule can be selected from one or more of promoter, enhancer, polyadenylation sequence, and translation termination signal. A certain combination of regulatory sequences of the present disclosure can achieve unexpected effect in improving the expression efficiency of the coding sequence.

The promoter of the present disclosure can be a constitutive promoter, a tissue-specific promoter or a cell type-specific promoter. For example, the promoter can be an RPE cell-specific promoter. The promoter can be the native promoter of CYP4V2. In a more preferred embodiment, the promoter is a CAG promoter having a sequence as set forth in SEQ ID NO. 35. CAG promoter is a strong constitutive promoter which drives high levels of gene expression in mammalian expression vectors. CAG promoter consists of a cytomegalovirus (CMV) early enhancer element, a promoter which is picked from the first exon and the first intron of chicken beta-actin gene and a splice acceptor of the rabbit beta-globin gene.

The Kozak consensus sequence (Kozak sequence), named after the scientist who discovered it, is a nucleic acid motif in most eukaryotic mRNA transcripts that naturally functions as the protein translation initiation site[14]. Kozak sequence ensures the protein is correctly translated and enhances protein expression.

In addition, the nucleic acid of the present disclosure can further comprise an intron inserted between the promoter and the coding sequence. As known in the art, some introns may enhance the expression of genes in eukaryotes. The intron of the present disclosure can be a part of the naturally occurring intron of the CYP4V2 gene.

The polyadenylation sequence of the present disclosure can be bGH polyA, SPA or SV40 polyA [15], preferably SV40 polyA. Anyone of the polyA can be combined with a Woodchuck Hepatitis Virus posttranscriptional regulatory element (WPRE)[16], which is a DNA sequence, when transcribed, creates a tertiary structure enhancing expression, and configured as WPRE-bGH polyA, WPRE-SPA or WPRE-SV40 poly A, respectively.

In preferred embodiment of the present disclosure, the nucleic acid sequence comprises a nucleotide sequence encoding for a CAG promoter, a Kozak sequence, a codon-optimized coding sequence of CYP4V2 gene, and a WPRE-SV40 polyA. For example, the isolated nucleic acid sequence comprises a nucleotide sequence of any one of SEQ ID NOs: 18-34. In a more preferred embodiment, the isolated nucleic acid sequence comprises a nucleotide sequence of any one of SEQ ID NOs: 25, 26, 32, 33, and 34. In the most preferred embodiment, the isolated nucleic acid sequence comprises a nucleotide sequence of SEQ ID NO: 33.

rAAV Vectors and Viral Particles

The nucleic acid molecule of the present disclosure can be constructed into a recombinant AAV vector, to obtain rAAV particles for delivery into treatment subjects.

In addition to the inserted nucleotide sequence as described above, the rAAV vectors are in single stranded form. The rAAV vector is usually comprised of two inverted terminal repeat (ITR) sequences at both ends of the inserted nucleotide sequence. The ITR of the present disclosure can be ITR derived from any AAV serotypes. When reference is made to serotype of AAV ITR, the phrase "derived from" means that the ITR can be the ITR of a certain serotype or a variant derived therefrom with modification(s). In a preferred embodiment of the present disclosure, the rAAV vector comprises two ITRs derived from AAV2[17]. For example, the rAAV vector comprises two AAV2 ITRs, or comprises a wild-type AAV2 ITR and an AAV2 ITR variant lacking region C or region C'. For example, the wild-type AAV2 ITR locates at a position at 5' of the inserted nucleotide sequence, while the AAV2 ITR variant locates at a position at 3' of the inserted nucleotide sequence; or vice versa.

The rAAV genome was packaged into an AAV capsid. The capsid can be derived from any AAV serotype known in the art or characterized in the future. The capsid and ITRs can be derived from the same serotype of AAV or from different serotypes of AAV. Preferably, the capsid is suitable for eye delivery, e.g., subretinal, intravitreal or intraocular delivery. In a specific embodiment, the AAV vector comprises a capsid of AAV1, AAV2, AAV4, AAV5, AAV7, AAV8, AAV9, AAVrh10, AAV2.7m8, or AAVAnc80L65 serotype, or a variant thereof.

In a preferred embodiment of the present disclosure, the rAAV is comprised of AAV serotype 8 capsids[18]. Evidence have shown that ssAAV8 transduces photoreceptors and retinal pigment epithelial cells (RPE) more efficiently than ssAAV2 and ssAAV5. Under the guidance of the capsid proteins, the virus transduces target cells and then the transferred genome containing CYP4V2 gene and regulatory elements is released into the targeted RPE. The released rAAV genome remains stable and independent from the host genome to stably produce functional CYP4V2 protein in the treatment subjects.

Pharmaceutical Composition

The term "pharmaceutical composition" refers to a composition suitable for delivering to a subject. The pharmaceutical composition of the present disclosure comprises the isolated nucleic acid, the rAAV vector or the viral particle of the present disclosure and a pharmaceutically acceptable excipient. Conventional pharmaceutically acceptable excipients are known in the art and can be solid or liquid excipients.

Therapeutic Uses

The rAAV, viral particle or composition of the present disclosure can be used to treat or prevent BCD, which is related to CYP4V2 mutations. In addition, the rAAV, viral particle or composition of the present disclosure may also be effective in treating or preventing other conditions or diseases related to retinal pigment epithelium (RPE) atrophy, such as fundus dystrophy.

The term "treat", "treating" or "treatment" includes cure or at least alleviate the symptoms of BCD, or conditions or diseases related to RPE atrophy.

Administration

The terms "administration" and "administering" as used herein, when applied to a subject, e.g. an animal, including human, or to cells, tissue, organ, or biological fluid, mean contact of an exogenous pharmaceutical, therapeutic, diagnostic agent, or composition to the subject, cell, tissue, organ, or biological fluid. The term "administration" also includes in vitro and ex vivo treatments, e.g., of a cell, by a reagent, diagnostic, binding compound, or by another cell.

In the present disclosure, the viral particle or the pharmaceutical composition of the present application is preferably delivered through intra-ocular delivery, e.g., sub-retinal injection.

EXAMPLES

Example 1. Selection of Promoter

The inventors first prepared a CYP4V2-expression AAV vector comprised of two ITRs, a CMV promoter, a wild type CYP4V2 CDS and SV40 polyA[13]. Due to the reported silencing risk of CMV promoter[19], the CMV promoter was latere replaced with a CAG promoter, resulting in a new vector designated as "CAG-hCyp4v2 (BCD1)" which showed significantly improved CYP4V2 protein expression (FIG. 1, lower panel).

Example 2. Codon Optimization Increased Cyp4v2 Expression

To obtain a transgene construct which could provide higher expression levels of the CYP4V2 protein, the coding sequence of CYP4V2 was codon optimized to improve codon usage frequency in human cells. In addition, the GC content and CpG islands of the modified coding sequence were reduced to minimize the potential for TLR9-mediated immune responses in vivo. Based on the above criteria, 16 different coding sequences (SEQ ID NOs: 2-17) were designed, synthesized and cloned into CAG promoter to obtain 16 more transgene constructs (BCD2-BCD17). Following Table 1 shows the CpG number, CpG island number of SEQ ID NOs: 2-17, as well as their sequence homology to the wild-type sequence.

TABLE 1

CpG content, CpG island number and sequence identity percentages of 16 codon-optimized sequences in comparison to the wild-type coding sequence

| Construct ID | Codon ID | CpG number | CpG islands | identity % |
|---|---|---|---|---|
| BCD1 | CYP4V2_wt | 50 | Yes | 100 |
| BCD2 | CYP4V2_co1 | 69 | Yes | 77.15 |
| BCD3 | CYP4V2_co2 | 63 | Yes | 78.23 |
| BCD4 | CYP4V2_co3 | 62 | Yes | 76.89 |
| BCD5 | CYP4V2_co4 | 65 | Yes | 77.34 |
| BCD6 | CYP4V2_co5 | 61 | Yes | 75.56 |
| BCD7 | CYP4V2_co6 | 0 | No | 79.25 |
| BCD8 | CYP4V2_co7 | 12 | No | 78.68 |
| BCD9 | CYP4V2_co8 | 0 | No | 79.12 |
| BCD10 | CYP4V2_co9 | 0 | No | 78.99 |
| BCD11 | CYP4V2_co10 | 0 | No | 79.69 |
| BCD12 | CYP4V2_co11 | 0 | No | 78.29 |
| BCD13 | CYP4V2_co12 | 0 | No | 78.8 |
| BCD14 | CYP4V2_co13 | 0 | No | 79.44 |
| BCD15 | CYP4V2_co14 | 0 | No | 78.74 |
| BCD16 | CYP4V2_co15 | 0 | No | 78.74 |
| BCD17 | CYP4V2_co16 | 1 | No | 76.89 |

Example 3. Transfection of HEK293 and ARPE-19 Cells and Detection of Expression Level HEK293 and ARPE-19 cells were maintained in DMEM+ 10% FBS and passaged every 3 days by TrypLE. The day before transfection, HEK293 cells were inoculated to a 24-well plate at a density of $1\times10^5$ cells/cm$^2$, while ARPE-19 cells were inoculated to a 24-well plate at a density of $7\times10^4$ cells/cm$^2$. Plasmids were transfected using Lipofectamine 3000 Transfection Reagent (Invitrogen, L3000008) following the user's guide. 72 hours after transfection, cells were collected in RIPA lysis buffer (Beyotime, P0013C) with a protease inhibitor cocktail (Roche, 04693159001) and SDS-PAGE loading buffer (Cowin Bio, CW0027), denatured for 15 min at 95° C., centrifuged at 12,000 rpm for 10 min. Supernatants were separated in 4%-10% SDS-PAGE gel (Cowin Bio, CW0022M), and blotted onto 0.45 μm NC transfer membrane (Merck, HATF00010).

The protein expression levels of CYP4V2 and the housekeeping gene GAPDH were detected by an antibody against the human CYP4V2 (Sigma, HPA029122) and GAPDH (Abcam, ab8245), respectively. The gray value of bands were calculated and normalized to BCD1.

Figure 3:
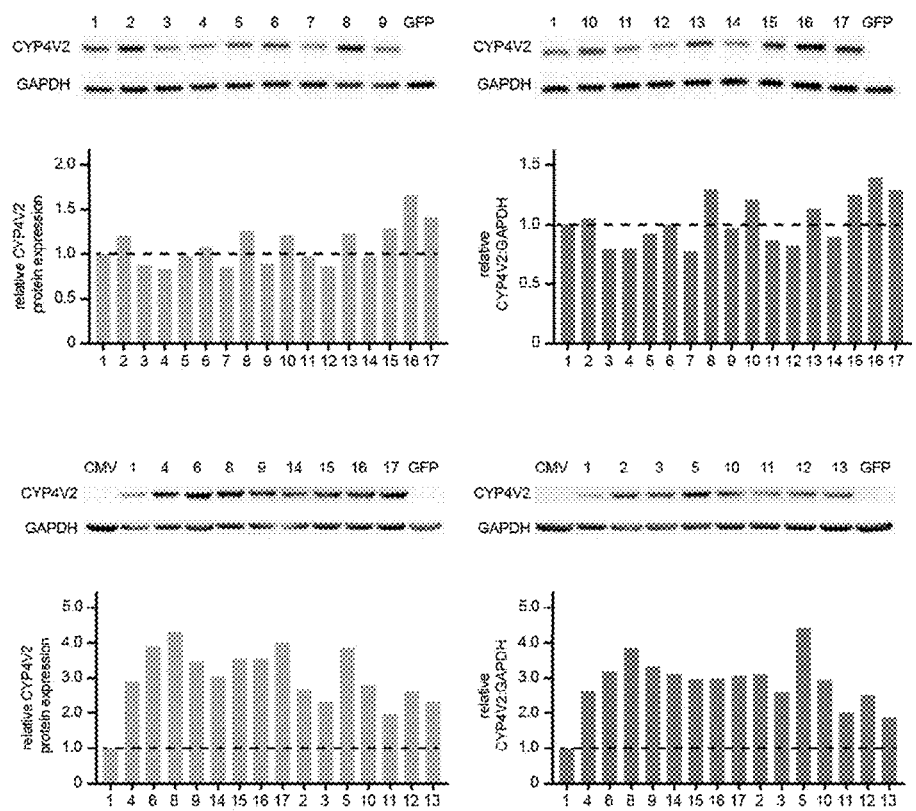
FIG. 3 shows the evaluation of the CYP4V2 transgene protein expression levels of the constructs BCD1-BCD17 in HEK293 cells.
Figure 4:
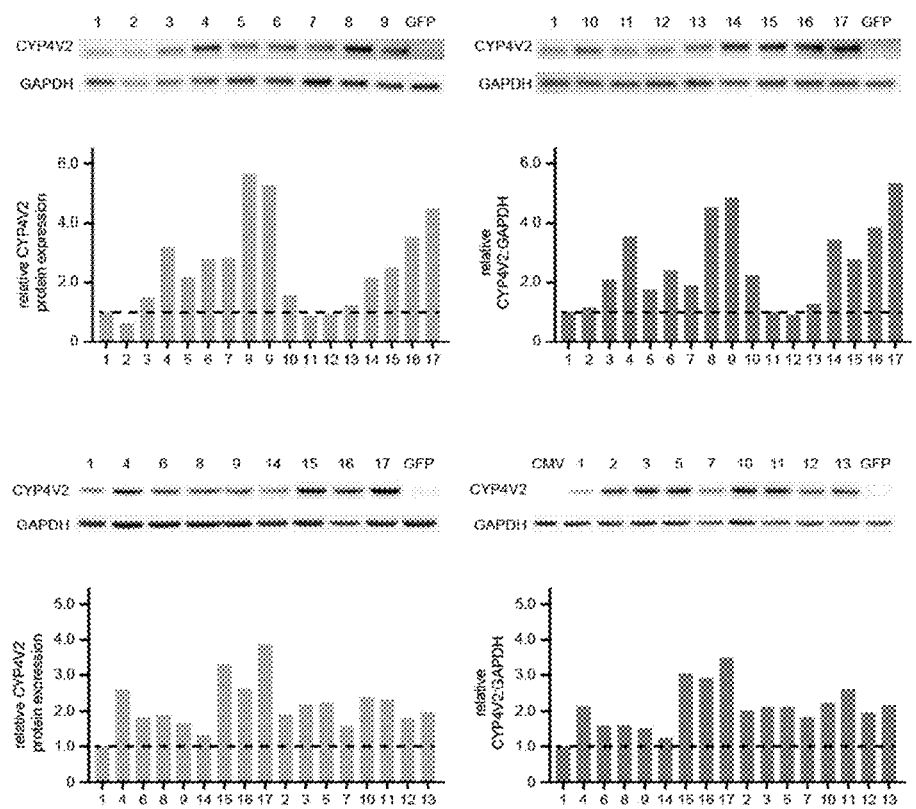
FIG. 4 shows the evaluation of the CYP4V2 transgene protein expression levels of the constructs BCD1-BCD17 in ARPE-19 cells.
Figure 5A:
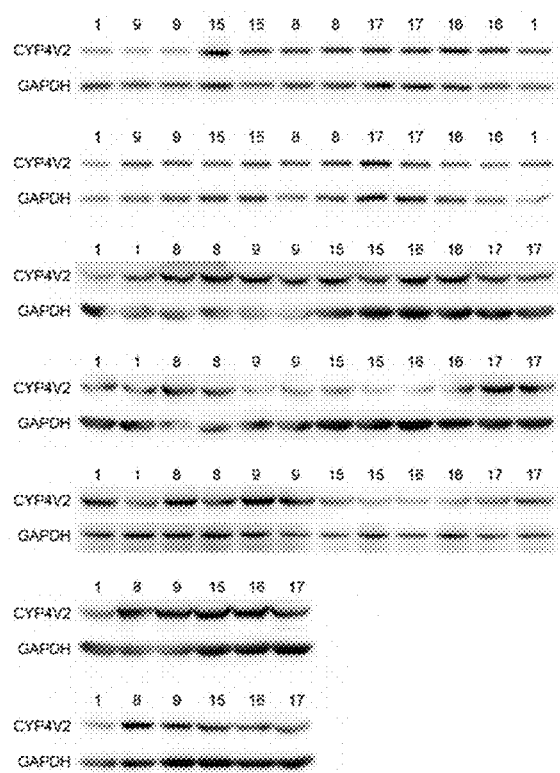
FIG. 5 shows the CYP4V2 transgene protein expression levels of the constructs BCD8, BCD9, BCD15, BCD16, and BCD17 in HEK293 cells. (A) Western blot. (B) Histograms.
Figure 5B:
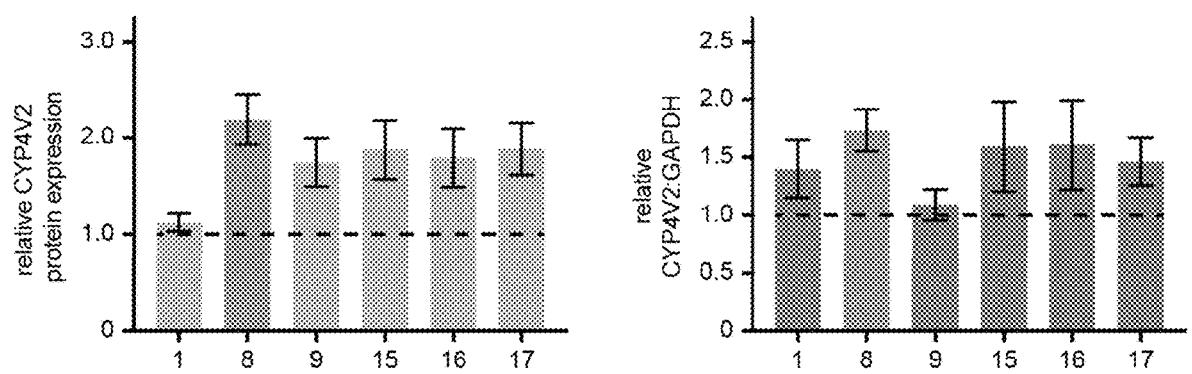
Figure 6A:
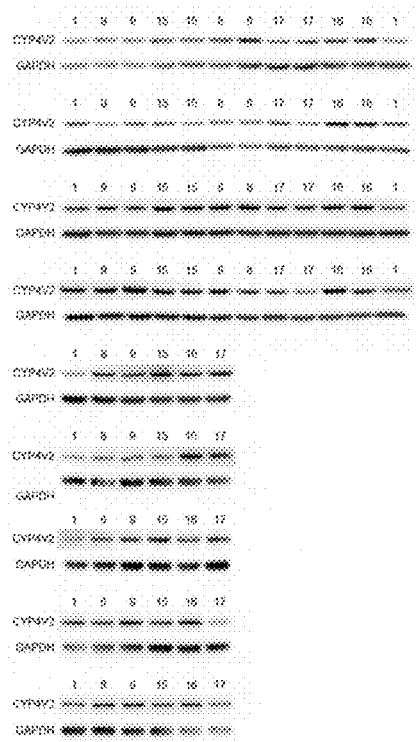
FIG. 6 shows the CYP4V2 transgene protein expression levels of the constructs BCD8, BCD9, BCD15, BCD16, and BCD17 in ARPE-19 cells. (A) Western blot. (B) Histograms.

The results from repeated experiments showed that transgene constructs BCD8, BCD9, BCD15, BCD16, BCD17 expressed CYP4V2 protein at higher levels among the 16 tested codon optimized vectors as evaluated in HEK293 cells (FIG. 3) and ARPE-19 cells (FIG. 4). Accordingly, transgene constructs BCD8, BCD9, BCD15, BCD16 and BCD17 were selected for further evaluation, using BCD1 as a control. Western blot (WB) results are shown in FIG. 5A and FIG. 6A. The gray value of all the bands were calculated, analyzed and normalized to BCD1 (FIG. 5B and FIG. 6B).

Figure 6B:
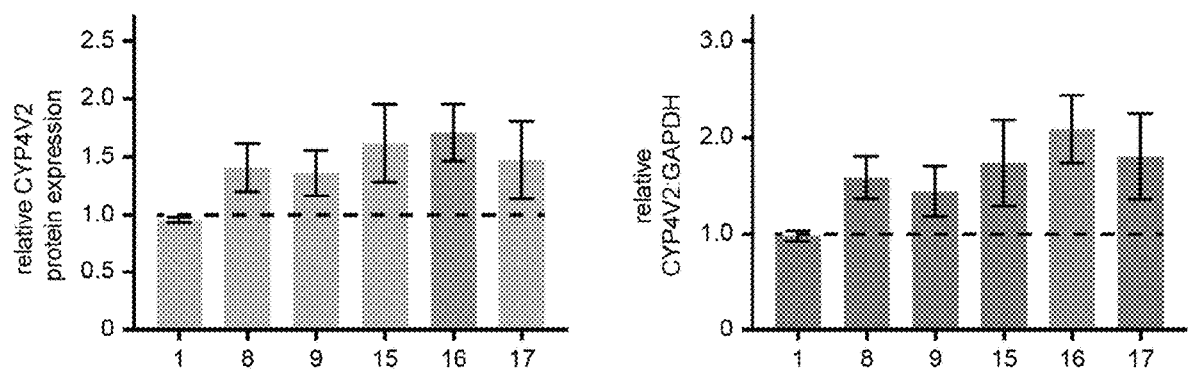

Based on the Western blot results, it was determined that BCD8 exhibited the highest CYP4V2 protein expression levels in HEK293 cells (FIG. 5A and FIG. 5B) and BCD16 exhibited the highest CYP4V2 protein expression levels in ARPE-19 cells (FIG. 6A and FIG. 6B).

Later, BCD1, BCD8, and BCD16 were packaged to replication-defective AAV8, respectively. AAV8-BCD1, AAV8-BCD8 and AAV8-BCD16 virus particles were used to transduce ARPE-19 at MOI=$5\times10^5$ in the presence of 2 mM hydroxyurea.

Figure 7A:
FIG. 7 shows the CYP4V2 transgene protein expression levels of the packaged AAV8-BCD1, AAV8-BCD8, and AAV8-BCD16 in the transduced ARPE-19 cells. (A) Western blot. (B) Histograms.
Figure 7B:
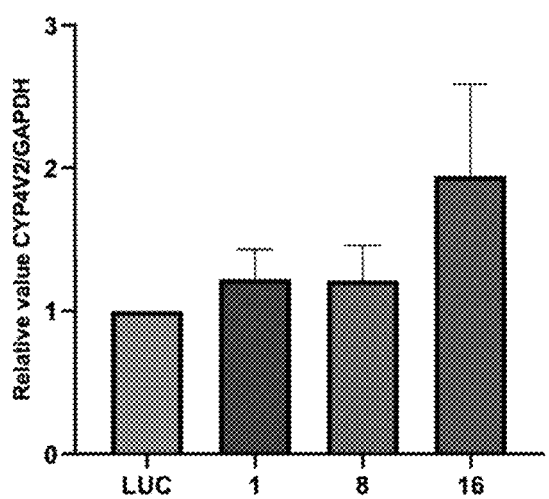

The AAV transduction experiment showed that AAV8-BCD16 had the highest expression levels (FIG. 7A and FIG. 7B).

REFERENCES

1. Friedmann T, Roblin R. Gene therapy for human genetic disease? Science. 1972; 175: 949-955.
2. Mckusick V A. Mendelian inheritance in man and its online version, omim. Am J Hum Genet. 2007; 80: 588-604.
3. Chen R, Shi L S, Hakenberg J, Naughton B, Sklar P, Zhang J G et al. Analysis of 589,306 genomes identifies individuals resilient to severe mendelian childhood diseases. Nat Biotechnol. 2016; 34: 531-538.
4. Dunbar C E, High K A, Joung J K, Kohn D B, Ozawa K, Sadelain M. Gene therapy comes of age. Science. 2018; 359.
5. Ginn S L, Amaya A K, Alexander I E, Edelstein M, Abedi M R. Gene therapy clinical trials worldwide to 2017: An update. J Gene Med. 2018; 20.
6. Casal M, Haskins M. Large animal models and gene therapy. Eur J Hum Genet. 2006; 14: 266-272.
7. Bietti G B. Ueber familiaeres vorkommen von "retinitis Punctata albescens" (verbunden mit "dystrophia Marginalis cristallinea corneae"): Glitzern des glaskoerpers und anderen degenerativen augenveraenderungen. Klin Mbl Augenheilk. 1937; 99: 737-756.
8. Jiao X D, Munier F L, Iwata F, Hayakawa M, Kanai A, Lee J et al. Genetic linkage of bietti crystallin corneoretinal dystrophy to chromosome 4q35. Am J Hum Genet. 2000; 67: 1309-1313.
9. Hu D N. Ophthalmic genetics in china. Ophthalmic Paed Gen. 1983; 2: 39-45.
10. Li A, Jiao X, Munier F L, Schorderet D F, Yao W, Iwata F et al. Bietti crystalline corneoretinal dystrophy is caused by mutations in the novel gene cyp4v2. Am J Hum Genet. 2004; 74: 817-826.
11. Kaiser-Kupfer M I, Chan C-C, Markello T C, Crawford M A, Caruso R C, Csaky K G et al. Clinical biochemical and pathologic correlations in bietti's crystalline dystrophy. American Journal of Ophthalmology. 1994; 118: 569-582.
12. Lai T Y Y, Chu K O, Chan K P, Ng T K, Yam G H F, Lam DSC et al. Alterations in serum fatty acid concentrations and desaturase activities in bietti crystalline dystrophy unaffected by cyp4v2 genotypes. Invest Ophth Vis Sci. 2010; 51: 1092-1097.
13. Qu B, Wu S, Jiao G, Zou X, Li Z, Guo L et al. Treating bietti crystalline dystrophy in a high-fat diet-exacerbated murine model using gene therapy. Gene Therapy. 2020.
14. Kozak M. An analysis of 5'-noncoding sequences from 699 vertebrate messenger rnas. Nucleic acids research. 1987; 15: 8125-8148.

15. Connelly S, Manley J L. A functional mrna polyadenylation signal is required for transcription termination by rna polymerase ii. Genes & development. 1988; 2: 440-452.
16. Zufferey R, Donello J E, Trono D, Hope T J. Woodchuck hepatitis virus posttranscriptional regulatory element enhances expression of transgenes delivered by retroviral vectors. Journal of virology. 1999; 73: 2886-2892.
17. Grimm D, Kern A, Rittner K, Kleinschmidt J A. Novel tools for production and purification of recombinant adenoassociated virus vectors. Hum Gene Ther. 1998; 9: 2745-2760.
18. Gao G P, Alvira M R, Wang L, Calcedo R, Johnston J, Wilson J M. Novel adeno-associated viruses from rhesus monkeys as vectors for human gene therapy. Proceedings of the National Academy of Sciences of the United States of America. 2002; 99: 11854-11859.
19. Tenenbaum L, Chtarto A, Lehtonen E, Velu T, Brotchi J, Levivier M. Recombinant aav—mediated gene delivery to the central nervous system. The Journal of Gene Medicine: A cross—disciplinary journal for research on the science of gene transfer and its clinical applications. 2004; 6: S212-S222.

The invention claimed is:

1. An isolated nucleic acid molecule, comprising the nucleotide sequence of SEQ ID NO: 8, 9, 15, 16 or 17, and that encodes human CYP4V2 polypeptide.

2. The isolated nucleic acid molecule of claim 1, wherein the nucleotide sequence is SEQ ID NO: 8 or SEQ ID NO: 16.

3. The isolated nucleic acid molecule of claim 1, further comprising a promoter operatively linked to the 5' of the nucleotide sequence encoding CYP4V2.

4. The isolated nucleic acid molecule of claim 3, wherein the promoter is a CAG promoter.

5. The isolated nucleic acid molecule of claim 1, further comprising a polyadenylation sequence at the 3' of the nucleotide sequence encoding CYP4V2.

6. The isolated nucleic acid molecule of claim 5, wherein the polyadenylation (polyA) sequence is bovine growth hormone (bGH) polyA, synthesized polyA (SPA) or Simian Virus 40 (SV40) polyA.

7. The isolated nucleic acid molecule of claim 1, further comprising a Woodchuck Hepatitis Virus posttranscriptional regulatory element (WPRE).

8. The isolated nucleic acid molecule of claim 1, comprising the nucleotide sequence of SEQ ID NO:25 having SEQ ID NO:8, the nucleotide sequence of SEQ ID NO:26 having SEQ ID NO:9, the nucleotide sequence of SEQ ID NO:32 having SEQ ID NO:15, the nucleotide sequence of SEQ ID NO:33 having SEQ ID NO:16, or the nucleotide sequence of SEQ ID NO:34 having SEQ ID NO:17.

9. A recombinant AAV (rAAV) vector, comprising the nucleic acid molecule of claim 1.

10. The recombinant AAV vector of claim 9, comprising two inverted terminal repeats.

11. The recombinant AAV vector of claim 10, comprising two AAV2 inverted terminal repeats.

12. A viral particle comprising the recombinant AAV vector of claim 9 packaged into an AAV capsid.

13. The viral particle of claim 12, wherein the AAV capsid is AAV8 capsid.

14. A pharmaceutical composition comprising the viral particle of claim 12, and a pharmaceutically acceptable excipient.

15. A method of alleviating a symptom of Bietti Crystalline Dystrophy (BCD) in a mammalian subject, comprising administering via subretinal injection of an effective amount of the rAAV vector of claim 9 to the subject.

* * * * *